(12) United States Patent
Simeone et al.

(10) Patent No.: US 8,148,147 B2
(45) Date of Patent: Apr. 3, 2012

(54) COMPOSITIONS AND METHODS FOR TREATING AND DIAGNOSING PANCREATIC CANCER

(75) Inventors: Diane M. Simeone, Ann Arbor, MI (US); Michael F. Clarke, Menlo Park, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 126 days.

(21) Appl. No.: 12/019,339

(22) Filed: Jan. 24, 2008

(65) Prior Publication Data

US 2008/0261244 A1 Oct. 23, 2008

Related U.S. Application Data

(60) Provisional application No. 60/897,190, filed on Jan. 24, 2007.

(51) Int. Cl.
*C12N 5/071* (2010.01)
*C12N 5/00* (2006.01)
*C12N 5/02* (2006.01)

(52) U.S. Cl. ........................................ 435/366; 435/325

(58) Field of Classification Search .................. 435/366, 435/325

See application file for complete search history.

(56) References Cited

U.S. PATENT DOCUMENTS

| | | |
|---|---|---|
| 3,687,808 A | 8/1972 | Merigan |
| 4,109,496 A | 8/1978 | Allemann |
| 4,323,546 A | 4/1982 | Crockford |
| 4,411,990 A | 10/1983 | Salmon et al. |
| 4,612,282 A | 9/1986 | Schlom et al. |
| 4,670,393 A | 6/1987 | Seeburg |
| 4,816,567 A | 3/1989 | Cabilly |
| 4,873,191 A | 10/1989 | Wagner |
| 4,968,103 A | 11/1990 | McNab |
| 4,981,785 A | 1/1991 | Nayak |
| 5,019,497 A | 5/1991 | Olsson |
| 5,034,506 A | 7/1991 | Summerton |
| 5,061,620 A | 10/1991 | Tsukamoto et al. |
| 5,087,570 A | 2/1992 | Weissman et al. |
| 5,223,409 A | 6/1993 | Ladner |
| 5,225,539 A | 7/1993 | Winter |
| 5,283,317 A | 2/1994 | Saifer |
| 5,358,691 A | 10/1994 | Clark |
| 5,489,677 A | 2/1996 | Sanghvi |
| 5,534,617 A | 7/1996 | Cunningham |
| 5,538,848 A | 7/1996 | Livak |
| 5,539,082 A | 7/1996 | Nielsen |
| 5,545,806 A | 8/1996 | Lonberg |
| 5,545,807 A | 8/1996 | Surani |
| 5,565,332 A | 10/1996 | Hoogenboom et al. |
| 5,569,825 A | 10/1996 | Lonberg |
| 5,585,089 A | 12/1996 | Queen |
| 5,589,376 A | 12/1996 | Anderson et al. |
| 5,599,677 A | 2/1997 | Dowell |
| 5,602,240 A | 2/1997 | de Mesmaeker |
| 5,614,396 A | 3/1997 | Bradley |
| 5,625,126 A | 4/1997 | Lonberg |
| 5,631,169 A | 5/1997 | Lakowicz |
| 5,633,425 A | 5/1997 | Lonberg |
| 5,639,606 A | 6/1997 | Willey |
| 5,641,870 A | 6/1997 | Rinderknecht |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,661,016 A | 8/1997 | Lonberg |
| 5,672,480 A | 9/1997 | Dowell |
| 5,672,499 A | 9/1997 | Anderson et al. |
| 5,674,739 A | 10/1997 | Shyjan |
| 5,688,666 A | 11/1997 | Bass |
| 5,693,482 A | 12/1997 | Anderson et al. |
| 5,705,188 A | 1/1998 | Junichi et al. |
| 5,714,331 A | 2/1998 | Buchardt |
| 5,719,262 A | 2/1998 | Buchardt |
| 5,731,168 A | 3/1998 | Carter |
| 5,750,373 A | 5/1998 | Garrard |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,807,522 A | 9/1998 | Shalon |
| 5,814,511 A | 9/1998 | Chang et al. |
| 5,821,108 A | 10/1998 | Akashi et al. |
| 5,824,489 A | 10/1998 | Anderson et al. |

(Continued)

FOREIGN PATENT DOCUMENTS

EP 1004669 5/1998

(Continued)

OTHER PUBLICATIONS

Visvader et al. Nature Reviews, Cancer 8: 755-768, 2008.*

(Continued)

*Primary Examiner* — Thaian N Ton
(74) *Attorney, Agent, or Firm* — Casimir Jones, S.C.

(57) ABSTRACT

The present invention relates to the field of oncology and provides novel compositions and methods for diagnosing and treating pancreatic cancer. In particular, the present invention provides pancreatic cancer stem cells useful for the study, diagnosis, and treatment of solid tumors.

11 Claims, 7 Drawing Sheets

U.S. PATENT DOCUMENTS

Figure 1:
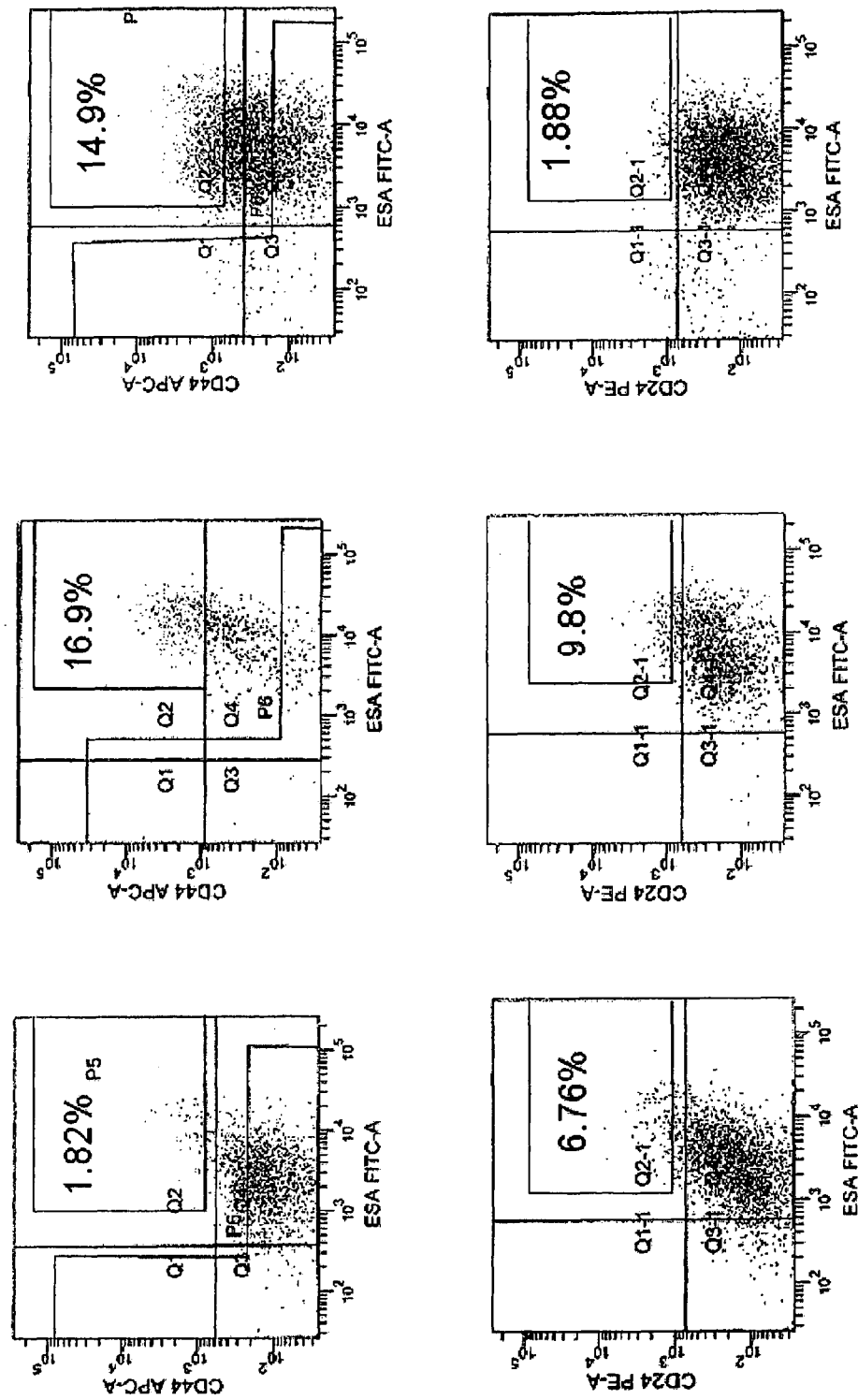

| | | |
|---|---|---|
| 5,824,544 A | 10/1998 | Armentano |
| 5,830,730 A | 11/1998 | German |
| 5,834,598 A | 11/1998 | Lowman |
| 5,849,535 A | 12/1998 | Cunningham |
| 5,849,553 A | 12/1998 | Anderson et al. |
| 5,849,869 A | 12/1998 | Artavanis-Tsakonas et al. |
| 5,851,832 A | 12/1998 | Weiss et al. |
| 5,854,026 A | 12/1998 | Cunningham |
| 5,856,441 A | 1/1999 | Artavanis-Tsakonas et al. |
| 5,859,535 A | 1/1999 | Liu |
| 5,869,282 A | 2/1999 | Ish-Horowicz et al. |
| 5,872,154 A | 2/1999 | Wilson et al. |
| 5,876,978 A | 3/1999 | Willey |
| 5,885,530 A | 3/1999 | Babson |
| 5,885,808 A | 3/1999 | Spooner |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek |
| 5,986,170 A | 11/1999 | Subjeck |
| 5,994,106 A | 11/1999 | Kovesdi |
| 5,994,128 A | 11/1999 | Fallaux |
| 5,994,132 A | 11/1999 | Chamberlain |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl |
| 6,022,711 A | 2/2000 | Cunningham |
| 6,033,908 A | 3/2000 | Bout et al. |
| 6,054,297 A | 4/2000 | Carter |
| 6,080,912 A | 6/2000 | Bremel |
| 6,083,904 A | 7/2000 | Artavanis-Tsakonas |
| 6,090,922 A | 7/2000 | Artavanis-Tsakonas |
| 6,117,985 A | 9/2000 | Thomas et al. |
| 6,121,045 A | 9/2000 | McCarthy et al. |
| 6,136,563 A | 10/2000 | Cunningham |
| 6,136,952 A | 10/2000 | Li |
| 6,143,523 A | 11/2000 | Cunningham |
| 6,149,902 A | 11/2000 | Artavanis-Tsakonas et al. |
| 6,156,305 A | 12/2000 | Brauker |
| 6,159,750 A | 12/2000 | Edmonds |
| 6,180,370 B1 | 1/2001 | Queen |
| 6,190,876 B1 | 2/2001 | Rubin |
| 6,197,523 B1 | 3/2001 | Rimm et al. |
| 6,198,107 B1 | 3/2001 | Seville |
| 6,207,147 B1 | 3/2001 | Hiserodt |
| 6,218,166 B1 | 4/2001 | Ravindranath |
| 6,262,025 B1 | 7/2001 | Ish-Horowicz |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,433,138 B1 | 8/2002 | Zimrin et al. |
| 6,448,229 B2 | 9/2002 | Teall et al. |
| 6,506,559 B1 | 1/2003 | Fire |
| 6,537,775 B1 | 3/2003 | Tournier-Lasserve et al. |
| 6,582,904 B2 | 6/2003 | Dahm |
| 6,583,115 B1 | 6/2003 | Kopchick et al. |
| 6,632,620 B1 | 10/2003 | Makarovskiy |
| 6,664,098 B1 | 12/2003 | Sakano et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,716,974 B1 | 4/2004 | Maciag et al. |
| 6,825,007 B2 | 11/2004 | Zimrin |
| 6,936,440 B1 | 8/2005 | Cunningham |
| 6,984,522 B2 | 1/2006 | Clarke |
| 7,022,499 B2 | 4/2006 | Sakano |
| 7,049,296 B2 | 5/2006 | Pineiro et al. |
| 7,081,340 B2 | 7/2006 | Baker et al. |
| 7,115,360 B2 | 10/2006 | Clarke |
| 7,118,890 B2 | 10/2006 | Ish-Horowicz et al. |
| 7,122,675 B2 | 10/2006 | Josien et al. |
| 7,230,004 B2 | 6/2007 | Adams et al. |
| 7,253,265 B2 | 8/2007 | Sakano |
| 7,304,138 B2 | 12/2007 | Maciag et al. |
| 7,361,336 B1 | 4/2008 | Bergstein |
| 7,413,873 B2 | 8/2008 | Waterman |
| 7,449,303 B2 | 11/2008 | Coignet |
| 7,498,304 B2 | 3/2009 | Kotkow et al. |
| 7,534,868 B1 | 5/2009 | Papadopoulos |
| 7,569,345 B2 | 8/2009 | Cobleigh et al. |
| 7,655,674 B2 | 2/2010 | Beachy et al. |
| 7,682,607 B2 | 3/2010 | Rhee |
| 7,708,998 B2 | 5/2010 | Dudek et al. |
| 7,714,014 B2 | 5/2010 | He et al. |
| 2002/0119565 A1 | 8/2002 | Clarke et al. |
| 2002/0137129 A1 | 9/2002 | Barnes |
| 2002/0151487 A1 | 10/2002 | Nickoloff et al. |
| 2002/0169300 A1 | 11/2002 | Waterman |
| 2003/0032184 A1 | 2/2003 | Lagasse et al. |
| 2003/0044409 A1 | 3/2003 | Carson |
| 2003/0064384 A1 | 4/2003 | Hung et al. |
| 2003/0086934 A1 | 5/2003 | Botstein et al. |
| 2003/0100512 A1 | 5/2003 | Nadin et al. |
| 2003/0114387 A1 | 6/2003 | Pineiro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0165500 A1 | 9/2003 | Rhee |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2004/0023244 A1 | 2/2004 | Griffin |
| 2004/0037815 A1 | 2/2004 | Clarke et al. |
| 2004/0038876 A1 | 2/2004 | Pepinsky et al. |
| 2004/0048249 A1 | 3/2004 | Tang |
| 2004/0058443 A1 | 3/2004 | Artavanis-Tsakonas |
| 2004/0110663 A1 | 6/2004 | Dudek et al. |
| 2004/0127474 A1 | 7/2004 | Dudek et al. |
| 2004/0219579 A1 | 11/2004 | Aziz |
| 2004/0247593 A1 | 12/2004 | He |
| 2005/0026831 A1 | 2/2005 | Bodmer et al. |
| 2005/0054568 A1 | 3/2005 | Ling et al. |
| 2005/0059093 A1 | 3/2005 | Bodmer et al. |
| 2005/0070578 A1 | 3/2005 | Baxter et al. |
| 2005/0085519 A1 | 4/2005 | Rubin et al. |
| 2005/0089518 A1 | 4/2005 | Clarke et al. |
| 2005/0089896 A1 | 4/2005 | Roy et al. |
| 2005/0112121 A1 | 5/2005 | Artavanis-Tsakonas et al. |
| 2005/0112125 A1 | 5/2005 | Burkly et al. |
| 2005/0137130 A1 | 6/2005 | Bodmer et al. |
| 2005/0187179 A1 | 8/2005 | Miele et al. |
| 2005/0201975 A1 | 9/2005 | Champion et al. |
| 2005/0221476 A1 | 10/2005 | Sen et al. |
| 2005/0222087 A1 | 10/2005 | Beachy et al. |
| 2005/0232927 A1* | 10/2005 | Clarke et al. ............... 424/155.1 |
| 2005/0244388 A1 | 11/2005 | Peterson et al. |
| 2005/0261477 A1 | 11/2005 | Champion et al. |
| 2005/0272063 A1 | 12/2005 | Nakamura |
| 2006/0019256 A1 | 1/2006 | Clarke et al. |
| 2006/0019320 A1 | 1/2006 | Civenni |
| 2006/0040883 A1 | 2/2006 | You |
| 2006/0083682 A1 | 4/2006 | Bergstein |
| 2006/0084588 A1 | 4/2006 | Briend et al. |
| 2006/0122373 A1 | 6/2006 | McCarthy et al. |
| 2006/0134121 A1 | 6/2006 | Thurston et al. |
| 2006/0263774 A1 | 11/2006 | Clark et al. |
| 2007/0041984 A1 | 2/2007 | Bergstein et al. |
| 2007/0082846 A1 | 4/2007 | Ish-Horowicz et al. |
| 2007/0099209 A1 | 5/2007 | Clarke |
| 2007/0105133 A1 | 5/2007 | Clarke et al. |
| 2007/0190647 A1 | 8/2007 | Clarke et al. |
| 2007/0220621 A1 | 9/2007 | Clarke et al. |
| 2007/0231325 A1 | 10/2007 | Clarke et al. |
| 2007/0243192 A1 | 10/2007 | Wicha et al. |
| 2007/0265246 A1 | 11/2007 | Clevers et al. |
| 2008/0014196 A1 | 1/2008 | Yan |
| 2008/0019961 A1 | 1/2008 | Wicha et al. |
| 2008/0038230 A1 | 2/2008 | Lindeman et al. |
| 2008/0064049 A1 | 3/2008 | Clarke et al. |
| 2008/0107648 A1 | 5/2008 | Noguera |
| 2008/0112940 A1 | 5/2008 | Liaw |
| 2008/0118520 A1 | 5/2008 | Li et al. |
| 2008/0131908 A1 | 6/2008 | Li et al. |
| 2008/0181899 A1 | 7/2008 | Papadopoulos |

| | | | |
|---|---|---|---|
| 2008/0187938 | A1 | 8/2008 | Wicha et al. |
| 2008/0188405 | A1 | 8/2008 | Di Fiore et al. |
| 2008/0226621 | A1 | 9/2008 | Fung |
| 2008/0261244 | A1 | 10/2008 | Wicha et al. |
| 2008/0299540 | A1* | 12/2008 | Ince et al. ............ 435/4 |
| 2008/0305107 | A1 | 12/2008 | Bergstein et al. |
| 2009/0004205 | A1 | 1/2009 | Clarke et al. |
| 2009/0011441 | A1 | 1/2009 | Bergstein |
| 2009/0022740 | A1 | 1/2009 | Bergstein |
| 2009/0022741 | A1 | 1/2009 | Bergstein |
| 2009/0028878 | A1 | 1/2009 | Bergstein |
| 2009/0028879 | A1 | 1/2009 | Bergstein |
| 2009/0246199 | A1 | 10/2009 | Noguera-Troise |

FOREIGN PATENT DOCUMENTS

| | | |
|---|---|---|
| EP | 0861894 | 9/1998 |
| EP | 0662827 | 4/2002 |
| EP | 0972041 | 10/2006 |
| EP | 1718767 | 11/2006 |
| WO | WO90/08832 | 8/1990 |
| WO | WO92/19734 | 11/1992 |
| WO | WO94/07474 | 4/1994 |
| WO | WO94/10300 | 5/1994 |
| WO | WO97/01571 | 1/1997 |
| WO | WO97/30731 | 8/1997 |
| WO | WO97/37004 | 10/1997 |
| WO | WO98/05775 | 2/1998 |
| WO | WO98/45434 | 10/1998 |
| WO | WO98/51799 | 11/1998 |
| WO | WO98/57621 | 12/1998 |
| WO | WO99/02685 | 1/1999 |
| WO | WO00/06726 | 2/2000 |
| WO | WO00/09675 | 2/2000 |
| WO | WO00/12738 | 3/2000 |
| WO | WO00/20576 | 4/2000 |
| WO | WO00/52143 | 9/2000 |
| WO | WO01/40466 | 6/2001 |
| WO | WO01/98354 | 12/2001 |
| WO | WO01/98537 | 12/2001 |
| WO | WO02/00576 | 1/2002 |
| WO | 02/12447 | 2/2002 |
| WO | WO02/18544 | 3/2002 |
| WO | WO02/78703 | 10/2002 |
| WO | WO02/088081 | 11/2002 |
| WO | WO02/092635 | 11/2002 |
| WO | WO02/102978 | 12/2002 |
| WO | WO03/004045 | 1/2003 |
| WO | WO03/000893 | 3/2003 |
| WO | WO03/042246 | 5/2003 |
| WO | 03/050502 | 6/2003 |
| WO | WO03/047316 | 6/2003 |
| WO | WO03/062273 | 7/2003 |
| WO | WO03/088964 | 10/2003 |
| WO | WO2004/001004 | 12/2003 |
| WO | WO204/073657 | 2/2004 |
| WO | WO2004/032838 | 4/2004 |
| WO | WO2004/042028 | 5/2004 |
| WO | WO2004/065545 | 8/2004 |
| WO | WO2004/091383 | 10/2004 |
| WO | 2005/005601 | 1/2005 |
| WO | WO2005/026334 | 3/2005 |
| WO | 2005/074633 | 8/2005 |
| WO | WO2006/052128 | 5/2006 |
| WO | WO2006/027693 | 12/2006 |
| WO | WO2006/138275 | 12/2006 |
| WO | WO2007/100640 | 9/2007 |
| WO | WO2007/143689 | 12/2007 |
| WO | WO2008/050362 | 5/2008 |
| WO | WO2008/051797 | 5/2008 |
| WO | WO2008/057144 | 5/2008 |
| WO | WO2008/070042 | 6/2008 |
| WO | WO2008/076960 | 6/2008 |
| WO | WO2008/091222 | 7/2008 |
| WO | WO2008/092002 | 7/2008 |
| WO | WO2008/108910 | 9/2008 |
| WO | WO2008/136848 | 11/2008 |
| WO | WO2008/139202 | 11/2008 |
| WO | WO2009/013569 | 1/2009 |
| WO | WO2009/025867 | 2/2009 |
| WO | WO2009/035522 | 3/2009 |
| WO | WO2009/075565 | 6/2009 |
| WO | WO2004/097030 | 11/2010 |

OTHER PUBLICATIONS

Cancer Res., 66(4): 1891-1896, 2006.*
Clarke et al. Cancer Res., 66: 9339-9344, 2006.*
Liu. Cancer Res., 60: 3429-3434, 2000.*
Heidt et al. J. of Surgical Research, 130(2): 194-195, Abstract #89, Feb. 2006, available online Jan. 25, 2006.*
Hathorn et al. Cancer, 74: 1904-11, 1994).*
Janeway et al. Immunobiology, 20: Appendix 1, 579-581, 1999.*
Thampoe et al. Arch. Biochem. Biophys., 267: 342-352, 1988.*
Leclerc et al. Cancer Cell International, 2: 1, pp. 1-5, 2002.*
Bustin. J. of Mol. Endocrinology, 25: 169-193, 2000.*
Piselli et al. (Anticancer Res., 20: 825-832, 2000.*
Li et al. Identification of pancreatic cancer stem cells. Cancer Research, Feb. 1, 2007, vol. 67, No. 3, pp. 1030-1037.
Olempska et al. Detection of tumor stem cell markers in pancreatic carcinoma cell lines. Hepatobiliary and Pancreatic Diseases International, Feb. 15, 2007, vol. 6, No. 1, pp. 92-97.
Shah et al. Development and characterization of gemcitabine-resistant pancreatic tumor cells. Annals of Surgical Oncology, Dec. 1, 2007, vol. 14, No. 12, pp. 3629-3637.
Zencak et al., The Journal of Neuroscience, Jun. 15, 2005, 25(24):5774-5783.
Bracken et al., The EMBO Journal, vol. 22, No. 20 pp. 5323-5335,2003.
Reya T, Morrison, SJ, Clarke MF, and Weissman IL. Stem cells, cancer, and cancer stem cells. Nature 2001; 414: 105-111.
Bonnet D, Dick IE. Human acute myeloid leukemia is organized as a hierarchy that originates from a primitive hematopoietic cell. Nature Med 1997; 3:730-737.
Lapidot T, et. al. A cell initiating human acute myeloid leukemia after transplantation into SCID mice. Nature 1994; 17: 645-648.
Al-Hajj M, Wicha MS, Benito-Hernandez A, Morrison SI, Clarke MF. Prospective identification of tumorigenic breast cancer cells. Proc Natl Acad Sci USA. 2003; 100: 3983-8.
Singh SK, Hawkins C, Clarke ID, Squire IA, Bayani I, Hide T, Henkelman RM, Cusimano MD, Dirks PB Identification of human brain tumour initiating cells. Nature. 2004; 432: 396-401.
Galli R, Binda E, Orfanelli U, Cipelletti B, et al. Isolation and characterization of tumorigenic, stem-like neural precursors from human glioblastoma. Cancer Res 2004; 64: 7011-7021.
Hemmati HD, Nakano I, Lazareff IA, Masterman-Smith M, et al. Cancerous stem cells arise from pediatric brain tumors. Proc Natl Acad Sci USA 2003; 100: 15178-15183. 21.
Patrawala L, Calhoun T, Schneider-Broussard R, Li H, et al. Highly purified CD44+ prostate cancer cells from xenograft human tumors are enriched in tumorigenic and metastatic progenitor cells. Oncogene 2006; 25: 1696-1708.
Szotek PP, Pieretti-Vanmarcke R, Masiakos PT, et al. Ovarian cancer side population defines cells with stem cell-like characteristics and Mullerian inhibiting substance responsiveness. Proc Nati Acad Sci 2006; 103: 11154-11159.
Costello RT, Mallet F, Gaugler B, Sainty D, et al. Human acute myeloid leukemia CD34+/CD38− progenitor cells have decreased sensitivity to chemotherapy and Fas induced apoptosis, reduced immunogenicity, and impaired dendritic cell transformation capacities. Cancer Res 2000; 60: 4403-4411.
Dean M, Fojo T, Bates S. Tumour stem cells and drug resistance. Nat Rev Cancer 2005; 5: 274-284.
Guzman ML, Swiderski CF, Howard DS, Grimes BA, et al. Preferential induction of apoptosis for primary human leukemic stem cells. Proc Natl Acad Sci USA 2002; 99: 16220-16225.
Arumugam T, Simeone DM, Van Golen K, Logsdon CD. SIOOP promotes pancreatic cancer growth, survival, and invasion. Clin Cancer Res 2005; 11: 5356-5364.
Logsdon CD, Simeone DM, Binkley C, et. al. Molecular profiling of pancreatic adenocarcinoma and chronic pancreatitis identifies multiple genes differentially regulated in pancreatic cancer. Cancer Res 2003; 63: 2649-2657.

Hahn SA, Seymour AB, Hoque AT, et. al. Allelotype of pancreatic adenocarcinoma using xenograft enrichment. Cancer Res 1995; 55: 4670-4675.

Singh SK, Clarke ID, Terasaki M, Bonn VE, Hawkins C, Squire J, Dirks PB. Identification of a cancer stem cell in human brain tumors. Cancer Res. 2003; 63: 5821-8.

Richardson GD, Robson CN, Lang SH, Neal DE, et al. CD133, a novel marker for human prostate epithelial stem cells. J Cell Sci 2004; 117: 3539-3545.

Weichert W, Denkert C, Burkhardt M, Gansukh T, et al. Cytoplasmic CD24 expression in colorectal cancer independently correlates with shortened patient survival. Clin Cancer Res. 2005; 11:6574-81.

Li L, Neaves WB. Normal stem cells and cancer stem cells: the niche matters. Cancer Res 2006; 66: 4553-4557.

Liu S, Dontu G, Mantle ID, Patel S, Ahn NS, Jackson KW, Suri P, Wicha MS. Hedgehog signaling and Bmi-1 regulate self-renewal of normal and malignant human mammary stem cells. Cancer Res. 2006, 66 (12):6063-71.

Park I-K, Morrison SJ, Clarke MF. Bmi1, stem cells, and senescence regulation. J Clin Invest 2004; 113: 175-179.

Androutsellis-Theotokis A, Leker RR, Soldner F, et al. Notch signaling regulates stem cell Nos. In vitro and in vivo. Nature 2006; 442: 823-826.

Lie DC, Colamarino SA, Song HJ, et al. Wnt signaling regulates adult hippocampal neurogenesis. Nature 2005; 437: 1370-1375.

Yilmaz OH, Valdez R, Theisen BK, Guo W, et al. Pten dependence distinguishes hematopoietic stem cells from leukemia-initiating cells. Nature 2006; Apr. 5;; 441(7092) p. 475-82.

Ayyanan A, Civenni G, Ciarloni L, Morel C, et al. Increased Wnt signaling triggers oncogenic conversion of human breast epithelial cells by a Notch dependent mechanism. 23 Proc Natl Acad Sci USA 2006; 103: 3799-3804.

Pasca DI Magliano M, Hebrok M. Hedgehog signaling in cancer formation and maintenance. Nat Rev Cancer 2003; 3: 903-911.

Thayer SP, Pasca DI Magliano M, Heiser PW, Nielson CM, et al. Hedgehog is an early and late mediator of pancreatic cancer tumorigenesis. Nature 2003; 425: 851-856.

Berman DM, Karhadkar SS, Maitra A, De Oca RM, et al. Widespread requirement for hedgehog ligand stimulation in growth of digestive tract tumours. Nature 2003; 425: 846-851.

Fang D, Nguyen TK, Leishear K, Finko R, Kulp AN, Hotz S, Van Belle PA, Xu X, Elder DE, Herlyn M. A tumorigenic subpopulation with stem cell properties in melanomas. Cancer Res. 2005; 65: 9328-37.

Cengel K. A., Targeting Sonic Hedgehog: a new way to mow down pancreatic cancer? Cancer Biol & Ther, 2004, 3:165-166.

Katoh Y et al., Hedgehog signaling pathway and gastrointestinal stem cell signaling network, International J Mol Med, 2006, 18:1019-1023.

Abraham et al., "Prevalence of CD44+/CD24−/low cells in breast cancer may not be associated with clinical outcome but may favor distant metastasis" Clin Cancer Res, 2005, vol. 11: 1154-9.

Ahrens et al., "Soluble CD44 inhibits melanoma tumor growth by blocking cell surface CD44 binding to hyaluronic acid," Oncogene vol. 20, pp. 3399-3408 (Jun. 2001).

Ailles et al. "Cancer stem cells in solid tumors" Current Opinion in Biotechnology, 2007, vol. 18, pp. 460-466.

Akashi, et al. Transcriptional accessibility for genes of multiple tissues and hematopoietic lineages is hierarchically controlled during early hematopoiesis. Blood. 101(2) pp. 383-389 (2003).

Allenspach et al. "Notch signaling in cancer." Cancer Biology & Therapy. Sep./Oct. 2002, vol. 1, pp. 466-476.

Allman, et al. "Notch signaling in hematopoiesis and early lymphocyte development" Immunol Rev 187, 75-86 (2002).

Ameyar et al, "A role for AP-1 in apoptosis: the case for and against" Biochimie vol. 85, pp. 747-52 (2003).

Ascoli, et al: "Utility of Cytokeratin 20 in Identifying the Origin of Metastatic Carcinomas in Effusions" Diagnostic Cytopathology, 1995, pp. 303-308, vol. 12, No. 4.

Aubele, et al. "Heterogeneity in breast cancer and the problem of relevance of findings," Analyt. Cell Path. (1999) 19: 53-8.

Austin et al., "glp-1 is required in the germ line for regulation of the decision between mitosis and meiosis in C. elegans," Cell vol. 51 pp. 589-99 (1987).

Austin, et al. "A role for the Wnt genie family in hematopoiesis: expansion of multilineage progenitor cells" Blood 89, 3624-35 (1997).

Badolato, et al., "Differential expression of surface membrane growth hormone receptor on human peripheral blood 4 lymphocytes detected by dual fluorochrome flow cytometry," J. Clinical Endocrinology and Metabolism, 1994, vol. 79, pp. 984-990.

Bafico A et al, "An autocrine mechanism for constitutive Wnt pathway activation in human cancer cells" Cancer Cell, 6: 497-506 (2004).

Balzar et al, "The biology of the 17-1A antigen (Ep-CAM)" J Mol Med, 1999, vol. 77: 699-712.

Baran et al., "Detection of cancer cells in the blood by FACS sorting of CD45-cells" International J. Molecular Medicine, vol. 1,pp. 573-578 (1998).

Barbui, A. et al.: 'Negative selection of peripheral blood stem cells to support a tandem autologotransplantation programme in multiple myeloma' British Journal of Haematology. vol. 116, 2002, pp. 202-210.

Bartel et al. "Elimination of false positives that arise in using the two-hybrid system" Biotechniques vol. 14, 1993, pp. 920-924.

Baum, C. M. et al.: 'Isolation of a candidate human hematopoietic stem-cell population' Proc Natl Acad Sci USA vol. 89, 1992, pp. 2804-2808.

Bea, S., et al., BMI-1 Gene Amplification and Overexpression in Hematological Malignancie Occur Mainly in Mantle Cell Lymphomas, Cancer Research, vol. 61, pp. 2409-12 (2001).

Bea,S., et al., Increased No. Of Chromosomal Imbalances and High-Level DNA Amplifications in Mantle Cell Lymphoma Are Associated With Blastoid Variants, Blood. vol. 93, pp. 4365-74 (1999).

Beachy, P., et al., "Tissue repair and stem cell renewal in carcinogenesis," Nature 432:324-331, Nature Publishing Group, New York, NY, U.S.A. (2004).

Beerman, et al. "Flow Cytometric Analysis of Dna Stemline Heterogeneity in Primary and Metastatic Breast Cancer," Cytometry (1991) 12(2): 147-54.

Bellavia, D., et al., "Constitutive activation of NF-KBand T-cell leukemia/lymphoma in Notch3 transgenic mice," EMBO J. 19:3337-3348, Oxford University Press, New York, NY U.S.A. (2000).

Beniers et al., Establishment and Characterization of Five New Human Renal Tumor Xenografts, Am J Pathol 1992; 140: 482-95.

Berg et al., "Bispecific antibodies that mediate killing of cells infected with human immunodeficiency virus of any strain" PNAS, vol. 88, 1991, pp. 4723-4727.

Bergsagel, et al. "Growth Characteristics of a Mouse Plasma Cell Tumor," Cancer Research vol. 28, pp. 2187-2196 (1968).

Berruyer et al, "Vanin-1-/- Mice Exhibit a Glutathione-Mediated Tissue Resistance to Oxidative Stress" Mol Cell Biol vol. 24, pp. 7214-7224 (2004).

Berry, et al. "Germ-line tumor formation caused by activation of glp-1, a Caenorhabditis elegans member of the Notch family of receptors" Development, vol. 124. pp. 925-36 (1997).

Bhatavdekar et al., "Overexpression of CD44: A Useful Independent Predictor of Prognosis in Patients with Colorectal Carcinomas," Ann Surg Oncol 1998:5:495-501.

Bhattacharjee a et al, "Classification of human lung carcinomas by mRNA expression profiling revewals distinct adenocarcinoma subclasses" Proc. Natl Acad. USA 98: 13790-5 (Nov. 2001).

Bienz "β-Catenin: A Pivot between Cell Adhesion and Wnt-signalling," Current Biology vol. 15, pp. R64-R67 (2004).

Blyszczuk P. et al. "Embryonic stem cells differentiate into insulin-producing cells without selection of nestin-expressing cells." Int. J. Dev. Biol., 48:1095-104 (2004).

Bodey et al "Failure of cancer vaccines: the significant limitations of this approach to immunotherapy" 2000, Anticancer Res, 20: 2665-2676.

Boggs et al, "A glycosynapse in myelin?" Glycoconjugate J. vol. 21, pp. 97-110 (2004).

Bonsing et al. "Allelotype analysis of flow-sorted breast cancer cells demonstrates genetically related diploid and aneuploid subpopulations in primary tumors and lymph node metastases" Genes Chromosomes & Cancer (2000) 82: 173-183.

Bonsing et al., "High Levels of DNA Index Het rog neity in Advanced Breast Carcinomas," Cancer 71: 382-391 (1993).

Bottcher et al, "Fibroblast Growth Factor Signaling during Early Vertebrate Development," Endocrine Reviews, vol. 26, pp. 63-77 (2005).

Brabletz et al, "Variable catenin expression in colorectal cancers indicates tumor progression driven by the tumor environment" PNAS, vol. 98, pp. 10356-10361 (Aug. 28, 2001).

Bradley et al. "Formation of germ-line chimaeras from embryo-derived teratocarcinoma cell lines" Nature vol. 309, 1984, p. 255-6.

Braun S. et al. "The ERBB2 Oncogene identifies breast cancer stem cells: Prognotic and therapeutic implications" Breast Cancer Research and Treatment, 1999, p. 121, vol. 67, No. 1, Nijhoff, Boston, US.

Bray, S.J., "Notch signalling: a simple pathway becomes complex," Nature 7:678-689, Nature PUblishing Group (2006).

Brennan, K. and Brown, A.M.C., "Is there a role for Notch signalling in human breast cancer?" Breast Cancer Res. 5:69-75, BioMed Central Ltd, London, UK (2003).

Brinster et al. "Factors affecting the efficiency of introducing foreign DNA into mice by microinjecting eggs" Proc. Natl. Acad. Sci. USA vol. 82, 1985, pp. 4438-4442.

Bromberg et al., Tissue factor promotes melanoma metastasis by a pathway independent of blood coagulation, PNAS 1995; 92: 8205-9.

Brown, "NCI's Anticancer Drug Screening Program May Not Be Selecting for Clinically Active Comounds" Oncology Research, vol. 9, pp. 213-215 (1997).

Bruce, W. R.; Gaag, H.: 'A quantitative assay for the number of murine lymphoma cells capable of proliferation in vivo' Nature vol. 199, 1963, pp. 79-80.

Bruckner, et al. "Glycosyltransferase activity of Fringe modulates Notch-Delta interactions" Nature 406, pp. 411-415 (2000).

Brummelkamp et al. "A system for stable expression of short interfering RNAs in mammalian cells" Science vol. 296, 2002, pp. 550-553.

Buskens, C. et al. (Digestive Disease Week Abstracts and Itinerary Planner, 2003, abstract No. 850).

Cabrera et al "Phenocopies induced with antisense RNA identify the wingless gene" 1987, Cell, 50: 659-63.

Krebs, L.T., et al., "Notch signaling is essential for vascular morphogenesis in mice," Genes & Dev. 14:1343-1352, Cold Spring Harbor Laboratory Press, Woodbury NY, U.S.A. (2000).

Kristiansen et al. "Tumour Biological aspects of CD24, a mucin-Like adhesion molecule," J Mol Histol V., 2004, 35: (255-262).

Kufe et al., "Biological Behavior of Human Breast Carcinoma-associated Antigens Expresses during Cellular Proliferation," Cancer Research, vol. 43, pp. 851-857 (1983).

Kummermehr, et al. "The Proliferative Structure of Malignant Tumours," Stem Cells (Academic Press, London 1997) pp. 363-399.

Kurochkin et al, "ALEX1, a Novel Human Armadillo Repeat Protein That Is Expressed Differentially in Normal Tissues and Carcinomas" Biochem Biophys Res Commun, vol. 280, pp. 340-347 (2001).

Kuukasjarvi et al., "Genetic Heterogeneity and Clonal Evolution Underlying Development of AsynchronoMetastasis in Human Breast Cancer," Cancer Res. (Apr. 15, 1997) 57: 1597-1604.

Lagasse, et al. 'bcl-2 inhibits apoptosis of neutrophils but not their engulfment by macrophages' J Exp Med vol. 179, 1994, pp. 1047-1052.

Lahn et al, "Protein Kinase C Alpha Expression in Breast and Ovarian Cancer" Oncology vol. 67, pp. 1-10 (2004).

Lai et al., "Mouse Cell Surface Antigens: Nomenclature and Imnrunophenotyping," 1998, p. 87.

Lam "A new type of synthetic peptide library for identifying ligand-binding activity" Nature vol. 354, 1991, pp. 82-84.

Lam "Application of combinatorial library methods in cancer research and drug discovery" Anticancer Drug Des vol. 12, 1997, p. 145-67.

Larochelle et al. "Identification of primitive human hematopoietic cells capable of repopulating NOD/SCID mouse bone marrow: Implications for gene therapy," Nature Medicine vol. 2, pp. 1329-1337 (1996).

Lauffer "Targeted relaxation enhancement agents for MRI" Magnetic Resonance in Medicine vol. 22, 1991, pp. 339-342.

Lauret, E. et al., "Membrance-bound Delta-4 Notch Ligand reduces the proliferative activity of primitive human hematopoietic CD34+CD38low cells while maintaining their LTC-IC potential," Leukemia 18:788-797 (Feb. 2006).

Lee et al, Mutational analysis of NOTCH1, 2,3 and 4 genes in common solid cancers and acute leukemias APMIS 115: 1357-1363, 2007.

Lee J-S et al, "Intracisternal Type a Particle-Mediated Activation of the Notch41int3 Gene in a Mouse Mammary Tumor: Generation of Truncated Notch41int3 mRNAs qy Retroviral Splicing Events," J Virol (Jun. 1999) 73(6) 5166-5171.

Lee, et al. "Increased vaccine-specific T cell frequency after peptide-based vaccination correlates with increased susceptibility to in vitro stimulation but does not lead to tumor regression" 1999 J Immunol, 163: 6292-6300.

Leethanakul, et al., "Distinct pattern of expression of differentiation and growth-related genes in aquamocell carcinomas of the head and neck revealed by the used of laser capture microdissection and cDNA arrays," Oncogene vol. 19, pp. 3220-3224 (2000).

Leong "Pitfalls in diagnostic immunohistology" Adv. Anat Pathol. 11 (2): 86-93, 2004; Abstract Only.

Lessard, J. & Sauvageau, G. Bmi-1 Determines the Proliferative Activity of Normal and Leukemic Stem Cells Nature 255-261 (2003).

Li, et al. "Cloning, characterization, and the complete 56.8-kilobase DNA sequence of the human NOTCH4 gene" 1998, Genomics, 51: 45-48.

Li, et al. "Evidence that transgenes encoding components of the Wnt signaling pathway preferentially induce mammary cancers from progenitor cells." Proc. Natl. Acad. Sci. USA, 100:15853-8 (2003).

Li, et al. "Notch signaling from tumor cells: A new mechanism of angiogenesis," Cancer Cell 8:1-3, Cell Press (2005).

Liang,et al. "Attempts: a heparin/protamine-based delivery system for enzyme drugs," J. Controlled Release 78:67-79 (2002).

Lippman, M.E., "High-dose chemotherapy plus autologous bone marrow transplantation for metastatic breast cancer" N. Engl J. Med 342,1119-20 (2000).

Liu, A. et al. "Cell-cell interaction in prostate generegulation and cytodifferentiation" Proc. Natl. Acad. Sc. U.S.A 94, 10705-10 (1997).

Liu, et al. "Inhibition of endothelial cell proliferation by Notch 1 signaling is mediated by repressesing MAPK and P14K/Akt pathways and requires MAML1," FASEB J. 20:E201-E210 (May 2006).

Liu, et al. "Regulation of Notch1 and Dll4 by Vascular Endothelial Growth Factor in Arterial Endothelial Cells: Implications for Modulating Arteriogenesis and Angiogenesis," Molecular and Cellular Biology 23:14-25, American Society for Microbiology (2003).

Livak, K. J. & Schmittgen, T. D. Analysis of relative gene expression data using real-time quantitative PCR and the 2(-Delta Delta C(T)) Method. Methods 25, 402-8 (2001).

Loeppen et al,. "Overexpression of Glutamine Synthetase is Associated with Catenin Mutations in Mouse Liver Tumors Durng Promotion of Hepatocarcinogenesis by Phenobartbital" Cancer Research vol. 62, pp. 5685-5688 (2002).

Lunter et al "Activated leukosyte adhision molecule (CD166), a novel actor in invasive growth, controls matrix metalloproteinase activity," Cancer Res, 2005, vol. 65, pp. 8801-8808.

Ma, et al. "Functional Expression and Mutations of c-Met and Its Therapeutic Inhibition with SU11274 and Small Interfering RNA in Non-Small Cell Lung Cancer" Cancer Research vol. 65, pp. 1479-1488 (2005).

Madura et al. "N-recognin/Ubc2 interactions in the N-end rule pathway" J. Biol. Chem. vol. 268, 1993, pp. 12046-12054.

Mahajan et al, "NRC-interacting Factor 1 is a Novel Cotransducer That Interacts with and Regulated the Activity of the Nuclear Hormone Receptor Coactivator NRC" Molecular and Cellular Biology vol. 22, pp. 6883-6894 (2002).

Mailhos, C., et al., "Delta4, an endothelial specific Notch ligand expressed at sites of physiological and tumor angiogenesis," Differentiation 69:135-144, Blackwell Wissenschafts-Verlag (Dec. 2001).

Maillard et al. "Mastermind critically regulates Notch-mediated lymphoid cell fate decisions." Blood, 2004, vol. 104, pp. 1696-1702.

Marambaud et al, "A presenilin-1/secretase cleavage releases the E-cadherin intracellular domain and regulates disassemble of adhrens junctions" EMBO 21: 1948 (2002).

Martin et al., "Immunomagnetic enrichment of disseminated epithelial tumor cells from peripheral blood by MACS" Exp Hematol 1998; 26: 252-64.

Martin, et al. "Ein neuer Zugang zu 2'-0-Alkylribonucleosiden and Eigenschaften deren Oligonucleotide" Helv. Chim. Acta vol. 78, 1995, p. 486.

Martinez et al, "Single-Stranded Antisense si-RNAs Guide Target RNA Cleavage un RNAi" Cell, vol. 110, pp. 563-574 (2002).

Masson Soluble CD44: quantification and molecular repartition in plasma of patients with colorectal cancer, Brit J Cancer 1999; 1995-2000.

Matsushita, et al. "The latrophilin family: multiply spliced G protein-coupled receptors with differential tissue distribution" FEBS Letters 1999 vol. 443 pp. 348-352.

May, W., et al. "EWS/FLI1-induced manic fringe renders NIH 3T3 cells tumorigenic" Nat Genet. 17(4) pp. 495-7 (1997).

Mcconnell et al. "The cytosensor microphysiometer: biological applications of silicon technology" Science vol. 257, 1992, pp. 1906-1912.

Medina et al, "Glutamine Metabolism: Nutritional and Clinical Significance," American Soc. For Nutritional Sciences, J. of Nutrition vol. 131, pp. 2539S-2542S (2001).

Mellman "Where Next for Cancer Immunotherapy?" 2006, The Scientist, 20(1): 47-56.

Michallet, M. et al.: 'Transplantation with selected autologoperipheral blood CD34+Thyl+ hematopoietic stem cells (HSCs) in multiple myeloma: impact of HSC dose on engraftment, safety, and immune reconstitution' EXP Hematol vol. 28, 2000, pp. 858-870.

Miele, L. and Osborne, B., Arbiter of Differentiation and Death: Notch Signaling Meets Apoptosis, Journal of Cellular Physiology 181:393-409, Wiley-Liss, Inc. (1999).

Miele, L., "Notch Signaling," Clin. Cancer Res. 12:1074-1077, American Association for Cancer Research (2006).

Milano, et al. Modulation of Notch processing by D-secretase inhibitors causes intestinal goblet cell metaplasia and induction of genes known to specify gut secretory lineage differentiation. Toxicol Sci 2004;82:341-58.

Porter et al, "The Efficient Design of Transplantable Tumor Assays" Br. J Cancer vol. 17, pp. 583-595 (1964).

Prince, "Identification of a subpopulation of cells with cancer stem cell properties in head and neck squamocell carcinoma," PNAS 2007, vol. 104, pp. 973-978.

Purow, B.W., et al., "Expression of Notch-1 and Its Ligands, Delta-Like-1 and Jagged-1, Is Critical for Clioma Cell Survival and Proliferation" Cancer Res. 65:2353-2363, BioMed Central Ltd, London, UK (2005).

Putnam, D. and Kopecek, J., "Polymer Conjugates with Anticancer Activity," Adv. Polymer Sci. 122:55-123 (1995).

Qin, et al. "p53-independent NOXA induction overcomes apoptotic resistance of malignant melanomas" Molecular Cancer Therapeutics. vol. 3. pp. 895-902 (2004).

Raaphorst, F., et al. "Coexpression of BMI-1 and EZH2 Polycomb Group Genes in Reed-Stemberg Cells of Hodgkin's Disease" Am. J. Pathology, vol. 157, pp. 709-715 (2000).

Rae, et al. "Novel Association of a Diverse Range of Genes with Renal Cell Carcinoma as Identified by Differential Display," Int. J. Cancer 88:726-32, Wiley-Liss, Inc., Massachusetts, U.S.A (2000).

Rafi et al, "A large deletion together with a point mutation in the GALC gene is a common mutant allele in patients with infantile Krabbe disease" Hum Mol Genet, vol. 4, pp. 1285-1289 (1995).

Ramalho-Santos, et al. "Sternness': Transcriptional Profiling of Embyonic and Adult Stem Cells," Science vol. 298, pp. 597-600 (2002).

Ramaswamy S. et al, "A molecular signature of metastasis in primary solid tumors" Nat. Genet 33: 49-54 (2003).

Reya et al, "Wnt Signaling Regulates B Lymphocyte Proliferation through a LEF-1 Dependent Mechanism," Immunity vol. 13, pp. 15-24 (2000).

Reya et al. "Wnt signalling in stem cells and cancer" 2005, Nature 434: 843-50.

Ridgway, et al. "Inhibition of 0114 signaling inhibits tumour growth by deregulating angiogenesis," Nature 444:1083-1087, Nature Publishing Group, New York, NY, U.S.A. (2006).

Rijsewijk et al, "The Drosophila homolog of the mouse mammary oncogene int-1 is identical to the segment polarity gene wingless" 1987, Cell 50: 649-57.

Rivas, et al. "New developments in the study of biomolecular associations via sedimentation equilibrium" Trends Biochem Sci vol. 18, 1993, pp. 284-287.

Robertson et al. "Germ-line transmission of genes introduced into cultured pluripotential cells by retroviral vector" Nature vol. 322, 1986, p. 445-8.

Robey, E., et al., "An Activated Form of Notch Influences the Choice between CD4 and CD8 T Cell Lineages," Cell 87:483-492, Elsevier Inc., Amsterdam, The Netherlands (1996).

Robinson et al, "Further Check points in Th1 Development" Immunity vol. 16, pp. 755-758 (2002).

Rosenkilde et al, "The chemikine system—a major regulator of angiogenesis in health and disease" APMIS, vol. 112, pp. 481-495 (2004).

Rudy et al, "The two major CD44 proteins expressed on a metastatic rat tumor cell line are derived from different splice variants: each one individually suffices to confer metastatic behavior" Cancer Res. 1993, 1262-8.

Sahin et al, "RPL38, FOSL1 and UPP1 Are Predominantly Expressed in the Pancreatic Ductal Epithelium" Pancreas, vol. 30, pp. 158-167 (2005).

Saitoh et al., "Molecular Cloning and Characterization of Human Frizzled-8 Gene on Chromosome 10p11.2" (2001) International Journal of Oncology 18:991-996.

Sakakibara et al.,"Growth and Metastasis of Surgical Specimens of Human Breast Carcinomas in SCID Mice," Cancer Journal from Scientific American (Sep./Oct. 1996) 2: 291-300.

Salmon "Development and applications of a human tumor colony assay for chemosensitivity testin" Recent Results in Cancer Research 94: 8-16 (1984).

Salmon, et al. "Primary Bioassay of Ovarian Carcinoma Stem Cells" AACR Abstracts 19: 231, Abstract No. 922 (Mar. 1978).

Sambrook et al, "Molecular Cloning: A laboratory Manual," 1989, Cold Spring Harbor Press pp. 9.31-9.58.

Santamaria et al, "Cathepsin L2 a Novel Human Cysteine Proteinase Produced by Breast and Colorectal Carcinomas" Cancer Res. vol. 58, pp. 1624-1630 (1998).

Sarcoma: Stedman's Dictionary, 2004.

Sazani, et al, "Nuclear antisense effects of neutral, anionic and cationic oligonucleotide analogs" Nucleic Acids Research, vol. 29, pp. 3965-3974 (2001).

Scehnet, et al. "Inhibition of 0114 signaling induces proliferation of immature vessels and results in poor tissue perfusion" Blood 2007;109:4753-60.

Schenck et al, "A highly conserved protein family interacting with the fragile X mental retardation protein (FMRO) and displaying selective interactions . . ." PNAS, vol. 98, pp. 8844-8849 (2001).

Schlag, et al. "Chemosensitivity testing of human neoplasm using the soft agar colony assay," Cancer Treatment Reviews 11 Suppl A: (1984) 131-7.

Schlosshauer, P. W. et al. APC truncation and increased beta-catenin levels in a human breast cancer cell line. Carcinogenesis 21, 1453-6 (2000).

"Schoenhard et al., 2002, Am. J. Physiol. Cell. Physiol. vol. 283 pp. C103-C114 Alternative splicing yields novel BMAL2 variants:tissue distribution and functional characterization".

Scott, et al. "Searching for peptide ligands with an epitope library" Science vol. 249, 1990, pp. 386-390.

Seki et al., Inhibition of liver metastasis formation by anti-CD44 variant exon 9 monoclonal antibody, Int. J Oncol 1997; 11: 1257-61.

Sell, et al. "Maturation arrest of stem cell differentiation pathway for the cellular origin of teratocarcinomas and epithelial cancers" 1994, Lab Invest. 70, 6-22.

Sevignani, et al. "Tumorigenic conversion of p53-deficient colon epithelial cells by an activated Ki-ras Gene," J Clin Invest 1998; 101: 1572-80.

Shawber, C.J., et al., "Notch Signaling in Primary Endothelial Cells," Ann. NY. Acad. Sci. 995: 162-170, New York Academy of Sciences (2003).

Shen L et al., "Genome-wide Search for Loss of Heterozygosity Using Laser Capture Microdissected Tissue of Breast Carcinoma: An implication for Mutator Phenotype and Breast Cancer Pathogenesis," Cancer Res.(Jul. 15, 2000) 60: 3884.

Shimizu, K. et al. "Manic fringe and lunatic fringe modify different sites of the Notch2 extracellular region, resulting in different signaling modulation" J Biol.Chem. 276, 25753-25758 (2001).

Shridhar et al, "Loss of Expression of a New Member of the DNAJ Protein Family Confers Resistance to Chemotherapeutic Agents Used in the Treatment of Ovarian Cancer" Cancer Research vol. 61, pp. 4258-4265 (2001).

Shutter, Jr., et al., "0114, a novel Notch ligand expressed in arterial endothelium," Genes & Dev. 14:1313-1318, Cold Spring Harbor Laboratory Press, Woodbury NY, U.S.A. (2000).

Silverman "Implications for Tnase L in Prostate Cancer Biology" Biochemistry, vol. 42, pp. 1805-1812 (2003).

Singh D et al, "Gene Expression Correlates of Clinical Prostate Cancer Behavior" Cancer Cells, 1: 203-9 (2002).

Singh et al. "Cell surface-expressed Thomsen-Friedenreich antigen in colon cancer is predominantly carried on high molecular weight splice variants of CD44" Jul. 2001 Glyobiology vol. 11 pp. 587-592.

Sinicrope et al. "Sulindac sulfide-induced apoptosis is enhanced by a small-molecule Bcl-2 inhibitor and by TRAIL in human colon cancer cells overexpressing Bcl-2" Mol Cancer Ther, 2005, 4: 1475-1483.

Sjölander, et al. "Integrated fluid handling system for biomolecular interaction analysis" Anal. Chem. vol. 63, 1991, pp. 2338-2345.

Slack, "Stem Cells in Epithelial Tissues," Science (Feb. 25, 2000) 287: 1431.

Smith "Cancer and the Immune System" 1994, Clin Immunol, 41(4):841-849.

Dontu et al, "In vitro propagation and transcriptional profiling of human mammary stem/progenitor cells" Gene and Development, 17: 1253-1270, 2003.

Dontu, et al. "Role of Notch signaling in cell-fate determination of human mammary stem/progenitor cells" Breast Cancer Res. vol. 6, pp. R605-R615 (2004).

Leung et al, "Bmi1 is essential for cerebellar development and is overexpressed Xin human medulloblastomas," 2004, Nature, 428: 337-341.

Lewis and Veltmaat, "Next stop, the Twlilight Zone: Hedgehog Network Regulation of Mammary Gland Development," Journal of Mammary Gland Biology and Neoplasia, Apr. 2004, vol. 9, p. 165.

Molofsky et al, "Bmi-1 Dependence distinguishes neural stem cell self-reneal from progenitor proliferation," Nature, 2003, 425 (6961) 962-967.

Park, I. K. et al., "Bmi-1 is required for maintenance of adult self-renewing haematopoietic stem cells," Nature 423, 302-5 (2003).

Taipale et al, "Effects of oncogenic mutations in Smoothened and patched can be reversed by cyclopamine," Nature 2000, 406, 1005-1009.

Taipale et al, "Patched acts catalytically to suppress the activity of Smoothened," Nature 2002, 418, 892-897.

Williams, et al, "Identification of a small molecule inhibitor of the hedgehog signaling pathway: Effects on basal cell carcinoma-like lesions" Proc Natl Acad Sci U S A. Apr. 15, 2003;100(8):4616-21.

Bowman and Wicha, "Cancer Stem Cells: A Step Toward the Cure", Journal of Clinical Oncology, vol. 26, No. 17, Jun. 10, 2008.

Cho, et al. "Isolation and Molecular Characterization of Cancer Stem Cells in MMTV-Wnt-1 Murine Breast Tumors." Stem Cells 2008;26:364-371.

Dontu, et al. "Survival of mammary stem cells in suspension culture: implications for stem cell biology and neoplasia" J Mammary Gland Biol Neoplasia. Jan. 2005;10(1):75-86.

Fillmore et al, "Human breast cancer cell lines contain stem-like cells that self-renew, give rise to phenotypically diverse progeny and survive chemotherapy" Breast Cancer Res, 2008, vol. 10R25: 1-13.

Flow Cytometry: Wikipedia 2009.

Harrington, et al. Regulation of multiple angiogenic pathways by Dll4 and Notch in human umbilical vein endothelial cells. Microvasc Res. 2008;75(2):144-54.

Lee et al., "Pancreatic cancer stem cells" Journal of Clinical Oncology 26(17); 2806-12; 2008.

Metastasis: MedicineNet 2009.

Metastasis: Wikipedia 2009, One Page.

Quintana, E. et al. "Efficient tumour formation by single human melanoma cells." Nature, vol. 456, pp. 593-599 (2008).

Yan, et al. "Chronic DLL4 Blockade Induces Vascular Neoplasms," Nature, vol. 463, pp. E6-E7, Feb. 11, 2010.

"Berman, et al. Widespread requirement for Hedgehog ligand stimulation in growth of digestive tract tumors. Nature 425:U 846-851 (Oct. 23, 2003). Published online Sep. 14, 2003."

Karlstrom et al., "A sensitive and quantitative assay for measuring leavage of presenilin substrates," J. Biol Chem 277(9) pp. 6763-6766, 2002.

Kubo, et al. "Hedgehog signaling pathway is a new therapeutic target for patients with breast cancer" Cancer Research, vol. 64, No. 17 Sep. 2004, pp. 6071-6074.

Katano-M "Hedgehog signaling pathway as a therapeutic target in breast cancer," Cancer Letters, New York, NY, vol. 227, Sep. 28, 2005, pp. 99-104.

Aaboe et al. "SOX4 expression in bladder carcinoma: clinical aspects and in vitro functional characterization" 2006, Cancer Res vol. 66 pp. 3434-3442.

Adachi et al. Abraham et al, "Prevalence of CD44+/CD24−/low cells in breast cancer may not be associated with clinical outcome but may favor distant metastasis" Clin Cancer Res, 2005, vol. 11: 1154-9Novel staging protocol for non-small-cell lung cancers according to MRP-1/CD9 and KAI1/CD82 gene expression 1998, J Clin Oncol vol. 16 pp. 1397-1406.

AJCC Cancer Staging manual, 5th Edition, 1997, pp. 171-180.

Akashi, et al. 'Developmental Biology of Hematopoiesis', 2001, Oxford Univ. Press.

Ali et al., 2003, Norm. Metab. Res. vol. 35pp. 726-733 Epidemiology and biology of insulin-like growth factor binding protein-3 (IGFBP-3) as an anti-cancer molecule.

Alison, et al. "Tissue-based stem cells: ABC transporter proteins take centre stage" 2003 J Pathol vol. 200 pp. 547-550.

Andersen, 1998, Nucleic Acid Hybridization.

Antonchuk & Humphries, 2002, Cell vol. 109pp. 39-45 HOXB4-Induced Expansion of Adult Hematopoietic Stem Cells Ex Vivo.

Artavanis-Tsakonas et al, al. "Notch signaling: cell fate control and signal integration in development" Science 284: 770-6 (Apr. 30, 1999).

Ausubel et al., eds. Current Protocols in Molecular Biology, 1999, J. Wiley:New York.

Baade Ro et al. "Bone morphogenetic protein-5, -6 and -7 inhibit growth and induce apoptosis in human myeloma cells" 2004, Oncogene vol. 23 pp. 3024-3032.

Baki, et al., "Presenilin-1 binds cytoplasmic epithelial cadherin, inhibits cadherinyp120 association, and regulates stability and function of the cadherinycatenin adhesion complex" 2001, PNAS vol. 98 pp. 2381.

Barker et al. "The Yin-Yang of TCF/beta-catenin signaling." 2000, Adv Cancer Res vol. 77 pp. 1-24.

Batlle, et al. "EphB receptor activity suppresses colorectal cancer progression" 2005, Nature vol. 435 pp. 1126-1130.

Baum, C. et al.: 'Bone Marrow Transplantation', 1994, Blackwell Scientific Publications, pp. 53-71.

Bhardwaj et al., 2001, Nat. Immunol vol. 2 pp. 172-180 Sonic hedgehog induces the proliferation of primitive human hematopoietic cells via BMP regulation.

Bieller et al., 2001, DNA Cell Biol. vol. 20 pp. 555-561 Isolation and characterization of the human forkhead gene FOXQ1.

Birchmeier et al. "Met, metastasis, motility and more" 2003, Nat. Mol. Cell. Biol vol. 4 pp. 915.

Blache et al., "SOX9 is an intestine crypt transcription factor, is regulated by the Wnt pathway, and represses the CDX2 and MUC2 genes" 2004 J Cell Biol vol. 166 pp. 37-47.
Boccaccio et al., 2005, Nature vol. 434pp. 396-340 The MET oncogene drives a genetic programme linking cancer to haemostasis.
Boerner et al., "Production of antigen-specific human monoclonal antibodies from in vitro-primed human splenocytes" 1991, J Immunol vol. 147 pp. 86-95.
"Bourke et al., 2003, J. Immunol. vol. 170 pp. 5999 IL-1 Scavenging by the Type II IL-1 Decoy Receptor inHuman Neutrophils1".
Brennan et al., "Preparation of bispecific antibodies by chemical recombination of monoclonal immunoglobulin G1 fragments" Science. Jul. 5, 1985;229(4708):81-3.
Brockes, et al. "Appendage regeneration in adult vertebrates and implications for regenerative medicine" 2005, Science vol. 310 pp. 1919-1923.
Brunschwig et al. "Host Resistance to Cancer" 1965 Annals of Surgery vol. 162 No. 3 pp. 416-425.
Buess et al., "STRAP is a strong predictive marker of adjuvant chemotherapy benefit in colorectal cancer"Neoplasia. Nov.-Dec. 2004;6(6):813-20.
Smith, et al. "Constitutive Expression of a Truncated INT3 Gene in Mouse Mammary Epithelium Impairs Differentiation and Functional Development," Cell Growth Differ. 6:563-577, the American Association for Cancer Research, Philadelphia, PA, U.S.A. (1995).
Song et al., "Cancer stem cells—an old idea that's new again: implication for the diagnosis and treatement of breast cancer," Expert Opin Biol Ther 7(4): 431-438, 2007.
Soriano JV et al.,"Expression of an Activated NOTCH4(int-3) Oncoprotein Disrupts Morphogenesis and Induces an Invasive Phenotype in Mammary Epithelial Cells in Vitro" Int. J. Cancer, vol. 86, pp. 652-659 (2000).
Sørlie, et al. "Truncating somatic mutation in exon 15 oltheAPC gene Is a rare event in human breast carcinomas" Mutations in brief No. 179. Online. Hum Mutat12, 215 (1998).
Southam, C.; Brunschwig, A.: 'Quantitative studies of autotransplantation of human cancer' Cancer vol. 14, 1961, pp. 971-978.
Spangrude, G. J.; Heimfeld, S.; Weissman, I. L.: 'Purification and characterization of mouse hematopoietic stem cells' Science vol. 241, 1988, pp. 58-62.
Spink, et al. "Structural basis of the Axinadenomatopolyposis coli interaction" EMBO J 19, 2270-9 (2000).
Stewart et al. "Expression of retroviral vectors in transgenic mice obtained by embryo infection" EMBO J. vol. 6, 1987, p. 383-8.
Sugaya, et al., "Gene organization of human NOTCH4 and (CTG)n polymorphism in this human counterpart gene of mouse proto-oncogene Int3" Gene 189: 235-244 (1997).
Sugimoto, A. et al., "Delta-4 Notch ligand promotes erythroid differentiation of human umbilical cord blood CD34+ cells," Exp. Hematol. 34:424-432 (Apr. 2006).
Suzuki, T., et al., "Imbalanced expression of TAN-1 and human Notch4 in endometrial cancers," Int. J. Oncol. 17:1131-1139, Spandidos Publications Ltd., Athens, Greece (2000).
Syrigos, K.N. and Epenetos, A.A., "Antibody Directed Enzyme Prodrug Therapy (ADEPT): A Review of the Experimental and Clinical Considerations," Anticancer Res., 19:606-614 (1999).
Szabo et al. "Surface plasmon resonance and its use in biomolecular interaction analysis (BIA)" Curr. Opin. Struct. Biol. vol. 5, 1995, pp. 699-705.
Taber's Cyclopedic Medical Dictionary (1985, F.A. Davis Company, Philadelphia, p. 274).
Taipale, et al. "The Hedgehog and Wnt Signalling Pathways in Cancer" Nature, 411, 349-54 (2001).
Takahashi et al. "Sulindac Sulfide Is a Noncompetitive γ-Secretase Inhibitor That Preferentially Reduces Aβ42 Generation" J of Biological Chemistry, 2003, 287: 18664-18670.
Takeuchi et al, "Expression of CD44 variant exons 8-10 in colorectal cancer and its relationship to metastasis" Jpn J Cancer Res, 1995, vol. 86; pp. 292-297.
Tannock and Hill, "The Basic Science of Oncology," 1998, New York: McGraw-Hill, pp. 357-358.

Tax, et al. "Sequence of *C. elegans* lag-2 reveals a cell-signalling domain shared with Delta and Serrate of Drosophila" Nature 1994;368:150-4.
Terskikh AV et al., From hematopoiesis to neuropoiesis: Evidence of overlapping genetic programs, Proc Natl Acad Sci USA (Jul. 3, 2001) 98 (14): 7934-7939.
Thampoe et al., "Biochemical analysis of a human epithelial surface antigen: differential cell expression and processing," Arch Biochem Biophys 1988, 267: 342-52.
Thelu J et al., "Notch signaling is linked to epidermal cell differentiation level in basal cell carcinoma psoriasis & wound healing," BMC Dermatol (Apr. 29, 2002) 2(1): 7.
Thorner and Vance, "Growth Hormone," J. Clin. Invest., 82: 745 (1988).
Thorpe et al. "Improved antitumor effects of immunotoxins prepared with deglycosylated ricin A-chain and hindered disulfide linkages" Cancer Res. vol. 48, 1988, p. 6396-6403.
Tockman et al. "Considerations in bringing a cancer biomarker to clinical application" Cancer Res. 1992, 52: 2711s-2718s.
Togayachi et al, "Molecular Cloning and Characterization of UDO-GlcNac: Lactosylceramide 1, 3 N-Acetylglucosaminyltransferase . . . ." J Biol Chem vol. 276, pp. 22032-22040 (2001).
Townsend et al "The transporters associates with antigen presentation" Seminars in Cell Biology, vol. 4, pp. 53-61 (1993).
Trainer et al., Treatment of acromegaly with the growth hormone-receptor antagonist pegvisomant, N. Engl. J. Med. 2000; 342:1171-1177.
Tricot, G. et al.: 'Collection, tumor contamination, and engraftment kinetics of highly purified hematopoietic progenitor cells to support high dose therapy in multiple myeloma' Blood vol. 91, 1998, pp. 4489-4495.
Tsukamoto, et al. "Expression of the int-1 gene in transgenic mice Is associated with mammary gland hyperplasia and adenocarcinomas in male and female mice" Cell, vol. 55, p. 619-25 (1988).
Tuschl, et al. "Small Interfering RNAs: A Revolutionary Tool for the Analysis of Gene Function and Gene Therapy" Molecular Intervent. vol. 2, No. 3, 2002, pp. 158-167.
Uchida, N. et al.: 'Direct isolation of human central nervosystem stem cells' Proceedings of the National Academy of Sciences vol. 97, 2000, pp. 14720-14725.
Üren et al, "Secreted Frizzled related Protein 1 Binds Directly to Wingless and Is a Biphasic Modulator of Wnt Signalling" J Biol Chem, vol. 275, pp. 4374-4382 (2000).
Uyttendaele, H., et al., "Notch4 and Wnt-1 Proteins Function to Regulate Branching Morphogeneses of Mammary Epithelial Cells in an Opposing Fashion" Dev. Biol. 196-204-217, Elsevier Inc., Amsterdam, The Netherlands (1998).
Van De Vijver et al, "A gene-expression signature as a predictor of survival in breast cancer" n. Eng. J Med vol. 347, pp. 1999-2009 (2002).
van de Wetering, et al. "The beta-cateninfTCF-4 complex imposes a crypt progenitor phenotype on colorectal cancer cells" Cell 111, 241-50 (2002).
Van Den Berg,et al. "Role of Members of the Wnt Gene Family in Human Hematopoiesis" Blood, vol. 92, pp. 3189-3202 (1998).
Van Der Lugt, N. M. et al, "Posterior transformation, neurological abnormalities, and severe hematopoietic defects in mice with a targeted deletion of the bmi-1 proto-oncogene" Genes and Development 8, 757-769 (1994).
Van Es, et al. "Notch and Wnt inhibitors as potential new drugs for intestinal neoplastic disease," Trends Mol. Med. 11:496-502, Elsevier Inc., Amsterdam, The Netherlands (2005).
Van Es, et al. "Notch/gamma secretase inhibition turns proliferative cells in intestinal crypts and adenomas into goblet cells" Nature 435: 959-963, 2005.
Van Limpt, V., et al., "SAGE Analysis of Neuroblastoma Reveals a High Expression of the Human Homologue of the Drosophila Delta Gene," Med. Pediatr. Oncol. 35:554-558, Wiley-Liss, Inc., Massachusetts, U.S.A (2000).
Van Lohuizen, M. et al., "Sequence Similarity Between the Mammalian bmi-1 Ptoto-Oncogene and the Drosophila regulatory Genes Psc and Su (z)2." Nature 353-355 (1991).

Van Doyen & Nusse, "Structure and nucleotide sequence of the putative mammary oncogene int-1; proviral insertions leave the protein-encoding domain intact" 1984, Cell 39: 233-40.

Vanderlely, "The Future of Growth Hormone Antagonists." 2002, CurrOpinPharm. vol. 2 pp. 730-733.

Van'T Veer et al. "Gene expression profiling predicts clinical outcome of breast cancer" nature, vol. 415, pp. 530-636 (2002).

Varnum-Finney, B. et al. Pluripotent, cytokine-dependent, hematopoietic stem cells are immortalized by constitutive Notch1 signaling. Nat Med 6, 1278-81 (2000).

Vestey et al, "Immunohistochemical expression of insulin-like growth factor binding protein 3 in invasive breast cancers and ductal carcinoma in situ: implications for clincopathology and patient outcome" Breast Cancer Res., vol. 7, pp. R119-R129 (2005).

Visonneau S et al, Cell Therapy of a Highly Invasive Human Breast Carcinoma Implanted in Immunodeficient (SCID) Mice, Clinical Cancer Research (Sep. 1997) 3: 1491-1500.

Voena, C. et al.: 'Qualitative and quantitative polymerase chain reaction detection of the residual myeloma cell contamination after positive selection of CD34+ cells with small- and large-scale Miltenyi cell sorting system' Br J Haematol vol. 117, 2002, pp. 642-645.

Von Hoff DD et al. "A Southwest Oncology Group Study on the Use of a Human Tumor Cloning Assay for Predicting Response in Patients With Ovarian Cancer," Cancer(Jan. 1, 1991) 67(1): 20-7.

Gridley, "Notch signaling in vertebrate development and disease." Mol Cell Neurosci. 1997;9(2):103-8.

Groisman et al., "Fibroblastic polyp of the colon: clinicopathological analysis of 10 cases with emphasis on its common association with serrated crypts." Histopathology. Mar. 2006;48(4):431-7.

Gruber et al., "Efficient tumor cell lysis mediated by a bispecific single chain antibody expressed in *Escherichia coli*." J Immunol. Jun. 1, 1994;152(11):5368-74.

Hahn et al., "DPC4, a candidate tumor suppressor gene at human chromosome 18q21.1." Science. Jan. 19, 1996;271 (5247):350-3.

Halder et al., "Oncogenic function of a novel WD-domain protein, STRAP, in human carcinogenesis." Cancer Res. Jun. 15, 2006;66(12):6156-66.

Hamacher et al.,"[Extracellular matrix—from basic research to clinical significance. An overview with special consideration of matrix metalloproteinases]" Dtsch Med Wochenschr. Sep. 17, 2004;129(38):1976-80.

Harada, et al. "Intestinal polyposis in mice with a dominant stable mutation of the beta-catenin gene" 1999, EMBO J vol. 18, pp. 5931-5942.

Hardingham et al., "Cartilage, SOX9 and Notch signals in chondrogenesis." J Anat. Oct. 2006;209(4):469-80.

Hatsell et al., "Beta-catenin and Tcfs in mammary development and cancer." J Mammary Gland Biol Neoplasia. Apr. 2003;8(2):145-58.

He et al., "Cellular and molecular regulation of hematopoietic and intestinal stem cell behavior." Ann N Y Acad Sci. May 2005;1049:28-38.

Helms et al., "First evidence supporting a potential role for the BMP/SMAD pathway in the progression of oestrogen receptor-positive breast cancer" J Pathol. Jul. 2005;206(3):366-76.

Hernandez-Alcoceba et al., "A novel, conditionally replicative adenovirus for the treatment of breast cancer that allows controlled replication of E1a-deleted adenoviral vectors." Hum Gene Ther. Sep. 20, 2000;11(14):2009-24.

Hillier et al., 1996, GenResvol. 6pp. 807-828 Generation and Analysis of 280,000 Human Expressed Sequence Tags.

Hitoshi et al., "Notch pathway molecules are essential for the maintenance, but not the generation, of mammalian neural stem cells." Genes Dev. Apr. 1, 2002;16(7):846-58.

Hoffman, 1999, Invest New Drugs vol. 17pp. 343-359 Orthotopic metastatic mouse models for anticancer drug discovery and evaluation: a bridge to the clinic.

Hong et al., 2001, genesis vol. 29 pp. 163-171 The winged helixlforkhead transcription factor Foxq1 regulates differentiation of hair in satin mice.

Hoogenboom, et al. "By-passing immunisation. Human antibodies from synthetic repertoires of germline VH gene segments rearranged in vitro." J Mol Biol. Sep. 20, 1992;227(2):381-8.

Howe et al. "Germline mutations of the gene encoding bone morphogenetic protein receptor 1A in juvenile polyposis" Nat Genet. Jun. 2001;28(2):184-7.

Howe et al. "Mutations in the SMAD4/DPC4 gene in juvenile polyposis" Science. May 15, 1998;280(5366):1086-8.

Huber et al., "Molecular requirements for epithelial-mesenchymal transition during tumor progression." Curr Opin Cell Biol. Oct. 2005;17(5):548-58.

Hughes et al., 2002. Mol Ther. vol. 5 pp. 16-24 Viral-Mediated Gene Transfer to Mouse Primary Neural Progenitor Cells.

Huusko et al., "Nonsense-mediated decay microarray analysis identifies mutations of EPHB2 in human prostate cancer" Nat Genet. Sep. 2004;36(9):979-83.

Ide et al., "Growth regulation of human prostate cancer cells by bone morphogenetic protein-2." Cancer Res. Nov. 15, 1997;57(22):5022-7.

Ikeda et al., 1993, Exp. Hematol vol. 21 pp. 1686-1694 Changes in phenotype and proliferative potential of human acute myeloblastic leukemia cells in culture with stem cell factor.

Ikeyama et al., "Suppression of cell motility and metastasis by transfection with human motility-related protein (MRP-1/CD9) DNA." J Exp Med. May 1, 1993;177(5):1231-7.

Ilantzis et al., "Deregulated expression of the human tumor marker CEA and CEA family member CEACAM6 disrupts tissue architecture and blocks colonocyte differentiation." Neoplasia. Mar.-Apr. 2002;4(2):151-63.

Imbert et al., "Delta N89 beta-catenin induces precocious development, differentiation, and neoplasia in mammary gland." J Cell Biol. Apr. 30, 2001;153(3):555-68.

Itoh et al., "Signaling of transforming growth factor-beta family members through Smad proteins." Eur J Biochem. Dec. 2000;267(24):6954-67.

Izumi et al., "Bone morphogenetic protein-2 inhibits serum deprivation-induced apoptosis of neonatal cardiac myocytes through activation of the Smad1 pathway." J Biol Chem. Aug. 17, 2001;276(33):31133-41.

Jantscheff et al., "Expression of CEACAM6 in resectable colorectal cancer: a factor of independent prognostic significance." J Clin Oncol. Oct. 1, 2003;21(19):3638-46.

Jarriault et al., "Delta-1 activation of notch-1 signaling results in HES-1 transactivation." Mol Cell Biol. Dec. 1998;18 (12):7423-31.

Jemal et al., "Cancer statistics, 2003." CA Cancer J Clin. Jan.-Feb. 2003:53(1):5-26.

Johnson et al., "LRP5 and Wnt signaling: a union made for bone." J Bone Miner Res. Nov. 2004;19(11):1749-57. Epub Aug. 23, 2004.

Jones et al., "Replacing the complementarity-determining regions in a human antibody with those from a mouse." Nature. May 29-Jun. 4, 1986;321(6069):522-5.

Joutel, et al. "Notch signalling pathway and human diseases." Semin Cell Dev Biol. Dec. 1998;9(6):619-25.

Karanu et al., "The notch ligand jagged-1 represents a novel growth factor of human hematopoietic stem cells." J Exp Med. Nov. 6, 2000;192(9):1365-72.

Kastan et al., "Direct demonstration of elevated aldehyde dehydrogenase in human hematopoietic progenitor cells." Blood. May 15, 1990;75(10):1947-50.

Kataoka et al., "Expression profile of EFNB1, EFNB2, two ligands of EPHB2 in human gastric cancer." J Cancer Res Clin Oncol. Jul. 2002;128(7):343-8.

Katoh, "Epithelial-mesenchymal transition in gastric cancer (Review)" Int J Oncol. Dec. 2005;27(6):1677-83.

Kawano & Kypta, 2003, J Cell Sci. vol. 116 pp. 2527-2534 Secreted antagonists of the Wnt signalling pathway.

"Keane et al., 2001, Am. J. respir. Crit. Care Med. vol. 164 pp. 2239 ENA-78 Is an Important Angiogenic Factor in IdiopathicPulmonary Fibrosis".

Kidd et al., "Sequence of the notch locus of *Drosophila melanogaster*: relationship of the encoded protein to mammalian clotting and growth factors." Mol Cell Biol. Sep. 1986;6(9):3094-108.

Kim, et al. "The multidrug resistance transporter ABCG2 (breast cancer resistance protein 1) effluxes Hoechst 33342 and is overexpressed in hematopoietic stem cells." Clin Cancer Res. Jan. 2002;8(1):22-8.

Kleeff et al., "Bone morphogenetic protein 2 exerts diverse effects on cell growth in vitro and is expressed in human pancreatic cancer in vivo"Gastroenterology. May 1999;116(5):1202-16.

Klein, "Eph/ephrin signaling in morphogenesis, neural development and plasticity." Curr Opin Cell Biol. Oct. 2004;16 (5):580-9.

Knutson et al., 2005, "Augmenting T helper cell immunity in cancer." Curr Drug Targets Immune Endocr Metabol Disord. Dec. 2005;5(4):365-71.

Kobayashi et al., "Sox9 in testis determination." Ann N Y Acad Sci. Dec. 2005;1061:9-17.

Kodera et al., "Expression of carcinoembryonic antigen (CEA) and nonspecific crossreacting antigen (NCA) in gastrointestinal cancer; the correlation with degree of differentiation." Br J Cancer. Jul. 1993;68(1):130-6.

Kokko et al., "EPHB2 germline variants in patients with colorectal cancer or hyperplastic polyposis." BMC Cancer. Jun. 1, 2006;6:145.

Korinek, V. et al. Depletion of epithelial stem-cell compartments in the small intestine of mice lacking Tcf-4. Nat Genet 19, 379-83 (1998).

Miller et al. "Mechanism and function of signal transduction by the Wnt/β-catenin and Wnt/Ca2+ pathways" 1999, Oncogene 18: 7860-72.

Miller, C. L.; Eaves, C. J.: 'Expansion in vitro of adult murine hematopoietic stem cells with transplantable lympho-myeloid reconstituting ability' Proc Natl Acad Sci USA vol. 94, 1997, pp. 13648-13653.

Mills et al., "The emerging role of lysophosphatidic acid in cancer" Nat Rev Cancer, vol. 3, pp. 582-591 (2003).

Mitchell et al, "A Novel Melanoma Gene (MG50) Encoding the Interleukin 1 Receptor Antagonist and Six Epitopes Recognized by Human Cytolytic T Lymphocytes," Cancer Reearch vol. 60, pp. 6448-6456 (2000).

Morrison, et al. "Hematopoietic stem cells: challenges to expectations" Curr Opinion Immunol (1997) 9(2): 216-21.

Morrison, et al. Prospective identification, isolation by flow cytometry and in viv self-renewal of multipotent mammalian neural crest stem cells: Cell, 96 (5) 737-49 (1999).

Morrison, et al. "Regulatory Mechanisms in Stem Cell Biology," Cell (Feb. 7, 1997) 88(3): 287-98.

Morrison, et al. "The long-Term Repopulating Subset of Hematopoietic Stem Cells Is Detenninistic and Isolatable by Phenotype," Immunity (Nov. 1994) 1(8): 661-73.

Morrison, et al. "Transient Notch Activation Initiates an Irreversible Switch from Neurogenesis to Gliogenesis by Neural Crest Stem Cells," Cell (May 26, 2000) 101(5): 499-510.

Morrison, et al. 'A Genetic Determinant That Specifically Regulates the Frequency of Hematopoietic Stem Cells' J. Immunol. vol. 168, 2002, pp. 635-642.

Morrison, et al. 'Identification of a lineage of multipotent hematopoietic progenitors' Development vol. 124, 1997, pp. 1929-1939.

Morrison, et al. 'Telomerase activity in hematopoietic cells is associated with self-renewal potential' Immunity vol. 5, 1996, pp. 207-216.

Morrison, et al. 'The Purification and Characterization of Fetal Liver Hematopoietic Stem Cells' Proc. Natl. Acad. Sci. USA vol. 92, 1995, pp. 10302-10306.

Mott et al, "Regulation of matrix biology by matrix metalloproteinases" Current Opinion Cell Biology vol. 16, pp. 558-564 (2004).

Mueller & Reisfeld, "Potential of the scid mouse as a host for human tumors," Cancer Metastasis Rev. (1991) 10: 193-200.

Muller-Sieburg, C. E. et al.: 'Genetic control of hematopoietic stem cell frequency in mice is mostly cell autonomous' Blood vol. 95, 2000, pp. 2446-2448.

Murdoch et al, "Wnt-5A augments repopulating capacity and primitive hematopoietic development of human blood stem cells in vivo" 2003, PNAS 100: 3422-7.

Nam et al. Notch signaling as a therapeutic target. Curr Opion Chem Biol 6: 501-509, 2002.

Nam, et al. "Structural requirements for assembly of the CSL. intracellular Notch1.Mastermind-like 1 transcriptional activation complex" J Biol Chem 278, 21232-9 (2003).

Naor, et al., "CD44 in cancer" Crit Rev Clin Lab Sci 39(6): 527-579 (2002).

Natarajan et al, "Sturcture and Function of Natural Killer Cell Receptors" Annu Rev. Immunol. vol. 20, pp. 853-885 (2002).

Negrin, et al.: 'Transplantation of highly purified CD34+Thy-l+ hematopoietic stem cells in patients with metastatic breast cancer' Biol Blood Marrow Transplant vol. 6, 2000, pp. 262-271.

Nie et al, "A Novel PTB-PDZ Domain Interaction Mediates Isoform-specific Ubiquitylation of Mammalian Numb" J Biol. Chem. vol. 279, pp. 20807-20815 (2004).

Nie, et al, "LNX functions as a RING type E3 ubiquitin ligase that targets the cell fate determinate Numb for ubiquitin-dependent degradation," EMBO J. vol. 21, pp. 93-102 (2002).

Nielsen et al."Sequence-selective recognition of DNA by strand displacement with a thymine-substituted polyamid" Science vol. 254, 1991, p. 1497.

Nierodzik et al, Protease-Activated Receptor I (PAR-I) Is Required and Rate-Limiting for Thrombin-Enhanced Experimental Pulmonary Metastasis, Blood 1998; 92: 3694-3700.

Noguera-Troise, et al. "Blockade of Dll4 inhibits tumour growth by promoting non-productive angiogenesis," Nature 444:1032-1037, Nature Publishing Group, New York, NY, U.S.A. (2006).

Nusse "The Wnt gene family in tumorigenesis and in normal development" Journal of Steroid Biochemistry & Molecular Biology 43,9-12 (1992).

Nusse R et al, "Mode of proviral activation of a putative mammary oncogene (int-1) on mouse chromosome 15" Nature, 307: 131-6 (1984).

Nusse, R. & Varrnus, H. E. "Many tumors induced by the mouse mammary tumor vircontain a provirintegrated in the same region of the host genome" Cell 31, 99-109 (1982).

Nusse, R. et al. "A new nomenclature for int-1 and related genes: the Wnt gene family" Cell 64, 231 (1991).

Ogawa M et al., "Studies of Nitrogen Mustard Transport by Mouse Myeloma and Hemopoietic Precursor Cells," Cancer Research (Dec. 1973) (33)12: 3172-3175.

Ogawa, et al. "Differential Effects of Melphalan on Mouse Myeloma (Adj. PC-5) and Hemopoietic Stem Cells," Cancer Research (Dec. 1971) 31(12): 2116-2119.

Ogoshi, et al., CD44H Participates in the Intrahepatic Growth of Murine Colon 26 Adenocarcinoma Cells, Jpn J. Cancer Res 1998:89: 1160-8.

Osanai et al, "Expression and characterization of Rab38, a new member of the Rab small G protein family," Biol Chem vol. 386, pp. 143-153 (2005).

Osawa, M. et al.: 'Long-term lymphohematopoietic reconstitution by a single CD34-low/negative hematopoietic stem cell' Science vol. 273, 1996, pp. 242-245.

Packeisen et al, "Detection of Surface Antigen 17-1A in breast and Colorectal Cancer" Hybridoma, vol. 18, pp. 37-40 (1999).

Pandis et al., Cytogenetic Comparison of Primary Tumors and Lymph Node Metastase in Breast Cancer Patients, Genes, Chromosomes & Cancer (1998) 12: 122-129.

Pantschenko et al, "The interleukin-1 family of cytokines and receptors in human breast cancer: Implications for tumor progression" Int. J Oncology, vol. 23, pp. 269-284 (2003).

Park, C. H.; Bergsagel, D. E.; McCulloch, E. A.: 'Mouse myeloma tumor stem cells: a primary cell culture assay' J Natl Cancer Inst vol. 46, 1971, pp. 411-422.

Parks, A.L., et al., "Structure-Function Analysis of Delta Trafficking, Receptor Binding and Signaling in Drosophila," Genetics 174:1947-1961, The Genetics Society of America (2006).

Parr, C., et al., "The possible correlation of Notch-1 and Notch-2 with clinical outcome and tumour clinicopathological parameters in human breast cancer," Int. J. Mol. Med. 14:779-786, Spandidos Publications Ltd., Athens, Greece (2004).

Patel et al., "Generation of Intedeukin-2-Secrcting Melanoma Cell Populations from Resected Metastatic Tumors," Human Gene Therapy (1994) 5: 577-584.
Patel, N.S., et al., "Up-regulation of Delta-like 4 Ligand in Human Tumor Vasculature and the Role of Basal Expression in Endothelial Cell Function," Cancer Res. 65:8690-8697, The American Association for Cancer Research (2005).
Paul et al, "Effective expression of small interfering RNA in human cells" nature Biotech, vol. 29, pp. 505-508 (2002).
Pear, W.S. and Aster, J.C., "Tcell acute lymphoblastic leukemia/lymphoma: a human cancer commonly associated with aberrant NOTCH1 signaling," Curro Opin. Hematol. 11:426-433, Lippincott Williams & Wilkins, Philadelphia, PA, U.S.A. (2004).
Petcherski, et al. "Mastermind is a putative activator for Notch" Curr Biol 10, R471-3 (2000).
Phillips, et al. 'Genetic control of murine hematopoietic stem cell pool sizes and cycling kinetics' Proc Natl Acad Sci U SA vol. 89, 1992, pp. 11607-11611.
Pold et al, "Cyclooxygenase 2-Dependent Expression of Angionenic CXC Chemokins ENA-78/CXC Ligand (CXCL) 5 and Interleukin-8/CXCL8 in Human Non-Small Lung Cancer" Cancer Res vol. 64, pp. 1853-1860 (2004).
Politi, et al. "Notch in mammary gland development and breast cancer," Semin. Cancer Biol. 14:341-347, Elsevier Inc., Amsterdam, The Netherlands (2004).
Hnatowich et al., "The preparation and labeling of DTPA-coupled albumin" Int. J Appl. Radiat. lot. vol. 33, 1982, p. 327-32.
Hogan et al.: 'Manipulating the Mouse Embryo', 1986, Cold Spring Harbor Laboratory Press.
Holen et al. "Positional effects of short interfering RNAs targeting the human coagulation trigger Tissue Factor" Nucleic Acids Res. vol. 30, 2002, pp. 1757-1766.
Hope, K.J., et al., "Acute myeloid leukemia originates from a hierarchy of leukemic stem cell classes that differ in self-renewal capacity," Nat. Immunol. 5:738-43, Nature Publishing Group, New York, NY, U.S.A. (2004).
Hopfer, et al. "The Notch pathway in ovarian carcinomas and adenomas" British Journal of Cancer, vol. 93, pp. 709-718 (2005).
Houghten "The use of synthetic peptide combinatorial libraries for the identification of bioactive peptides" Biotechniques vol. 13, 1992, pp. 412-421.
Howes et al, "Cationic Trypsingen Mutations and Pancreatitis" Clin Lab Med, vol. 25, pp. 39-59 (2005).
Hughes and Friesen, "The Nature and Regulation of the Receptors for the Pituitary Growth Horman," Annu. Rev. Physiol. 47: 469 (1985).
Ilyas "Wnt signalling and the mechanistic basis of tumour development" J Pathology, vol. 205, pp. 130-144 (2005).
Imatani, A. & Callahan, R. Identification of a novel NOTCH-4/INT-3 RNA species encoding an activated gene product in certain human tumor cell lines. Oncogene 19,223-231 (2000).
Isaksson et al., "Mode of Action of Pituitary Growth Hormone on Target Cells," Annu. Rev. Physiol. 47: 483 (1985).
Ishiko, E., et al., "Notch Signals Inhibit the Development of Erythroid/Megakaryocytic Cells by Suppressing GATA-1 Activity through Induction of HES1," J. Biol. Chem. 280:4929-4939, The American Society for Biochemistry and Molecular Biology, Inc. (2005).
Iso, T., et al., "Notch Signaling in Vascular Development," Arterioscler. Thromb. Vasco Biol. 23:543-553, Lippincott Williams & Wilkins, Philadelphia, PA, U.S.A. (2003).
Iwabuchi et al. "Use of the two-hybrid system to identify the domain of p53 involved in oligomerization" Oncogene vol. 8, 1993, pp. 1693-1696.
Jaattela, et al. "Bcl-x and Bcl-2 inhibit TNF and Fas-induced apoptosis and activation of phospholipase A2 in breast carcinoma cells" Oncogene 10(12) pp. 2297-2305 (1995).
Jaenisch "Germ line integration and Mendelian transmission of the exogenous Moloney leukemia virus" Proc. Natl. Acad. Sci. USA vol. 73, 1976, p. 1260-4.
Jaenisch "Transgenic animals" Science vol. 240, 1988, p. 1468-74.
Jahner et al. "Insertion of the bacterial gpt gene into the germ line of mice by retroviral infection" Proc. Natl. Acad Sci. USA vol. 82, 1985, p. 6927-31.
Jahner et al. "De novo methylation and expression of retroviral genomes during mouse embryogenesis" Nature vol. 298, 1982, p. 623-8.
Janeway, Jr. et al., Immunobiology, The Immune System in Health and Disease, 4th Ed., Current Biology Publications; Appendix L, pp. 579-581 (1999).
Janke J et al: "Suppression of Tumorigenicity in Breast Cancer Cells by the Microfilament Protein Profilin 1" Journal of Experimental Medicine, May 15, 2000, pp. 1675-1685, vol. 191, No. 10, Tokyo, JP.
Jarriault, et al. "Signalling downstream of activated mammalian Notch," Nature 377:355-358, Nature Publishing.
Jeffries et al., Neoplastic Transformation by Notch Requires Nuclear Localization, Mol Cell Bio Jun. 2000; 20: 3928-41.
Jehn, et al. "Cutting edge: protective effects of notch-1 on TCR-induced apoptosis" J Immunol., 162(2):635-8 (1999).
Jette et al, "The Tumor Supressor Adenomatous Polyposis Coli and Caudal Related Homeodomain Protein Regulate Expression of Retinol Gehydrohenase L" J. Biol Chem vol. 279, pp. 34397-34405 (2004).
Jhappan, et al. "Expression of an activated Notch-related int-3 transgene interferes with cell differentiation and induces neoplastic and salviary glands," Genes & Dev. 6:345-355, Cold Spring Harbor Laboratory Press, Woodbury NY, U.S.A. (1992).
Ji, et al. "Comprehensive analysis of the gene expression profiles in human gastric cancer cell lines" Oncogene, 2002, 21:6549-6556.
Jiang et al., "Smooth muscle tissues express a major dominant negative splice variant of the type 3 Ca2+ release channel (ryanodine receptor)" J. Biol. Chem. 2003 vol. 278(7) pp. 4763-4769.
Jones et al, "Development of a bioassay for putative human lymphoma stem cells" Blood. Feb. 1979;53(2):294-303.
Jones, P., et al. (1998) "Stromal Expression of Jagged 1 promotes colony formation by fetal hematopoietic progenitor cells" Blood, 92, pp. 1505-1511 (1998).
Jonsson, M., Borg, A., Nilbert, M. & Andersson, T. Involvement of adenomatopolyposis coli (APC)/beta-catenin signalling in human br~ast cancer. Eur J Cancer 36, 242-8 (2000).
Kadowaki et al. "Reg protein is overexpressed in gastric cancer cells, where it activates a signal transduction pathway that converges on ERK1/2 to stimulate growth" FEBS Letters, 2002, 530: 59-64.
Kaiser "Cancer. First pass at cancer genome reveals complex landscape" Science, 2006, 313: 1370.
Katsetos, et al. "Localization of the neuronal class Iii beta-tubulin in oligodendrogliomas: comparison with Ki-67 Proliferative Index and 1p/19q Status," J Neuropathol Exp. Neurol. 2002, 61, 307-320.
Kaulsay, et al., "The effects of autocrine human growth hormone (hGH) on human mammary carcinoma cell behavior are mediated via the hGH rceptor," Endocrinology, 2001, vol. 142, pp. 767-777.
Kern, et al "The Fuzzy Math of Solid Tumor Stem Cells: A Perspective," Cancer Research, Oct. 1, 2007, pp. 8985-8988, vol. 67 (19).
Khaw et al., "Myocardial infarct imaging of antibodies to canine cardiac myosin with indium-111-diethylenetriamine pentaacetic acid" Science vol. 209, 1980, p. 295.
Kim et al, "Methylation and expression of p16INK4 tumor supressor gene in primary colorectal Carcnimoas" Int J. Oncol. vol. 26, pp. 1217-1226 (2005).
Kirikoshi et al, "Expression of WNT10A in human cancer," Int J Oncology vol. 19, pp. 997-1001 (2001).
Kobielak et al, "alpha-Catenin: at the junction of intecelullar adhesion and actin dynamics" nat Rev Mol Cell Biol. vol. 5, pp. 614-625 (2004).
Kobuke et al, ESDN a Novel Neuropilin-like Membrane Protein Clonsed from Vascular Cells with the Longest Secretory Signal Sequence among Eukaryotes . . . J Biol Chem Bol. 276, pp. 34105-34114 (2001).
Köhler, et al. "Continuous cultures of fused cells secreting antibody of predefined specificity" Nature vol. 256, 1975, p. 495-7.
Kondo et al., "Persistence of a small subpopulation of cancer stem-like cells in the (6 glioma cell line," PNAS 2004, 101 (3), 781-786.
Kondo, Cellular localization of CD44 correlates with cell proliferation and liver metastasis in colon cancer, 1999, Int J Clin Oncol 4: 78-83.
Kopper, L. and Hajdu, M., "Tumor Stem Cells," Pathol. Oncol. Res. 10:69-73, Aranyl Lajos Foundation, Budapest, Hungary (2004).

Kordon & Smith, "An entire functional mammary gland may comprise th progeny from a single cell," Development (Apr. 22, 1998) 125: 1921-1930.

Korinek, V. et al. Two members of the Tcf family implicated in WnUbeta-catenin signaling during embryogenesis in the mouse. Mol Cell Biol 18, 1248-56 (1998).

Koshikawa et al, "Significant up -regulation of novel gene, CLCP1, in a highly metastatic lung cancer subline as well as in lung cancers in vivo" Oncogene, vol. 21, pp. 2822-2828 (2002).

Krasna, L. et al. Large expansion of morphologically heterogeneomammary epithelial cells, including the luminal phenotype, from human breast tumours. Breast Cancer Res Treat 71.219-35 (2002).

Krebs, Lt., et al., "Haploinsufficient lethality and formation of arteriovenomalformations in Notch pathway mutants," Genes Dev. 18:2469-2473, Cold Spring Harbor Laboratory Press (2004).

Vormoor, et al. "Establishment of an in Vivo Model for Pediatric Ewing Tumors by Transplantation into NOD/scid Mice" Pediatric Research, vol. 49, pp. 332-341.

Wagner, et al. "The insulin-like growth factor-1 pathway mediator genes: SHC1 Met300Val shows a protective effect in breast cancer" Carcinogenesis, vol. 25, pp. 2473-3478 (2004).

Wang, et al. "Primitive human hematopoeitic cells are enriched in cord blood compared with adult bone marrow or mobilized peripheral blood as measured by the quantitative in vivo SCID-repopulating cell assay" Blood 1997;89:3919-24.

Wang, et al., "Gene-expression profiles to predict distant metastasis of lymphnode negative primary breast cancer," Lancet vol. 365, pp. 671-679 (2005).

Webb, Journal of the National Cancer Institute, 95 (11): 774-775, Jun. 4, 2003, printed online, pp. 1-5.

Weeraratna, et al. "Wnt5a signaling directly affects cells motility and invasion of metastatic melanoma," Cancer Cell, Cell Press, vol. 1, No. 3, Apr. 1, 2002, pp. 279-288.

Weijzen S., et al., "Activation of Notch-1 signaling maintains the neoplastic phenotype in human Ras-transformed cells,"Nat. Med. 8:979-986, Nature Publishing Group New York, NY, U.S.A (2002).

Weisenthal & Lippman "Clonogenic and Nonclonogenic in Vitro Chemosensitivity Assays," Cancer Treatment Reports, vol. 69, pp. 615-648 (1985).

Weissman 'Translating stem and progenitor cell biology to the clinic: barriers and opportunities' Science vol. 287, 2000, pp. 1442-1446.

Welm, et al: "Sca-1pos cells in 1-21 the mouse mammary gland represent an enriched progenitor cell population" Developmental Biology, May 1, 2002, pp. 42-56, vol. 245, No. 1.

Weng, et al. "Growth suppression of pre-T acute lymphoblastic leukemia cells by inhibition of notch signaling" Molecular and Cellular Biology, American Society for Microbiology, Washington, US, vol. 23, No. 2, Jan. 1, 2003 pp. 655-664.

Wharton et al., "Expression of neuronal markers in oligodendroglimas: am immunohistochemical study," 1998 Neropathol App. Nerobiol 24, 302-308.

White, et al., "Antibody-targeted immunotherapy for treatment of malignancy" Feb. 2001 , Ann Rev Med, 52:125-145.

Wielenga et al.. "Expression of CD44 in Apc and Tcf mutant mice implies regulation by the Wnt pathway" Am J Pathol 154(2): 515-523, 1999.

Willert et al, "Wnt proteins are lipid-modified and can act as stem cell growth factors" 2003, Nature 423: 448-52.

Williams, C.K., et al., "Up-regulation of the Notch ligand Delta-like 4 inhibits VEGF-induced endothelial cell function," Blood 107:931-939 (Feb. 2006).

Williams, et al. 2005, Am J Physiol Cell Physiol. vol. 288 pp. C494-C506 Caveolin-1 in oncogenic transformation, cancer, and metastasis.

Wilson, A. and Radtke, F., "Multiple functions of Notch signaling in self-renewing organs and cancer," FEBS Lett. 580:2860-2868, Elsevier, Inc. (2006).

Wodinsky, et al. 'Spleen colony studies of leukemia L1210.I. Growth kinetics of lymphocytic L1210 cells in vivo as determined by spleen colony assay' Cancer Chemother. Rep. vol. 51, 1967, pp. 415-421.

Wolf et al, "Neural antigens in oligodendrogliomas and dysembryoplastic neuroepithelial tumors," Acta Neuropathol. 1997, 94, 436-443.

Wolff et al, "Early operable breast cancer" Current Treatment Options in Oncology. 2000, 1: 210-220.

Wong, S. C. et al. "Expression of frizzled-related protein and Wnt-signalling molecules in invasive human breast tumours" J Pathol196, 145-53 (2002).

Woodruff, "Cellular heterogeneity in tumours," Br J. Cancer 1983, 47, 589-594.

Wu, et al. "Identification of a family of mastermind-like transcriptional coactivators for mammalian notch receptors" Mol Cell Biol 22, 7688-700 (2002).

Wu, et al., "RGS proteins inhibit Xwnt-8 signaling in Xenopembryonic development" Development vol., 127, pp. 2773-2784 (2000).

Yakar, et al., "The role of growth hormone/insulin-like growth factor axis in tumor growth and progression: Lessons from animal models,"Cytokine & Growth Factor Review. 2005, vol. 16, pp. 407-420.

Yamada, et al. "Receptor for Hyaluronan-mediated Motility and .Q)44 Expressions in Colon Cancer Assessed by Quantitative Analysis Using Real-time Reverse Transcriptase-Polymerase Chain Reaction," Jpn J Cancer Res 1999; 90: 987-92.

Yamasaki et al, "Cell cycle, protelysis and cancer" Curr Opin Cell Biol., vol. 16, pp. 623-628 (2004).

Yan, X.-Q., et al., "A novel Notch ligand, D1I4, induces T-celileukemiallymphoma when overexpressed in mice by retroviral-mediated gene transfer," Blood 98:3793-3799, the American Society of Hematology, Washington, DC, U.S.A. (2001).

Yantiss et al, "KOC (K Homology Domain Containing Protein Overexpression in Cancer)" Am J Drug Pathol vol. 29, pp. 188-195 (2005).

Yasui et al. "Combination of Tumor Necrosis Factor-α with Sulindac Augments Its Apoptotic Potential and Suppresses Tumor Growth of Human Carcinoma Cells in Nude Mice" Cancer, Mar. 2003; 97: 1412-20.

Yeh et al, "Antisense overexpression of BMAL2 enhances cell proliferation" Oncogene vol. 22, pp. 5306-5314 (2003).

Yukimasa et al "Enhanced expression of p46 Shc in the nucleand p52 Shc in the cytoplasm of human gastric cancer" Intl J Oncology, vol. 26, pp. 905-911 (2005).

Zagouras, P., et al., "Alterations in Notch signaling in neoplastic lesions of the human cervix," PNAS 92:6414-6418, the National Academy of Sciences, Washington, DC, U.S.A. (1995).

Zerangue et al, "ASCT-1 Is a Neutral Amino Acid Exchanger with Chloride Channel Activity" J Biol. Chem vol. 271, pp. 27991-37994 (1996).

Zervos et al. "Mxi1, a protein that specifically interacts with Max to bind Myc-Max recognition sites" Cell vol. 72, 1993, pp. 223-232.

Zhang X. et al "Estrogen receptor positivity in mammary tumors on Wnt-1 transgenic mice is influenced by collaborating oncogenic mutations" Oncogene, 24: 4220-31 (2005).

Zhou et al, "Expression Cloning of 2-5A-Dependent RNAaseL a uniquely Regulated Mediator of Interferon Action" Cell, vol. 72, pp. 753-765 (1993).

Zhu, et al., "beta-Catenin signaling modulatesproliferative potential of human epidermal keratinocytes independently of intracellular adhesion," Development vol. 126, pp. 2285-2298 (1999).

Zoller, "CD44: physiological expression of distinct isoforms as evidence for organ-specific metastasis formation" J Mol Med, 1995; 73: 425-38.

Zuckermann et al., "Discovery of nanomolar ligands for 7-transmembrane G-protein-coupled receptors from a diverse N-(substituted)glycine peptoid library" J Med Chem vol. 37, 1994, p. 2678-85.

Bergsagel, et al. "The Improvement of the Animal Tumor Model," Cancer Research, 29: 2334-2338 1969.

Axelson, H. "Notch signaling and cancer: emerging complexity." Seminars in Cancer Biology, 2004, 14:317-319.

Clarke et al., "Epigenetic Regulation of Normal and Cancer Stem Cells," Ann Ny Acad. Sci. 1044:90,2005.

Frank-Kamenetsky et al, "Small molecule modulators of Hedgehog signaling: identification and characterization of Smoothened agonsits and atagonists," J Biol Nov. 6, 2002; 1(2) 10.

Paladini et al, "Modulation of Hair Growth with Small Molecule Agonists of the Hedgehog Signalling Pathway," J Invest Dermatol. Oct. 2005, 125 (4) 638-46.

Al-Hajj et al, "Self-renewal and solid tumor stem cells" Oncogene 2004, 23: 7274.

Hu, et al. "Evidence for lack of enhanced hedgehog target gene exprtession in common extracutaneotumors" Cancer Research, Mar. 1, 2003, vol. 63, pp. 923-928.

King "Roughing up Smoothened: chemical modulators of hedgehog signaling" Journal of Biology Nov. 6, 2002, vol. 1, p. 8.

Schutte et al. "DPC4 gene in various tumor types" Cancer Res. Jun. 1, 1996;56(11):2527-30.

Seong et al. "Regulation of transforming growth factor-beta signaling and PDK1 kinase activity by physical interaction between PDK1 and serine-threonine kinase receptor-associated protein" J Biol Chem. Dec. 30, 2005;280 (52):42897-908.

Shalaby et al., "Development of humanized bispecific antibodies reactive with cytotoxic lymphocytes and tumor cells overexpressing the HER2 protooncogene." J Exp Med. Jan. 1, 1992;175(1):217-25.

Sheets et al., "Efficient construction of a large nonimmune phage antibody library: the production of high-affinity human single-chain antibodies to protein antigens." Proc Natl Acad Sci USA. May 26, 1998;95(11):6157-62.

Shelly et al., 1999, J. Cell Biochem vol. 73pp. 164-175 Notch-1 inhibits apoptosis in murine erythroleukemia cells and is necessary for differentiation induced by hybrid polar compounds.

Shen, "Decrypting the role of Cripto in tumorigenesis." J Clin Invest. Aug. 2003;112(4):500-2.

Shimizu et al., 1997, Cell Growth Diff. vol. 8. pp. 1349-1358Transformation by Wnt family proteins correlates with regulation of beta-catenin.

Shivdasani et al., 1995, Nature vol. 373 pp. 432-434 Absence of blood formation in mice lacking the T-cell leukaemia oncoprotein tal-1/SCL.

Shopes, "A genetically engineered human IgG mutant with enhanced cytolytic activity." J Immunol. 1992 May 1;148(9):2918-22.

Si, et al. "Expression of the neuroglandular antigen and analogues in melanoma. CD9 expression appears inversely related to metastatic potential of melanoma" Int J Cancer. Apr. 22, 1993;54(1):37-43.

Sladek et al., "Cellular levels of aldehyde dehydrogenases (ALDH1A1 and ALDH3A1) as predictors of therapeutic responses to cyclophosphamide-based chemotherapy of breast cancer: a retrospective study. Rational individualization of oxazaphosphorine-based cancer chemotherapeutic regimens." Cancer Chemother Pharmacol. Apr. 2002;49(4):309-21.

"Smith et al, 2004, Br. J. Cancer vol. 91 pp. 1515-24 S100A2 is strongly expressed in airway basal cells, preneoplasticbronchial lesions and primary non-small cell lung carcinomas".

Smith et al., "The TNF receptor superfamily of cellular and viral proteins: activation, costimulation, and death." Cell. Mar. 25, 1994;76(6):959-62.

Sћrlie, et al. "Gene expression patterns of breast carcinomas distinguish tumor subclasses with clinical implications" 2001, PNAS, vol. 98, pp. 10869-10874.

Spiro et al., "Lung cancer—where are we today? Current advances in staging and nonsurgical treatment" Am J Respir Crit Care Med. Nov. 1, 2002;166(9):1166-96.

Stevenson et al., "A chimeric antibody with dual Fc regions (bisFabFc) prepared by manipulations at the IgG hinge." Anticancer Drug Des. Mar. 1989;3(4):219-30.

Stipp et al., "FPRP, a major, highly stoichiometric, highly specific CD81- and CD9-associated protein." J Biol Chem. Feb. 16, 2001;276(7):4853-62.

Storms et al., "Isolation of primitive human hematopoietic progenitors on the basis of aldehyde dehydrogenase activity." Proc Natl Acad Sci U S A. Aug. 3, 1999;96(16):9118-23.

Sumerdon et al., "An optimized antibody-chelator conjugate for imaging of carcinoembryonic antigen with indium-111" Int J Rad Appl Instrum B. 1990;17(2):247-54.

Suresh et al., "Bispecific monoclonal antibodies from hybrid hybridomas." Methods Enzymol. 1986;121:210-28.

Swart "Activated leukocyte cell adhesion molecule (CD166/ALCAM): developmental and mechanistic aspects of cell clustering and cell migration." Eur J Cell Biol. Jun. 2002;81(6):313-21.

Swearingen et al., "Detection of differentially expressed HES-6 gene in metastatic colon carcinoma by combination of suppression subtractive hybridization and cDNA library array" Cancer Lett. Aug. 20, 2003;198(2):229-39.

Szmola et al., 2003, J. Biol. Chem vol. 278, pp. 48580-48589 Human Mesotrypsin Is a Unique Digestive Protease Specialized for the Degradation of Trypsin Inhibitors.

Takahashi et al, "Cloning and Characterization of Multiple Human Genes and cDNAs Encoding Highly Related Type II Keratin 6 Isoforms" J. Biol Chem vol. 270, pp. 18581-18592 (1995).

Takaku et al., "Intestinal tumorigenesis in compound mutant mice of both Dpc4 (Smad4) and Apc genes" Cell. Mar. 6, 1998;92(5):645-56.

Tepera et al., "A beta-catenin survival signal is required for normal lobular development in the mammary gland." J Cell Sci. Mar. 15, 2003;116(Pt 6):1137-49.

Tokunou,et al. "c-MET Expression in Myofibroblasts Role in Autocrine Activation and Prognostic Significance in Lung Adenocarcinoma" 2001, Am. J. Pathol. vol. 158, pp. 1451-1463.

Topol et al., "Wnt-5a inhibits the canonical Wnt pathway by promoting GSK-3-independent beta-catenin degradation." J Cell Biol. Sep. 1, 2003;162(5):899-908.

Traunecker et al., "Bispecific single chain molecules (Janusins) target cytotoxic lymphocytes on HIV infected cells." EMBO J. Dec. 1991;10(12):3655-9.

Traver et al., 1998, Immunity, vol. 9pp. 47-57 Mice Defective in Two Apoptosis Pathways in the Myeloid Lineage Develop Acute Myeloblastic Leukemia.

Trojan et al., "Prostate cancer therapy: standard management, new options and experimental approaches." Anticancer Res. Jan.-Feb. 2005;25(1B):551-61.

Tsitsikov et al., "Impaired CD19 expression and signaling, enhanced antibody response to type II T independent antigen and reduction of B-1 cells in CD81-deficient mice."Proc Natl Acad Sci U S A. Sep. 30, 1997;94(20):10844-9.

Van Kempen et al., "Activated leukocyte cell adhesion molecule/CD166, a marker of tumor progression in primary malignant melanoma of the skin" 2000, Am J Pathol vol. 156 pp. 769-774.

Van Kempen et al., "Molecular basis for the homophilic activated leukocyte cell adhesion molecule (ALCAM)-ALCAM interaction." J Biol Chem. Jul. 13, 2001;276(28):25783-90.

van Noort et al., 2002, Exp. Cell res. vol. 274, pp. 264-272 Identification of two novel regulated serines in the N terminus of beta-catenin.

van Noort et al., 2002, J. Biol. Chem. vol. 277 pp. 17901-17908 Wnt Signaling Controls the Phosphorylation Status of -Catenin.

Van Osdol et al., "Use of the Kohonen self-organizing map to study the mechanisms of action of chemotherapeutic agents." J Natl Cancer Inst. Dec. 21, 1994;86(24):1853-9.

Vaughan et al., "Human antibodies with sub-nanomolar affinities isolated from a large non-immunized phage display library."Nat Biotechnol. Mar. 1996;14(3):309-14.

Veeman et al., "A second canon. Functions and mechanisms of beta-catenin-independent Wnt signaling" Dev Cell. Sep. 2003;5(3):367-77.

Verhoeyen et al. "Reshaping human antibodies: grafting an antilysozyme activity." Science. Mar. 25, 1988;239 (4847):1534-6.

Vita, et al. "The Myc oncoprotein as a therapeutic target for human cancer" Semin Cancer Biol. Aug. 2006;16 (4):318-30.

Wade, et al. "c-Myc, genome instability, and tumorigenesis: the devil is in the details." Curr Top Microbiol Immunol. 2006;302:169-203.

Waite, et al. "From developmental disorder to heritable cancer: it's all in the BMP/TGF-beta family." Nat Rev Genet. Oct. 2003;4(10):763-73.

Wang et al., "High-fidelity mRNA amplification for gene profiling" Nat Biotechnol. Apr. 2000;18(4):457-9.

Wang, et al. "Isolation and characterization of tumorigenic extrahepatic cholangiocarcinoma cells with stem cell-like properties" Int. J. Cancer, vol. 128, pp. 72-81 (Jan. 2011).

Watanabe, et al. "Cloning and expression of human uridine phosphorylase" Biochem Biophys Res Commun. Nov. 2, 1995;216(1):265-72.

Watt, et al. "CD164—a novel sialomucin on CD34+ cells" Leuk Lymphoma. Mar. 2000;37(1-2):1-25.

Webster et al., "Sequence variants of the axin gene in breast, colon, and other cancers: an analysis of mutations that interfere with GSK3 binding." Genes Chromosomes Cancer. Aug. 2000;28(4):443-53.

Wegner, et al. "From stem cells to neurons and glia: a Soxist's view of neural development." Trends Neurosci. Nov. 2005;28(11):583-8.

Weidmann et al., 1997, Leukemia,vol. 11 pp. 79-713 Establishment and characterization of a new, factor-independent acute myeloid leukemia line designated Ei501.

Kostelny et al., "Formation of a bispecific antibody by the use of leucine zippers." J Immunol. Mar. 1, 1992;148 (5):1547-53.

Kramps et al., 2002, Cell 109:47-60 Wnt/Wingless Signaling Requires BCL9/Legless-Mediated Recruitment of Pygopus to the Nuclear-Catenin-TCF Complex.

Kristiansen et al., "ALCAM/CD166 is up-regulated in low-grade prostate cancer and progressively lost in high-grade lesions." Prostate. Jan. 1, 2003;54(1):34-43.

Kuhnert et al., "Essential requirement for Wnt signaling in proliferation of adult small intestine and colon revealed by adenoviral expression of Dickkopf-1." Proc Natl Acad Sci U S A. Jan. 6, 2004;101(1):266-71.

Kwan et al., "Essential roles of BMPR-IA signaling in differentiation and growth of hair follicles and in skin tumorigenesis." Genesis. May 2004;39(1):10-25.

La Naour et al., "Severely reduced female fertility in CD9-deficient mice." Science. Jan. 14, 2000;287(5451):319-21.

Labrecque et al., "Purification and partial characterization of a rat kidney aldehyde dehydrogenase that oxidizes retinal to retinoic acid." Biochem Cell Biol. Jan.-Feb. 1993;71(1-2):85-9.

Langenfeld, et al. "Bone morphogenetic protein-2 stimulates angiogenesis in developing tumors." Mol Cancer Res. Mar. 2004;2(3):141-9.

Leow et al., "A role for Hath1, a bHLH transcription factor, in colon adenocarcinoma." Ann N Y Acad Sci. Nov. 2005;1059:174-83.

Li et al., 2003, J. Biol. Chem, vol. 278 pp. 33445 Positive and Negative Regulation of the -Secretase Activity by Nicastrin in a Murine Model.

Liebig et al., "Forced expression of deltaN-TCF-1B in colon cancer derived cell lines is accompanied by the induction of CEACAM5/6 and mesothelin." Cancer Lett. Jun. 1, 2005;223(1):159-67.

Lin, S. Y. et al. "Beta-Catenin, a novel prognostic marker for breast cancer: its roles in cyclin D1 expression and cancer progression" Proc Natl Acad Sci USA 97, 4262-6 (2000).

Liu et al., "Effects of KAI1/CD82 on biological behavior of human colorectal carcinoma cell line." World J Gastroenterol. Jun. 2003;9(6):1231-6.

Liu et al., "Enhanced CD4+ T cell proliferation and Th2 cytokine production in DR6-deficient mice." Immunity. Jul. 2001;15(1):23-34.

Liu et al., "Sex-determining region Y box 4 is a transforming oncogene in human prostate cancer cells." Cancer Res. Apr. 15, 2006;66(8):4011-9.

Liu et al., "Signal transduction cross-talk during colorectal tumorigenesis." Adv Anat Pathol. Sep. 2006;13(5):270-4.

Liu et al., "The transforming activity of Wnt effectors correlates with their ability to induce the accumulation of mammary progenitor cells." Proc Natl Acad Sci U S A. Mar. 23, 2004;101(12):4158-63.

Liu et al., 1996, Genomics vol. 31 pp. 58-64 Epithelial expression and chromosomal location of human TLE genes: implications for notch signaling and neoplasia.

Loberg et al., "Analysis of membrane-bound complement regulatory proteins in prostate cancer." Urology. Dec. 2005;66(6):1321-6.

Locksley et al., "The TNF and TNF receptor superfamilies: integrating mammalian biology." 2001, Cell, vol. 104 pp. 487-501.

Loftus et al., 2002, PNAs vol. 99 pp. 4471-4476 Mutation of melanosome protein RAB38 in chocolate mice.

Longhi et al., "Holding T cells in check—a new role for complement regulators?" Trends Immunol. Feb. 2006;27 (2):102-8.

"Ma et al., 2005, Cancer Res. vol. 65 pp. 1479 Functional Expression and Mutations of c-Met and Its TherapeuticInhibition with SU11274 and Small Interfering RNAin Non-Small Cell Lung Cancer".

Maecker et al., "The tetraspanin superfamily: molecular facilitators." FASEB J. May 1997;11(6):428-42.

Maecker, et al. "Normal lymphocyte development but delayed humoral immune response in CD81-null mice." J Exp Med. Apr. 21, 1997;185(8):1505-10.

Magni et al., "Induction of cyclophosphamide-resistance by aldehyde-dehydrogenase gene transfer." Blood. Feb. 1, 1996;87(3):1097-103.

Maitra et al., "Molecular pathogenesis of pancreatic cancer." Best Pract Res Clin Gastroenterol. Apr. 2006;20 (2):211-26.

Markel et al., "The critical role of residues 43R and 44Q of carcinoembryonic antigen cell adhesion molecules-1 in the protection from killing by human NK cells." J Immunol. Sep. 15, 2004;173(6):3732-9.

Markova et al., 2003, Mol. Genet. Metab.vol. 78pp. 119-135 Expression pattern and biochemical characteristics of a major epidermal retinol dehydrogenase.

Marks et al., "By-passing immunization. Human antibodies from V-gene libraries displayed on phage." J Mol Biol. Dec. 5, 1991;222(3):581-97.

Martinerie et al., 2001, J. Clin. Endocrinol. Metab vol. 86. pp. 3929-3940 Altered Expression of novH Is Associated with Human Adrenocortical Tumorigenesis.

Massague et al., "Membrane-anchored growth factors." Annu Rev Biochem. 1993;62:515-41.

Matsuo et al., 2000, Nat. genet. vol. 24pp. 184-187 Fosl1 is a transcriptional target of c-Fos during osteoclast differentiation.

McCafferty et al., "Phage antibodies: filamentous phage displaying antibody variable domains." Nature. Dec. 6, 1990;348(6301):552-4.

Michaelson, et al. "beta-catenin is a downstream effector of Wnt-mediated tumorigenesis in the mammary gland." Oncogene. Aug. 23, 2001;20(37):5093-9.

Millstein et al., "Hybrid hybridomas and their use in immunohistochemistry." Nature. Oct. 6-12, 1983;305(5934):537-40.

Milovanovic et al., "Expression of Wnt genes and frizzled 1 and 2 receptors in normal breast epithelium and infiltrating breast carcinoma." Int J Oncol. Nov. 2004;25(5):1337-42.

Miyado et al., "Requirement of CD9 on the egg plasma membrane for fertilization." Science. Jan. 14, 2000;287(5451):321-4.

Miyake et al., "Motility related protein 1 (MRP-1/CD9) expression: inverse correlation with metastases in breast cancer" Cancer Res. Sep. 15, 1995;55(18):4127-31.

Miyashita et al., 2002, Cancer, vol. 94 pp. 2959-2966 Uridine phosphorylase is a potential prognostic factor in patients with oral squamous cell carcinoma.

Miyazaki et al., "BMP signals inhibit proliferation and in vivo tumor growth of androgen-insensitive prostate carcinoma cells." Oncogene. Dec. 16, 2004;23(58):9326-35.

Miyazaki et al., "Normal development but differentially altered proliferative responses of lymphocytes in mice lacking CD81" EMBO J. Jul. 16, 1997;16(14):4217-25.

Moreb et al., "Interleukin-1 and tumor necrosis factor alpha induce class 1 aldehyde dehydrogenase mRNA and protein in bone marrow cells." Leuk Lymphoma. Dec. 1995;20(1-2):77-84.

Mori et al., "Motility related protein 1 (MRP1/CD9) expression in colon cancer." Clin Cancer Res. Jun. 1998;4 (6):1507-10.

Morimoto, et al. "Single-step purification of F(ab')2 fragments of mouse monoclonal antibodies (immunoglobulins G1) by hydrophobic interaction high performance liquid chromatography using TSKgel Phenyl-5PW" 1992, Journal of Biochemical and Biophysical Methods, vol. 24, pp. 107-117.

Morrison, et al. "The Biology of Hematopoietic Stem Cells," Annu Rev. Cell Dev Biol (1995) 11:35-71.

Morrison, et al. "The biology of hematopoietic stem cells." Annu Rev Cell Dev Biol. 1995;11:35-71.

Mucenski et al., 1991, Cell vol. 65 pp. 677-689 a functional c-myb gene is required for normal murine fetal hepatic hematopoiesis.

Mukai et al., 2000, J. Biol. Chem. vol. 66 pp. 17566-17570 NADE, a p75NTR-associated Cell Death Executor, Is Involved in Signal Transduction Mediated by the Common Neurotrophin Receptor p75NTR.
Evans et al. "Establishment in culture of pluripotential cells from mouse embryos" Nature vol. 292, 1981, p. 154-6.
Farnie, G., and Clarke, R.B., "Mammary stem cells and breast cancer—role of Notch signalling," Stem Cell Rev. 3:169-175, Humana Press (2007).
Farnie, G., et al., "Novel cell culture technique for primary ductal carcinoma in situ: role of Notch and epidermal growth factor receptor signaling pathways," J. Natl. Cancer Inst. 99:616-627, Oxford University Press (2007).
Federico M et al, "In Vitro Drug Testing of Ovarian Cancer Using the Human Tumor Colony-Forming Assay: Comparison of in Vitro Response and Clinical Outcomel," Gynecologic Oncology (1994) 55(3 Pt 2): S156-63.
Felici, et al. "Selection of antibody ligands from a large library of oligopeptides expressed on a multivalent exposition vector" J. Mol. Biol. vol. 222, 1991, p. 301-10.
Fialkow, "Human Tumors Studied with Genetic Markers," Birth Defects, vol. 12, pp. 123-132 (1976).
Fillmore et al, "Human breast cancer stem cell markers CD44 and CD24: enriching for cells with functional properties in mice or in man?" Breast Cancer Res, 2007, vol. 9(303), pp. 1-3.
Fleming, R.J. et al., "The Notch receptor and its ligands," Trends in Cell Biol. 7:437-441 (1997).
Fodor "Multiplexed biochemical assays with biological chips" Nature col. 364, 1993, pp. 555-556.
Frank "MAL a proteolipid in glycosphingolipid enriched domains: functional implications in myelin and beyond" Progress in Neurobiology, vol. 60, pp. 531-544 (2000).
Fre et al., "Notch signals control the fate of immature progenitor cells in the intestine" nature 435: 964-968, 2005.
Fuh, et al., "Rational design of potent antagonists to the human growth hormone receptor," Science, 1992; 256: 1677-1680.
Gale, et al. "Haploinsufficiency of delta-like 4 ligand results in embryonic lethality due to major defects in arterial and vascular development," PNAS 101:15949-15954, National Academy of Sciences (2004).
Gallahan et al., "A new common integration region (int-3) for mouse mammary tumor viron mouse chromosome 17," J Virol. 61 (1) pp. 218-220 (1987).
Gallahan, et al. "The mouse mammary tumor associated gene INT3 is a unique member of the NOTCH gene family (NOTCH4)", Oncogene, 14(16) pp. 1883-1890 (1997).
Gallop et al., "Applications of combinatorial technologies to drug discovery. 1. Background and peptide combinatorial libraries" J Med Chem vol. 37, 1994, p. 1233.
Gat, et al, "De Novo Hair Follicle Morphogenesis and Hair Tumors in Mice Esxpression a Truncated Catenin in Skin" Cell vol. 95, pp. 605-614 (1998).
Gebre-Medhin et al, "Growth hormone receptor is expressed in human breast cancer" American Journal of Pathology, 2001: 158: 1217-1222.
Gellhaus, et al, "Connexin43 Interacts with NOV" J Biol Chem, vol. 279, pp. 36931-36942 (2004).
Ghose et al. "Preparation of antibody-linked cytotoxic agents" Methods Enzymol. vol. 93, 1983, p. 280-333.
Givehchian, No Evidence for Cancer-related CD44 Splice Variants in Primary and Metastatic Colorectal Cancer, Eur J Cancer 1998; 34: 1099-1104.
Glinsky et al, "Classification of Human Breast Cancer Using Gene Expression Profiling as a Component of the Survival Predictor Algorithm," Clinical Cancer Research, vol. 10, pp. 2272-2283 (2004).
Gossler et al. "Transgenesis by means of blastocyst-derived embryonic stem cell lines" Proc. Acad. Sci. USA vol. 83, 1986, p. 9065-9.
Goupille et al., Increase of rat colon carcinoma cells tumorigenicity by a(I-2) fucosyltransferase gene transfection, Glycobiol 1997; 7: 221-9.
Griffin et al., "Initial clinical study of indium-111-labeled clone 110 anticarcinoembryonic antigen antibody in patients with colorectal cancer" J Clin Oncol. Apr. 1991;9(4):631-40.

Gudjonsson, et al. "Isolation, immortalization, and characterization of a human breast epithelial cell line with stem cell properties." Genes Dev., 16:693-706 (2002).
Gunthert U et al. "A new variant of glycoprotein CD44 confers metastatic potential to rat carcinoma cells" Cell. Apr. 5, 1991;65(1):13-24.
Hage, et al. "Recent advances in chromatographic and electrophoretic methods for the study of drug-protein interactions" J. Chromatogr. Biomed. Sci. Appl vol. 699, 1997, pp. 499-525.
Hainaud, P., et al., "The Role of the Vascular Endothelial Growth Factor-Delta-like 4 ligand/Notch4-Ephrin B2 Cascade in Tumor Vessel Remodeling and Endothelial Cell Functions," Cancer Res. 66:8501-8510 (Sep. 2006).
Hallahan, et al. "The SmoA1 mouse model reveals that Notch signaling is critical for the growth and survival of sonic hedgehog-induced medulloblastomas." Cancer Research, 2004, vol. 64, pp. 7794-7800.
Hamburger, et al. "Primary Bioassay of Human Tumor Stem Cells," Science (Jul. 229, 1977) 197 (4302): 461-3.
Hamilton TC et al, "Characterization faXen graft Model 0' Human ovarian Carcinoma Which Produces Ascites and Intraabdominal Carcinomatosis in Mic," Cancer Research (Nov. 1984) 44(11):5286-90.
Han et al, "A soluble form of human Delta-like-1 inhibits differentiation of hematopoietic progenitor cells" Blood (Mar. 1, 2000) 95(5) 1616-25.
Hanahan, et al. 'The hallmarks of cancer' Cell vol. 100, 2000, pp. 57-70.
Harashima et al, "Human Bone marrow stroma-dependent myeloma sister cell lines MOLP-7 derived from a patient with multiple myeoloma" Hum Cell 2000, vol. 13, pp. 43-54.
Harper, et al. "Notch signaling in development and disease" Clinical Genetics, vol. 64, pp. 461-472 (2003).
Hartman et al., "MUC1 Isoform Specific Monoclonal Antibody 6E6/2 Detects Preferential Expression of the Novel Mucin Protein in Breast and Ovarian Cancer," Int J Cancer 1999; 82: 256-67.
Haskell, et al. "Efficient production of transgenic cattle by retroviral infection of early embryos" Mol. Reprod. Dev. vol. 40, 1995, p. 386-90.
Hazan et al., "Cadherin Switch in Tumor Progression," Annals NY Acad Science vol. 1014, pp. 155-163 (2004).
Hedgepeth et al, "Regulation of Glycogen Synthase Kinase 3 and Downstream Wnt Signaling by Axin," Molecular and Cellular Biol, vol. 19, pp. 7147-7157 (1997).
Heegaard "Capillary electrophoresis for the study of affinity interactions" J. Mol. Recognit vol. 11, 1998, pp. 141-148.
Hellstrom, M., et al. "Dll4 signalling through Notch1 regulates formation oftip cells during angiogenesis," Nature 445:776-780, Nature Publishing Group (2007).
Hennighausen L, Mouse Models for Breast Cancer, Breast Cancer Res 2: 2-7 (Dec. 17 1999).
Henrique, et al. "Maintenance of neuroepithelial progenitor cells by Delta-Notch signalling in the embryonic chick retina" Curr Biol. 7(9) pp. 661-70 (1997).
Heppner, "Tumor Heterogeneity," Cancer Research vol. 44, pp. 2259-2265 (1984).
Herbert et al, "Molecular physiology of cation-coupled Cl-cotransport: the SLC12 family" Pglugers Arch. European J Physiology vol. 447, pp. 580-593 (2004).
Hering H et al., "Direct interaction of Frizzled-1, -2, -4 and -7 with PDZ domains of PSD-95" FEBS Letters, Elsevier, Amsterdam, NL, vol. 521, No. 1-3, Jun. 19, 2002, pp. 185-189.
Herman-Bonert et al., Growth hormone receptor antagonist therapy in acromegalic patients resistant to somatostatin anaologs, J. Clin. Endocrinol Metab. 2000; 85:2958-2961.
Hicks, et al. "Fringe differentially modulates Jagged1 and Delta1 signalling through Notch1 and Notch2" N-at Cell Biol. (8) pp. 515-20 (2000).
Hiraki et al., "Tumor Cell Assay for Detecting Metastases of Human Lung Cancer," Acta Med. Okayama, 37 (2), pp. 141-146 (1983).
Cadigan, et al. "Wnt signaling: a common theme in animal development" Genes &Development 11. 3286-305 (1997).

Callahan et al., "Notch Signalling in Mammary Gland Tumorigenesis" Journal of Mammary Gland Biology and Neoplasia 6:1 pp. 23-26 (Jan. 2001).

Candidus, et al. "No evidence for mutations in the alpha- and beta-catenin genes in human gastric and breast carcinomas" Cancer Res 56, 49-52 (1996).

Cao et al, "Identification of Novel Highly Expressed Genes in Pancreatic Ductal Adenocarcinomas through a Bioinformatics Analy" (2004) Cancer Biology & Therapy, vol. 3, pp. 1081-1089.

Caplen et al. "Specific inhibition of gene expression by small double-stranded RNAs in invertebrate and vertebrate systems" Proc Natl Acad Sci U.S.A. vol. 98, 2001, pp. 9742-9747.

Carney, et al. "Demonstration of the stem cell nature of clonogenic tumor cells from lung cancer patients" Stem Cells. 1982;1(3):149-64.

Carrell et al. "A Novel Procedure for the Synthesis of Libraries Containing Small Organic Molecules" Angew Chem Int Ed Engl vol. 33, 1994, p. 2059-2061.

Carver and Schnitzer "Caveolae: Mining Little Caves for New Cancer Targets," Nature Review, 3: 571-81 (2003).

Chamow (Charnow)et al. "A humanized, bispecific immunoadhesin-antibody that retargets CD3+ effectors to kill HIV-1-infected cells" J Immunol vol. 153, 1994, p. 4268-80.

Chan et al, "A common human skin tumour is caused by activating mutations in catenin," Nature Genetics, vol. 21, pp. 410-413 (1999).

Chang et al., "Robustness, scalability, and integration of a wound-response gene expression signature in predicting breast cancer survival," PNAS, vol. 102, pp. 3738-3742 (2005).

Chari Ravi V.J. "Targeted elivery of Chemotherapeutics: tumor-activated prodrug therapy," Advanced Drug Delievery Rev 31:89-104 (1998).

Charrin S, Le Naour F, Oualid M, Billard M, Faure G, Hanash SM, Boucheix C, Rubinstein E.

Cho et al., "An unnatural biopolymer" Science, vol. 261, 1993, p. 1303-5.

Choi "CD44S Expression in Human Colon Carcinomas Influences Growth of Liver Metastases,' Int J Cancer 2000; 85: 523-6.

Christensen, et al. "lag-1, a gene required for lin-12 and glp-1 signaling in *Caenorhabditis elegans*, is homologoto human CBF1 and Drosophila Su(H)" Development 122, 1373-83 (1996).

Christensen, et al. 'Flk-2 is a marker in hematopoietic stem cell differentiation: a simple method to isolate long-term stem cells' Proc Natl Acad Sci USA vol. 98, 2001, pp. 14541-14546.

Christoori et al, "The Role of the Cell-adhesion molecule *E-cadherin* as a Tumor-suppressor gene" Trends in biochemical sciences, Elsevier Haywards, GB vol. 24, No. 2, (Feb. 1, 1990) pp. 73-76.

Clarke et al, "At the root of brain cancer" Nature 432: 281-2 (2004).

Clarke et al., "A recombinant bcl-x's adenovirus selectively induces apoptosis in cancer cells but not in normal bone marrow cells," Proc Natl Acad Sci USA (Nov. 1995) 92: 10024-11028.

Closs et al, "Identification of a Low Affinity, High Capacity Transporter of Cathionic Amino Acids in Mouse Liver" J Biol. Chem. vol. 268, pp. 7538-7544 (1993).

Cohen et al, "Role of Cabeolae and Cabeolins in Health and Disease" Physiol., Rev vol. 84, pp. 1341-1379 (2004).

Collins, "Prospective Identification of Tumorigenic Prostate Cancer Stem Cells," Cancer Res. Dec. 1, 2005;65 (23):10946-51.

Coopman, et al. "The Syk tyrosine kinase suppresses malignant growth of human breast cancer cells" Nature, Aug. 17, 2000, pp. 742-747, vol. 406 Nature Publishing Group, London GB.

Cristillo et al. "Cyclosporin a Inhibits Early mRNA Expression of GOS2) in Cultured Human Blood Mononuclear Cells" DNA and Cell Biology, vol. 16, pp. 1449-1458 (1997).

Cull et al., "Screening for receptor ligands using large libraries of peptides linked to the C terminus of the lac repressor" Proc Nad Acad Sci USA vol. 89, 1992, p. 1865-1869.

Curry et al. "Gamma secretase inhibitor blocks Notch activation and induces apoptosis in Kapo's sarcoma tumor cells" Oncogene, 2005 vol. 24 pp. 6333-6344.

Cwirla et al. "Peptides on phage: a vast library of peptides for identifying ligands" Proc. Natl. Acad. Sci. vol. 87, 1990, pp. 6378-6382.

Dalerba et al., "Phenotypic characterization of human colorectal cancer stem cells" PNAS 2007; 104: 10158-63.

Dando, J. et al., "Notch/Delta4 Interaction in Human Embryonic Liver CD34+CD38− Cells: Positive Influence on Bgue Production in LTC-IC Potential Maintenance," Stem Cells 23:550-560 (2005).

Database Genbank [Online] "*Homo sapiens* S100 calcium-binding protein A8 (calgranul in a) (S100A8) mRNA" Mar. 19, 1999, XP002470523, Database accession No. NM 002964.

Database Geneseq [Online]: "Breast cancer prognosis marker #845." Oct. 21, 2004, XP002470535 retrieved from EBI accession No. GSN:ADR24984 70535 accession No. ADR24984.

De Both et al, "Clonal growth of colorectal-carcinoma cell lines transplanted to nude mice" Int J Cancer, 1997, vol. 72, pp. 1137-1141.

Deftos, et al. "Correlating notch signaling with thymocyte maturation" Immunity. vol. 9(6):777-86 (1998).

Deschaseaux et al., "Direct selection of human bone marrow mesenchymal stem cells using an anti-CD49a antibody reveals their CD4Smed.low phenotype," Brit J. Haematology 2003, 122, 506-517.

Devlin "Random peptide libraries: a source of specific protein binding molecules" Science vol. 249, 1990, pp. 404-406.

Dewitt et al. ""Diversomers": an approach to nonpeptide, nonoligomeric chemical diversity" Proc Natl Acad Sci., vol. 90, pp. 6909-6913, 1993.

Dick, "Breast Cancer Stem Cells Revealed," PNAS USA2003 100 (7), 3547-3549.

Diederichs, et al, "S100 Family Members and Trypsinogens Are Predictors of Distant metastiasis and Survival in Early-Stage Non-Small Cell Lung Cancer" Cancer Res. vol. 64, pp. 5564-5569 (2004).

Domen, et al. 'The Role of Apoptosis in the Regulation of Hematopoietic Stem Cells: Overexpression of BCL-2 Increases Both Their Number and Repopulation Potential' 1. Exp. Med. vol. 191, 2000, pp. 253-264.

Domen, J.; Weissman, I. L: 'Hematopoietic stem cells need two signals to prevent apoptosis; BCL-2 can provide one of these, Kitl/c-Kit signaling the other' J Exp Med vol. 192, 2000, pp. 1707-1718.

Dorsch, M., et al., "Ectopic expression of Delta4 impairs hematopoietic development and leads to lymphoproliferative disease," Blood 100:2046-2055 (2002).

Duarte, A., et al., "Dosage-sensitive requirement for mouse Dll4 in artery development," Genes Dev. 18:2474-2478, Cold Spring Harbor, NY U.S.A. (2004).

Edwards et al., "A Newly Defined Property of Somatotropin: Priming of Macrophages for Production of Superoxide Anion," Science, 239: 769 (1988).

Elbashir et al. "Duplexes of 21-nucleotide RNAs mediate RNA interference in cultured mammalian cells" Nature vol. 411, 2001, pp. 494-498.

Elbashir et al. "Functional anatomy of siRNAs for mediating efficient RNAi in *Drosophila melanogaster* embryo lysate" EMBO J. vol. 20, 2001, pp. 6877-6888.

Elbashir et al. "RNA interference is mediated by 21- and 22-nucleotide RNAs" Genes Dev. vol. 15, 2001, pp. 188-200.

Ellisen, L.W., et al., "TAN-1, the Human Homolog of the Drosophila Notch Gene, Is Broken by Chromosomal Translocations in T Lymphoblastic Neoplasms," Cell 66:649-661, Elsevier Inc., Amsterdam, The Netherlands (1991).

Erb et al., "Recursive deconvolution of combinatorial chemical libraries" Proc Nad Acad Sci vol. 91 1994, p. 11422-6.

Ethier, et al. "Differential Isolation of normal luminal mammary epithelial cells and breast cancer cells from primary and metastatic sites using selective media" Cancer Res 53. 627-35 (1993).

Weinstein et al., 1992, Science, vol. 258 pp. 447-451 Neural computing in cancer drug development: predicting mechanism of action.

Weinstein et al., 1997, Science vol. 275 pp. 343-390 an information-intensive approach to the molecular pharmacology of cancer.

Weitz et al., "Colorectal cancer" Lancet. Jan. 8-14, 2005;365(9454):153-65.

Weng, et al. "Activating mutations in Notch1 in T cell acute lymphoblastic leukemia" Science 2004;306:269-71.

Wharton et al., "Nucleotide sequence from the neurogenic locus notch implies a gene product that shares homology with proteins containing EGF-like repeats." Cell. Dec. 1985;43(3 Pt 2):567-81.

Winzeler, et al. "Fluorescence-based expression monitoring using microarrays" Methods Enzymol. 1999;306:3-18.

Wolff et al., "Monoclonal antibody homodimers: enhanced antitumor activity in nude mice." Cancer Res. Jun. 1, 1993;53(11):2560-5.

Wong et al., "A rapid chemical method of labeling human plasma proteins with 99mTc-pertechnetate at pH 7.4." Int J Appl Radiat Isot. May 1978;29(4-5):251-3.

Wong et al., "Imaging endocarditis with Tc-99m-labeled antibody—an experimental study: concise communication." J Nucl Med. Mar. 1982;23(3):229-34.

Wong et al., 1994, Mol Cell Biol. vol. 14pp. 6278-6286, Differential transformation of mammary epithelial cells by Wnt genes.

Wu, et al. "Ligand receptor interactions in the Wnt signaling pathway in Drosophila." J Biol Chem. Nov. 1, 2002;277 (44):41762-9.

Yan et al., "Dual roles of Cripto as a ligand and coreceptor in the nodal signaling pathway." Mol Cell Biol. Jul. 2002;22 (13):4439-49.

Yan et al., 2004, J. Neurosci. 24: 2942 Binding Sites of -Secretase Inhibitors in Rodent Brain.

Yang et al. "Study design considerations in clinical outcome research of lung cancer using microarray analysis" 2004 Lung Cancer 46:215-226.

Yao, et al. "Side population in the pancreatic cancer cell lines SW1990 and CFPAC-1 is enriched with cancer stem-like cells" Oncol. Rep. vol. 23, pp. 1375-1382 (2010).

Yasui et al., "Search for new biomarkers of gastric cancer through serial analysis of gene expression and its clinical implications." Cancer Sci. May 2004;95(5):385-92.

Yeo, et al. "Nodal signals to Smads through Cripto-dependent and Cripto-independent mechanisms." Mol Cell. May 2001;7(5):949-57.

Yu et al., 2001, Nature vol. 411 pp. 1017-1021 Specific protection against breast cancers by cyclin D1 ablation.

Zhang, et al. "A negatively charged residue in the outer mouth of rat sodium channel determines the gating kinetics of the channel." Am J Physiol Cell Physiol. May 2003;284(5):C1247-54.

Zhao et al., "Impaired c-Jun amino terminal kinase activity and T cell differentiation in death receptor 6-deficient mice." J Exp Med. Nov. 19, 2001;194(10):1441-8.

Zhou et al., "Bcrp1 gene expression is required for normal numbers of side population stem cells in mice, and confers relative protection to mitoxantrone in hematopoietic cells in vivo." Proc Natl Acad Sci U S A. Sep. 17, 2002;99 (19):12339-44.

Zhou et al., "Germline mutations in BMPR1A/ALK3 cause a subset of cases of juvenile polyposis syndrome and of Cowden and Bannayan-Riley-Ruvalcaba syndromes." Am J Hum Genet. Oct. 2001;69(4):704-11.

Zhu et al., "Smad3 mutant mice develop metastatic colorectal cancer." Cell. Sep. 18, 1998;94(6):703-14.

Hoyert DL, Heron MP, Murphy SL, Kung, HC. Deaths: final data for 2003. Natl Vital Stat Rep 2006; 19: 1-120.

Litvinov SV, Velders MP, Bakker HA, Fleuren GJ, et al. Ep-CAM: a human 22 epithelial antigen is a homophilic cell-cell adhesion molecule. J. Cell Biol. 1994; 125: 437-446.

Matsui, et al. "Characterization of clonagenic multiple myeloma cells" Blood 2004; 103: 2332-2336.

Ponta H, Sherman L, Herrlich PA. CD44: from adhesion molecules to signalling regulators. Nat Rev Mol Cell 2003; 4: 33-45.

Hathorn et al., "In vitro Modulation of the Invasive Metastatic Potentials of Human Renal Cell Carcinoma by Interleukin-2 and/or Interferon—Alpha Gene Transfer," Cancer 1994, 74: 1904-11.

Cha, et al. "Inhibition of FGF signaling causes expansion of the endoderm in Xenopus" 2004, Biochem Biophys Res Commun, vol. 315, pp. 100-106.

Sheridan, et al. "CD44+/CD24– breast cancer cells exhibit enhanced invasive properties: an early step necessary for metastasis" Breast CancerResearc, vol. 8, pp. 1-13 (2006).

Mukai et al., 2003, Vitam. Horm, vol. 66 pp. 385-402 Nerve growth factor-dependent regulation of NADE-induced apoptosis.

Mundy, et al. "Boning up on ephrin signaling." Cell. Aug. 11, 2006;126(3):441-3.

Muthuramalingam et al., "Management of patients with hormone refractory prostate cancer." Clin Oncol (R Coll Radiol). Dec. 2004;16(8):505-16.

Mutoh et al., "The intestine-specific homeobox gene Cdx2 induces expression of the basic helix-loop-helix transcription factor Math1." Differentiation. Jul. 2006;74(6):313-21.

Nakamoto, et al. "Diverse roles for the Eph family of receptor tyrosine kinases in carcinogenesis." Microsc Res Tech. Oct. 1, 2002;59(1):58-67.

Nakamura et al., "The bHLH gene hes1 as a repressor of the neuronal commitment of CNS stem cells." J Neurosci. Jan. 1, 2000;20(1):283-93.

"Neilsen et al., 1999, Mol. Cell. Biol. vol. 19 pp. 1262-1270 Christiansen, JensDevelopment Represses Translation in Late Factor II mRNA-Binding Proteins a Family of Insulin-Like Growth".

Nishanian et al. "Suppression of tumorigenesis and activation of Wnt signaling by bone morphogenetic protein 4 in human cancer cells." Cancer Biol Ther. Jul. 2004;3(7):667-75.

"Nusse, 1999, Trends genet, vol. 15pp. 1-3 Wnt targetsrepression and activation".

Nusse, R. "Insertional mutagenesis in mouse mammary tumorigenesis" Current Topics in Microbiology & Immunology 171,43-65 (1991).

Okamoto et al., 1994, PNAS, vol. 91pp. 11045 Mutations and altered expression of p16INK4 in human cancer.

Olson, et al. "Antisense wnt-5a mimics writ-1-mediated C57MG mammary epithelial cell transformation" Exp Cell Res. May 25, 1998;241(1):134-41.

Ongusaha et al., "HB-EGF is a potent inducer of tumor growth and angiogenesis" Cancer Res. Aug. 1, 2004;64 (15):5283-90.

Orlicky "Negative regulatory activity of a prostaglandin F2 alpha receptor associated protein (FPRP)." Prostaglandins Leukot Essent Fatty Acids. Apr. 1996;54(4):247-59.

Orlicky et al., "Synthesis and accumulation of a receptor regulatory protein associated with lipid droplet accumulation in 3T3-L1 cells" J Lipid Res. Jun. 1998;39(6):1152-61.

Oshima et al., "Morphological and molecular processes of polyp formation in Apc(delta716) knockout mice." Cancer Res. May 1, 1997;57(9):1644-9.

Paull et al., 1989, J. Nat. Cancer. Inst. vol. 81 pp. 1088-1092 Display and analysis of patterns of differential activity of drugs against human tumor cell lines: development of mean graph and Compare algorithm.

Pinto et al., "Canonical Wnt signals are essential for homeostasis of the intestinal epithelium." Genes Dev. Jul. 15, 2003;17(14):1709-13.

Player et al., "Identification of TDE2 gene and its expression in non-small cell lung cancer." Int J Cancer. Nov. 1, 2003;107(2):238-43.

Pouliot et al., "Overexpression of a dominant negative type II bone morphogenetic protein receptor inhibits the growth of human breast cancer cells." Cancer Res. Jan. 15, 2003;63(2):277-81.

Pramoonjago et al. "Knockdown of Sox4 expression by RNAi induces apoptosis in ACC3 cells." Oncogene. Sep. 14, 2006;25(41):5626-39.

Prochownik, et al. "Deregulated expression of c-myc by murine erythroleukaemia cells prevents differentiation" Nature. Aug. 28-Sep. 3, 1986;322(6082):848-50.

Quash et al. "Novel competitive irreversible inhibitors of aldehyde dehydrogenase (ALDH1): restoration of chemosensitivity of L1210 cells overexpressing ALDH1 and induction of apoptosis in BAF(3) cells overexpressing bcl (2)." Biochem Pharmacol. Oct. 15, 2002;64(8):1279-92.

Raida et al. "Expression of bone morphogenetic protein 2 in breast cancer cells inhibits hypoxic cell death" Int J Oncol. Jun. 2005;26(6):1465-70.

Ramsay "c-Myb a stem-progenitor cell regulator in multiple tissue compartments" Growth Factors. Dec. 2005;23 (4):253-61.

Ramsay et al. "Expression of stress response protein glucose regulated protein-78 mediated by c-Myb" Int J Biochem Cell Biol. Jun. 2005;37(6):1254-68.

Reichling et al. "Transcriptional profiles of intestinal tumors in Apc(Min) mice are unique from those of embryonic intestine and identify novel gene targets dysregulated in human colorectal tumors." Cancer Res. Jan. 1, 2005;65 (1):166-76.

Renehan et al., 2004, Lancet,vol. 363pp. 1346 Insulin-like growth factor (IGF)-I, IGF binding protein-3, and cancer risk: systematic review and meta-regression analysis.

Reya, et al. "A role for Wnt signalling in self-renewal of haematopoietic stem cells" Nature 423,409-14 (2003).

Reyes et al., 1992, Science vol. 256 pp. 1193-1195 Identification of the Ah receptor nuclear translocator protein (Amt) as a component of the DNA binding form of the Ah receptor.

Riechmann et al. "Reshaping human antibodies for therapy" Nature, vol. 332: 323-327 1988.

Rocha Lima, et al. "Beyond Pancreatic Cancer: Irinotecan and Gemcitabine in Solid Tumors and Hematologic Malignancies" Seminars in Oncology, 2001 Suppl. 10 vol. 28, pp. 34-43.

Roda Navarro et al., 2001, Biochem. Biophys. Acta. vol. 1520pp. 141-146 Molecular characterization of two novel alternative spliced variants of the KLRF1 gene and subcellular distribution of KLRF1 isoforms.

Roose et al. "Synergy between tumor suppressor APC and the beta-catenin-Tcf4 target Tcf1" Science. Sep. 17, 1999;285(5435):1923-6.

Rubinstein et al. "CD9, CD63, CD81, and CD82 are components of a surface tetraspan network connected to HLA-DR and VLA integrins." Eur J Immunol. Nov. 1996;26(11):2657-65.

Russo et al. "The role of aldehyde dehydrogenase isozymes in cellular resistance to the alkylating agent cyclophosphamide." Prog Clin Biol Res. 1989;290:65-79.

Saitoh et al. "Frequent up-regulation of WNT5A mRNA in primary gastric cancer" Intl J Mol Med vol. 9, pp. 515-519 (2002).

Saitoh et al., "Up-regulation of WNT8B mRNA in human gastric cancer," Int J Oncology vol. 20, pp. 343-348 (2002).

Sakakura et al, "Differential gene expression profiles of gastric cancer cells established from primary tumor and malignant ascites" Bri J Cancer, 2002, vol. 87, pp. 1153-1161.

Sakamoto et al. "Proper levels of c-Myb are discretely defined at distinct steps of hematopoietic cell development." Blood. Aug. 1, 2006;108(3):896-903.

Salmon et al., Quantitation of Deferential Sensitivity of Human-Tumor Stem Cells to Anticancer Drugs, New Engl J Med 1978, 298: 1321-7.

Salomon et al. "The EGF-CFC family: novel epidermal growth factor-related proteins in development and cancer" Endocr Relat Cancer. Dec. 2000;7(4):199-226.

Saulnier-Blache et al., 2000 A simple and highly sensitive radioenzymatic assay for lysophosphatidic acid quantification. J. Lipid Res. vol. 41(12) pp. 1947-1951.

Scharenberg et al. "The ABCG2 transporter is an efficient Hoechst 33342 efflux pump and is preferentially expressed by immature human hematopoietic progenitors." Blood. Jan. 15, 2002;99(2):507-12.

Schedlich & Graham, Microsc Res Tech. Oct. 1, 2002;59(1):12-22. Role of insulin-like growth factor binding protein-3 in breast cancer cell growth.

Scheinberg et al., 1982, Science, vol. 215pp. 1151 Tumor imaging with radioactive metal chelates conjugated to monoclonal antibodies.

Schmidt et al. "Enhanced B cell expansion, survival, and humoral responses by targeting death receptor 6."J Exp Med. Jan. 6, 2003;197(1):51-62.

Scholzel et al., "Carcinoembryonic antigen family members CEACAM6 and CEACAM7 are differentially expressed in normal tissues and oppositely deregulated in hyperplastic colorectal polyps and early adenomas." Am J Pathol. Feb. 2000;156(2):595-605.

Schonhoff et al, "Minireview: Development and differentiation of gut endocrine cells" 2004, Endocrinol 145: 2639-44.

Schteingart et al., 2001, J. Clin. Endocrinol. Metab vol. 86 pp. 3968 Overexpression of CXC Chemokines by an Adrenocortical Carcinoma: A Novel Clinical Syndrome.

"Buske et al., 2002, Blood vol. 100 pp. 862-881 Deregulated expression of HOXB4 enhances the primitive growth activity of human hematopoietic cells".

Cai et al., "Membrane properties of rat embryonic multipotent neural stem cells." J Neurochem. Jan. 2004;88 (1):212-26.

"Capobianco et al., 1997, Mol Cell Biol. vol. 17 pp. 6265-6273 Neoplastic Transformation by Truncated Alleles of Human-NOTCH1/TAN1 and NOTCH2".

Caron et al., "Engineered humanized dimeric forms of IgG are more effective antibodies." J Exp Med. Oct. 1, 1992;176(4):1191-5.

Cavallaro, et al. "Cell adhesion and signalling by cadherins and Ig-CAMs in cancer" Nat Rev Cancer. Feb. 2004;4 (2):118-32.

CD44: Mesh term database, PubMed, 2004.

Cerny, et al. "Mechanism of action of rituximab" Anticancer Drugs. Nov. 2002;13 Suppl 2:S3-10.

Chakraborty & Pawelek, 2003, Clin Exp Metastasis vol. 20pp. 365-373 GnT-V, macrophage and cancer metastasis: a common link.

Charalabopoulos et al., "Cadherin superfamily of adhesion molecules in primary lung cancer" Exp Oncol. Dec. 2004;26(4):256-60.

Charrin, et al. "The major CD9 and CD81 molecular partner. Identification and characterization of the complexes" J Biol Chem. Apr. 27, 2001;276(17):14329-37.

Chen et al., "Bone morphogenetic proteins" 2004, Growth Factors vol. 22, pp. 233-241.

Cheng et al., 2000, Science vol. 287 pp. 1804-1808 Hematopoietic stem cell quiescence maintained by p21cip1/waf1.

Cheung et al., "Making and reading microarrays." Nat Genet. Jan. 1999;21(1 Suppl):15-9.

"Chin et al., 1999, Nature, vol. 400 pp. 468-472 Essential role foroncogenicRas in tumourmaintenance".

Chinnaiyan, et al. "FADD, a novel death domain-containing protein, interacts with the death domain of Fas and initiates apoptosis" Cell, 81(4):505-12 (1995).

Choong et al., Cytokine. Mar. 21, 2004;25(6):239-45. LIX: a chemokine with a role in hematopoietic stem cells maintenance.

Chute et al., "Inhibition of aldehyde dehydrogenase and retinoid signaling induces the expansion of human hematopoietic stem cells" Proc Natl Acad Sci U S A. Aug. 1, 2006;103(31):11707-12.

Clackson, et al. "Making antibody fragments using phage display libraries." Nature. Aug. 15, 1991;352(6336):624-8.

Clevers "Wnt breakers in colon cancer" 2004, Cancer Cell vol. 5, pp. 5-6.

Cole et al., "Beyond lysis: how complement influences cell fate." Clin Sci (Lond). May 2003;104(5):455-66.

Cole et al., 1985, Monoclonal Antibodies and Cancer Therapy, Alan R. Liss p. 77.

Colvin OM, Pharmacological Purging of the Borne Marrow (2nd ed) Blackwell Sciences Inc. 1999.

Cowin et al., "Cadherins and catenins in breast cancer." Curr Opin Cell Biol. Oct. 2005;17(5):499-508.

Crosnier et al., "Organizing cell renewal in the intestine: stem cells, signals and combinatorial control." Nat Rev Genet. May 2006;7(5):349-59.

Cui, et al. 2003, J. Immunol. vol. 171 pp. 6814 Shedding of the Type II IL-1 Decoy Receptor Requires a Multifunctional Aminopeptidase, Aminopeptidase Regulator of TNF Receptor Type 1 Shedding.

Dai et al., "Vascular endothelial growth factor contributes to the prostate cancer-induced osteoblast differentiation mediated by bone morphogenetic protein" Cancer Res. Feb. 1, 2004;64(3):994-9.

Danen, "Integrins: regulators of tissue function and cancer progression." Curr Pharm Des. 2005;11(7):881-91.

Danish et al., 1992, Oncogene vol. 7 pp. 901-907 c-myb effects on kinetic events during MEL cell differentiation.

Datta, et al. "STRAP and Smad7 synergize in the inhibition of transforming growth factor beta signaling" Mol Cell Biol. May 2000;20(9):3157-67.

Domen et al., 1998, Blood vol. 91 pp. 2272-2282 Systemic Overexpression of BCL-2 in the Hematopoietic System Protects Transgenic Mice From the Consequences of Lethal Irradiation.

Dorrell et al., 2000, Blood, vol. 95, pp. 102-110 Expansion of human cord blood CD341CD382 cells in ex vivo culture during retroviral transduction without a corresponding increase in Scid repopulating cell (SRC) frequency: dissociation of SRC phenotype and function.

Dumitrascu, "Mast cells as potent inflammatory cells" 1996, Romanian Journal of Internal Medicine, vol. 34, pp. 159-172.

Duncan et al., "Integration of Notch and Wnt signaling in hematopoietic stem cell maintenance" Nat Immunol. Mar. 2005;6(3):314-22.

Duxbury et al., "CEACAM6 cross-linking induces caveolin-1-dependent, Src-mediated focal adhesion kinase phosphorylation in BxPC3 pancreatic adenocarcinoma cells" J Biol Chem. May 28, 2004;279(22):23176-82.

Duxbury et al., "CEACAM6 gene silencing impairs anoikis resistance and in vivo metastatic ability of pancreatic adenocarcinoma cells" Oncogene. Jan. 15, 2004;23(2):465-73.

Duxbury et al., "c-Src-dependent cross-talk between CEACAM6 and alphavbeta3 integrin enhances pancreatic adenocarcinoma cell adhesion to extracellular matrix components" Biochem Biophys Res Commun. Apr. 23, 2004;317 (1):133-41.

Eisen et al., 1998, PNAS, 95:14863-14868 Cluster analysis and display of genome-wide expression patterns.

Eisen, et al. "DNA arrays for analysis of gene expression" Methods Enzymol. 1999;303:179-205.

Emberely et al., 2004, Biochem Cell Biol vol. 82pp. 508-515 S100 proteins and their influence on pro-survival pathways in cancer.

Furley, et al. "Divergent molecular phenotypes of KG1 and KG1a myeloid cell lines" 1986, Blood, vol. 68, pp. 1101-1107.

Gage "Mammalian neural stem cells." Science. Feb. 25, 2000;287(5457):1433-8.

Gazit, et al. "Human frizzled 1 interacts with transforming Wnts to transduce a TCF dependent transcriptional response" 1999, Oncogene 18:5959-66.

Georgolios et al., "Role and expression patterns of *E-cadherin* in head and neck squamous cell carcinoma (HNSCC)." J Exp Clin Cancer Res. Mar. 2006;25(1):5-14.

Gilles et al., "Transactivation of vimentin by beta-catenin in human breast cancer cells." Cancer Res. May 15, 2003;63(10):2658-64.

Glavinas et al., "The role of ABC transporters in drug resistance, metabolism and toxicity." Curr Drug Deliv. Jan. 2004;1(1):27-42.

Goding, 1986, Monoclonal Antibiodies: Principles and practice.

Gong et al., "Role of a5B1 Integrin in Determining Malignant Properties of Colon Carcinoma Cells," Cell Growth Different 1997; 8: 83-90.

Goodell et al., "Isolation and functional properties of murine hematopoietic stem cells that are replicating in vivo" J Exp Med. Apr. 1, 1996;183(4):1797-806.

Goodyear, et al. "Dysplasia of Human Prostate CD133hi Sub-Population in NOD-SCIDS Is Blocked by c-myc Anti-Sense" The Prostate, vol. 69, pp. 689-698 (2009).

Greene et al., 1998, Eur. J. Neurosci. Greene et al., 1998, Eur. J. Neurosci. vol. 10 pp. 1911-1925 Identification and characterization of a novel member of the fibroblast growth factor family.

US 5,962,233, 10/1999, Livak (withdrawn)

* cited by examiner

COMPOSITIONS AND METHODS FOR TREATING AND DIAGNOSING PANCREATIC CANCER

The present application claims priority to U.S. Provisional Application Ser. No. 60/897,190, filed Jan. 24, 2007, which is herein incorporated by reference in its entirety.

FIELD OF THE INVENTION

The present invention relates to the field of oncology and provides novel compositions and methods for diagnosing and treating pancreatic cancer. In particular, the present invention provides pancreatic cancer stem cells useful for the study, diagnosis, and treatment of solid tumors.

BACKGROUND

Pancreatic adenocarcinoma is a highly lethal disease which is usually diagnosed in an advanced state for which there are little/no effective therapies. It has the worst prognosis of any major malignancy (3% 5 year survival) and is the fourth most common cause of cancer death per year in the United States, with an annual incidence rate approximating the annual death rate of 31,000 people (1). Despite advances in surgical and medical therapy, little impact has been made on the mortality rate of this disease. One of the major hallmarks of pancreatic cancer is its extensive local tumor invasion and early systemic dissemination. The molecular basis for these characteristics of pancreatic cancer is incompletely understood.

Attempts to better understand the molecular characteristics of pancreatic cancer have focused on studying gene and protein expression profiles of samples of pancreatic cancer. However, these types of studies have not taken into account the heterogeneity of cancer cells within a particular tumor. A practical consequence of this tumor cell heterogeneity is that strategies for inducing cell death must address the unique survival mechanisms of each different cell type within the malignant population.

What is needed are improved compositions and methods for understanding, detecting, and treating cancer having heterogenous cell populations.

BRIEF SUMMARY OF THE INVENTION

The present invention relates to the field of oncology and provides novel compositions and methods for diagnosing and treating pancreatic cancer. In particular, the present invention provides pancreatic cancer stem cells useful for the study, diagnosis, and treatment of solid tumors.

In some embodiments, the present invention provides isolated pancreatic tumor stem cells. In certain embodiments, the present invention provides an isolated population of cancer stem cells that are: a) tumorigenic; b) CD44+; c) CD24+ and, d) ESA+. In other embodiments, the isolated population comprises at least 75% cancer stem cells and less than 25% non-tumorigenic tumor cells. In particular embodiments, the cancer stem cells are pancreatic cancer stem cells or highly virulent breast cancer stem cells. In further embodiments, the cancer stem cells have upregulated expression of SHH. In other embodiments, the cancer stem cells: are enriched at least two-fold compared to unfractionated non-tumorigenic tumor cells.

In certain embodiments, the present invention provides methods of obtaining from a tumor an isolated population of cancer stem cells comprising: a) contacting a mixture of tumor cells from a tumor with reagents against one or more of: CD44, CD24, and ESA, and b) positively selecting for cells that are CD44+, CD24+, and/or ESA+.

In other embodiments, the present invention provides methods of diagnosing the presence of pancreatic solid tumor stem cells in a patient comprising; a) contacting a sample from the patient comprising tumor cells, and b) identifying the presence or absence of pancreatic solid tumor stem cells in the sample, wherein presence of cells that are CD44+, CD24+, and ESA+ positive indicates that pancreatic solid tumor stem cells are present.

In some embodiments, the present invention provides methods for obtaining from a tumor a cellular composition comprising cancer stem cells and non-tumorigenic tumor cells, wherein at least 75% are tumorigenic stem cells and 25% or less are non-tumorigenic tumor cells, the method comprising: a) obtaining a dissociated mixture of tumor cells from a tumor; b) separating the mixture of tumor cells into a first fraction comprising at least 75% cancer stem cells and 25% or less non-tumorigenic tumor cells and a second fraction of tumor cells depleted of cancer stem cells wherein the separating is by contacting the mixture with reagents against CD44, CD24, and/or ESA; and c) demonstrating the first fraction to be tumorigenic by serial injection into a first host animal and the second fraction to be non-tumorigenic by serial injection into a second host animal. In certain embodiments, the separating is performed by flow cytometry, fluorescence activated cell sorting (FACS), panning, affinity chromatography or magnetic selection. In other embodiments, the separating is performed by fluorescence activated cell sorters (FACS) analysis.

In some embodiments, the present invention provides methods of identifying the presence of pancreatic cancer stem cells in a subject suspected of having cancer, wherein the method comprises: (a) obtaining a biological sample from the subject; (b) dissociating cells of the sample; (c) contacting the dissociated cells with a first reagent that binds CD44, a second reagent that binds CD24, and/or a third reagent that binds ESA; and (d) detecting cancer stem cells that bind to the first, second, and/or third reagents.

In certain embodiments, the first, second, or third reagent is an antibody. In further embodiments, the detection step is performed by flow cytometry, fluorescence activated cell sorting, panning, affinity column separation, or magnetic selection.

In particular embodiments, the present invention provides methods of treating a patient with pancreatic cancer comprising; administering a SHH inhibitor, or other cancer stem cell inhibitor, to the patient such that the number of pancreatic stem cells expressing CD44, CD24 and ESA is reduced or eliminated in the subject.

In some embodiments, the present invention provides method for reducing the size of, or disk of obtaining, a pancreatic solid tumor, the method comprising: providing an agent directed against a SHH protein and contacting cells of the solid tumor, wherein the solid tumor comprises solid tumor stem cells, with a therapeutically effective amount of the agent. In particular embodiments, the solid tumor stem cells express CD44, CD24, and ESA.

BRIEF DESCRIPTION OF THE DRAWINGS/FIGURES

FIG. 1. Isolation of tumorigenic pancreatic cancer cells. Flow cytometry was used to isolate subpopulations of human pancreatic cancer cells which were tested for tumorigenicity in NOD/SCID mice. Cells were stained with antibodies against CD44, CD24, ESA, H2K and DAPI. Dead cells and mouse cells were eliminated from the 24 analyses. The plots depicted are representative examples of patterns of CD44 and ESA staining (top 3 plots) and CD24 and ESA staining (bottom 3 plots) of viable human pancreatic cancer cells from 3 individual patient xenografts, with the frequency of the boxed tumorigenic cancer cell population as a percentage of cancer cells in the specimen shown.

Figure 2:
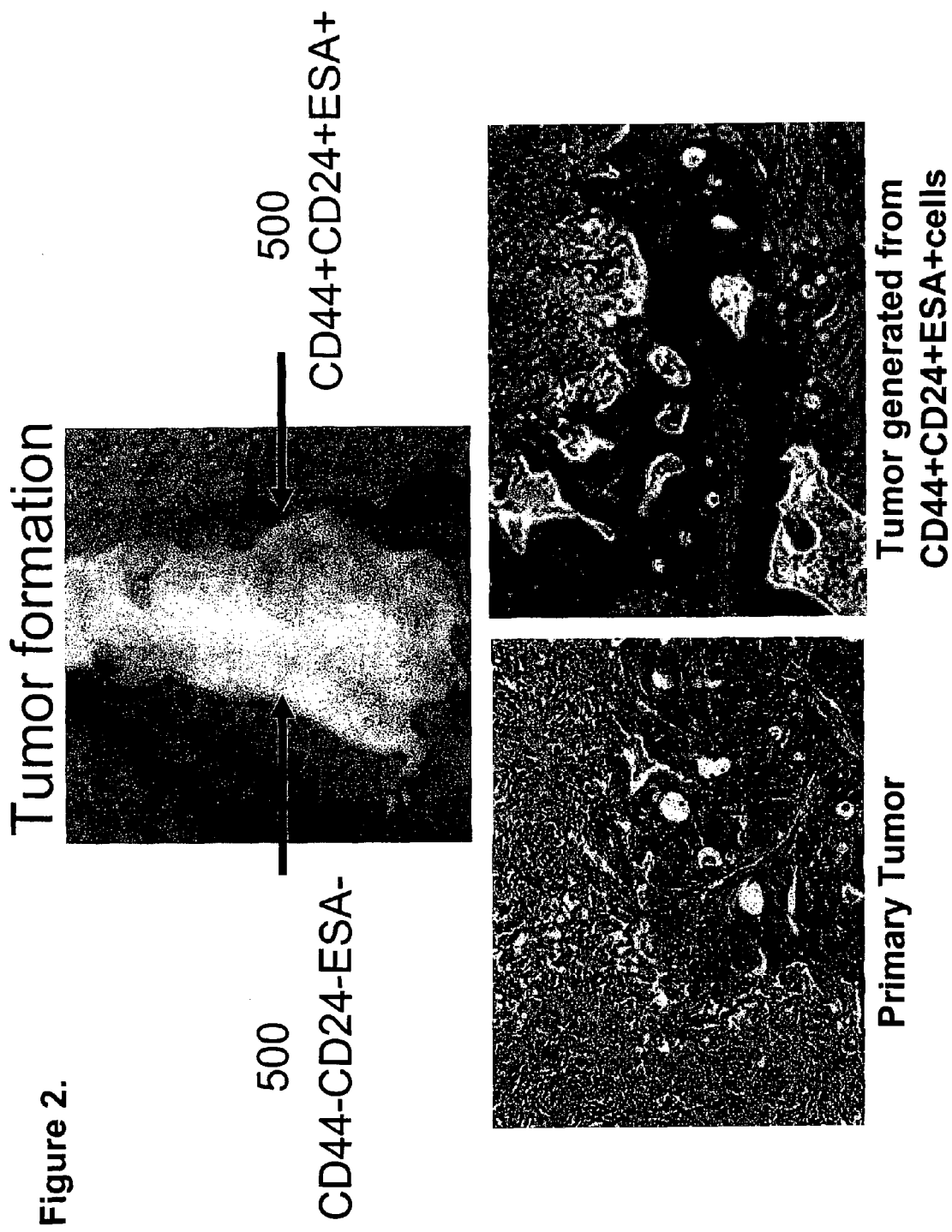

FIG. 2. Tumor formation in NOD/SCID mice injected with highly tumorigenic pancreatic cancer cells. A: A representative experiment depicting tumor formation in a mouse at the injection site of 500 CD44+CD24+ESA+ cells, with no tumor formation seen at the injection site of 500 CD44−CD24−ESA− cells. B. H & E staining of the tumor generated from CD44+CD24+ESA+ cells (right panel) has similar histologic features to the corresponding patient's primary pancreatic tumor (left panel). Magnification 200×.

Figure 3:
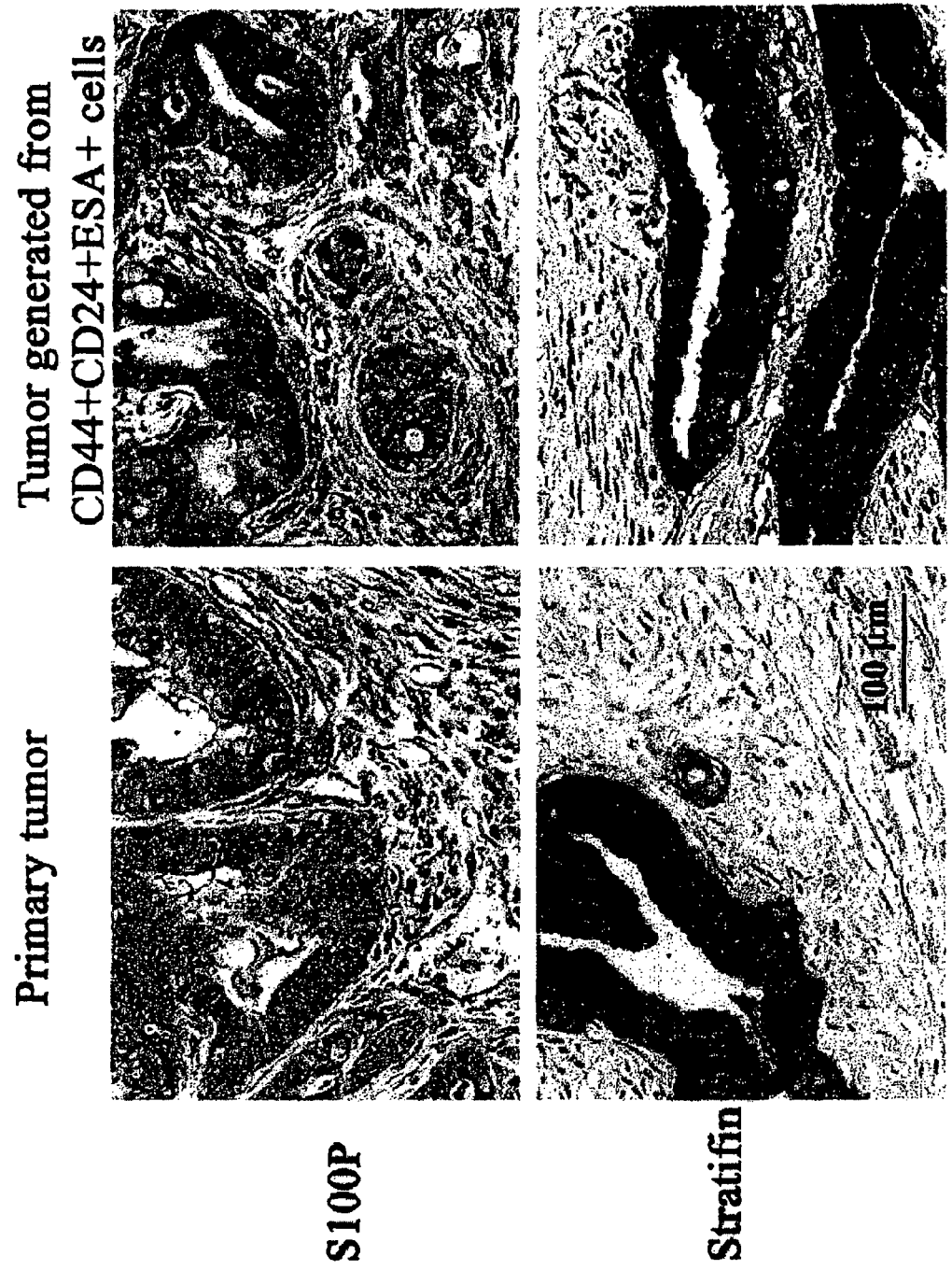

FIG. 3. Expression of differentiation markers in tumors derived from highly tumorigenic pancreatic cancer cells. Tissues were examined for the presence of S100P (top two panels) and stratifin (bottom two panels) in a primary patient tumor (left) and a tumor derived from CD44+CD24+ESA+ cells from the same patient. Antibody localization was performed using horseradish peroxidase, with dark brown staining indicating the presence of the specific antigen.

Figure 4:
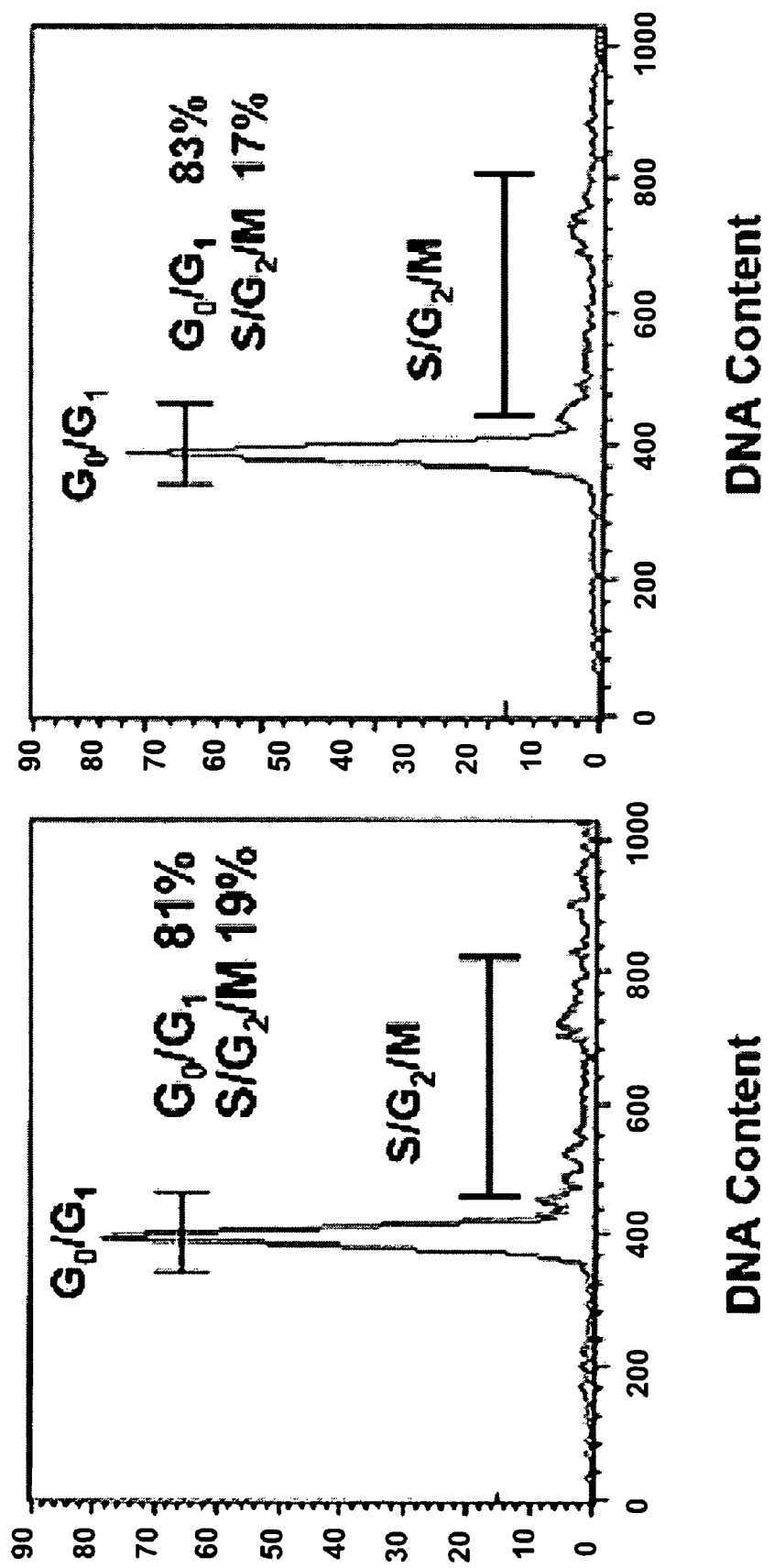

FIG. 4. Representative histogram of the DNA content of tumorigenic and nontumorigenic pancreatic cancer cells. The cell cycle status of CD44−CD24−ESA− cells (A) and CD44+CD24+ESA+ cells (B) was determined by propidium iodide staining of DNA content.

Figure 5:
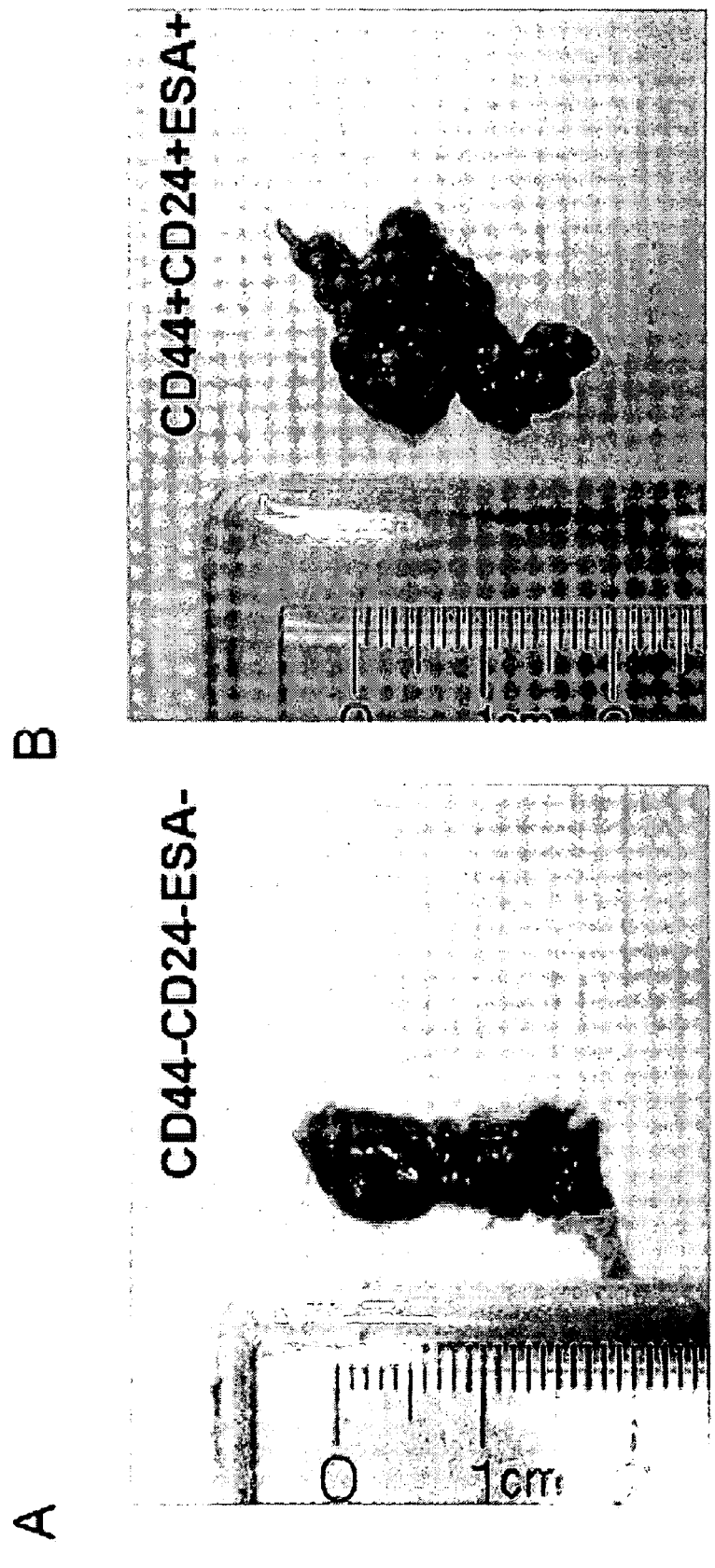

FIG. 5. CD44+CD24+ESA+ pancreatic cancer cells initiate tumors upon injection into the NOD/SCID mouse pancreatic tail. Mouse injected with 5000 CD44+CD24+ESA+ 25 pancreatic cancer cells demonstrates tumor formation 28 days following injection (right panel), while a tumor did not develop in the mouse injected with the same number of nontumorigenic cells (left panel).

Figure 6:
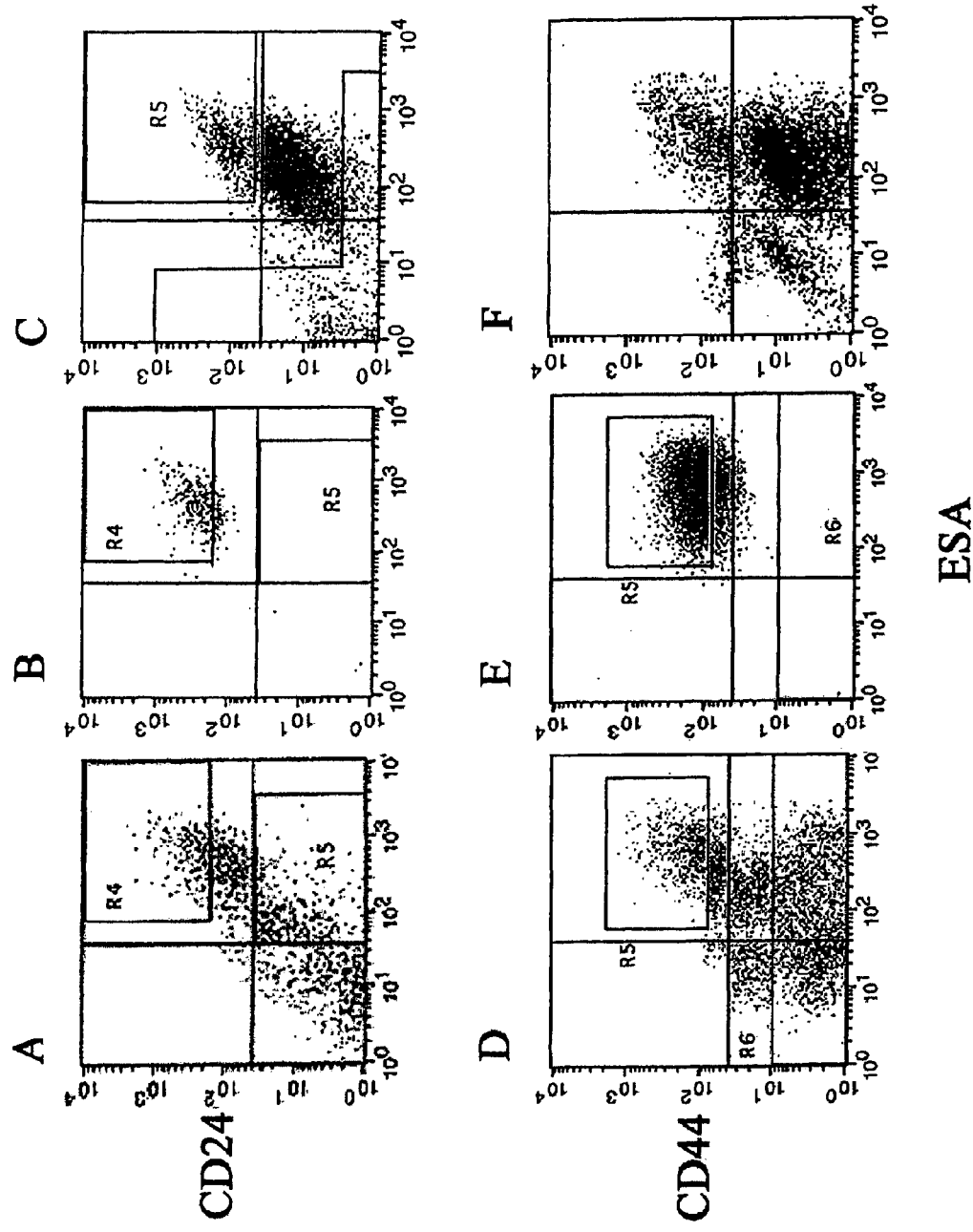

FIG. 6. Phenotypic diversity in tumors arising from CD44+CD24+ESA+ cells. The plots depict the CD44, CD24 and ESA staining patterns of human pancreatic cancer cells. The plot on the left (A and D) depicts that staining pattern from a patient tumor that had been passaged once in NOD/SCID mice. CD44+CD24+ESA+ tumorigenic cells from the tumor were then isolated (B and E) and injected into the flank of NOD/SCID mice. The right panel depicts the staining pattern of the resultant tumor that arose from the CD44+CD24+ESA+ cells. The tumorigenic cells formed tumors that contained phenotypically diverse cells (C and F) similar to those seen in the original tumor (A and D).

Figure 7:
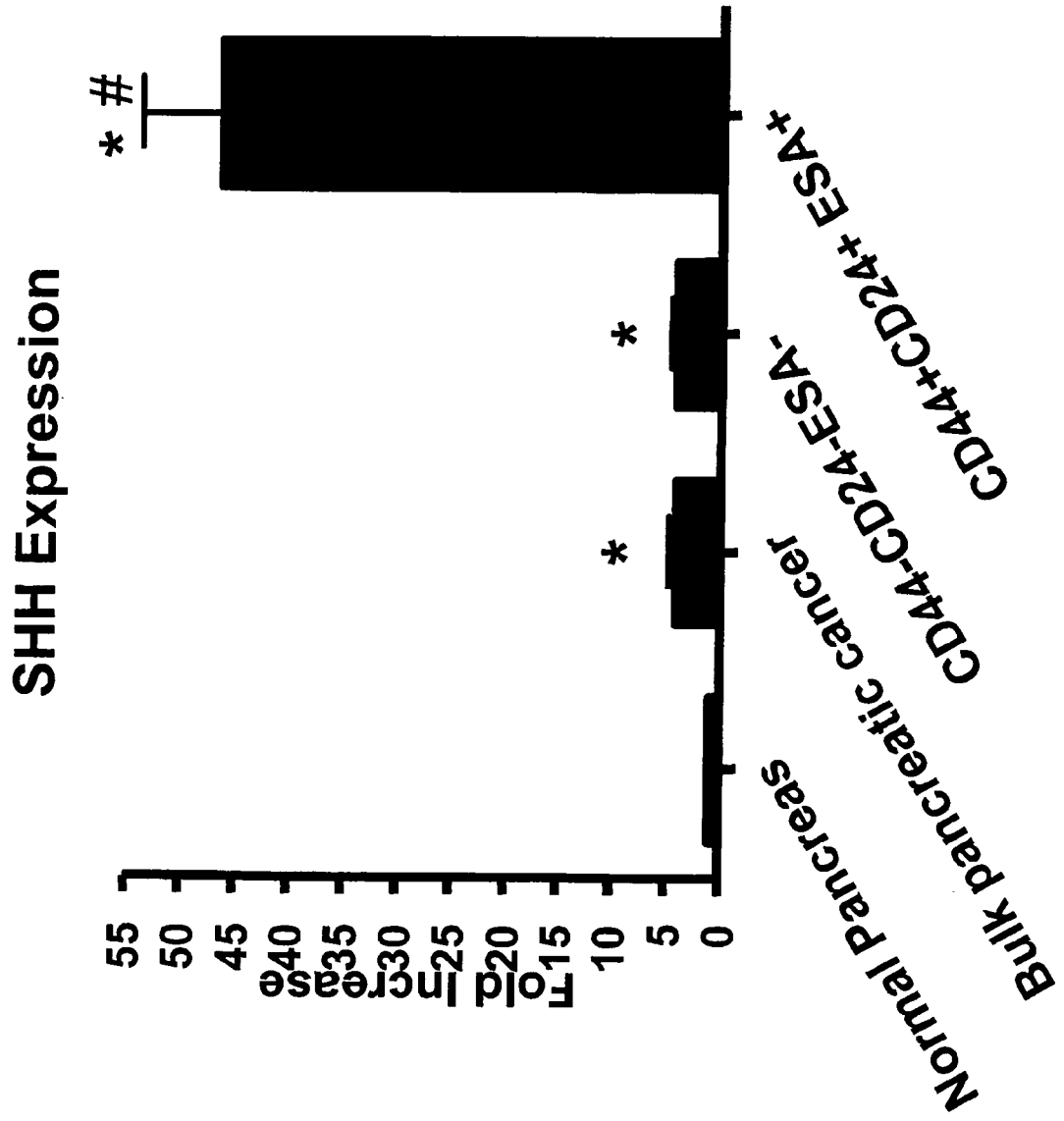

FIG. 7. mRNA expression of Sonic Hedgehog (SHH), important in developmental signaling pathways, in normal pancreas, bulk pancreatic cancer cells, nontumorigenic CD44−CD24−ESA− pancreatic cancer cells and highly tumorigenic CD44+CD24+ESA+ pancreatic cancer cells. Total RNA was isolated and mRNA was quantitated by real-time RT-PCR. Data are expressed as the mean+s.e.m. (*$p<0.05$ vs normal pancreas; #$p<0.05$ comparing CD44−CD24−ESA− to CD44+CD24+ESA+ cells).

DETAILED DESCRIPTION OF THE INVENTION

Emerging evidence has suggested that the capability of a tumor to grow and propagate is dependent on a small subset of cells within a tumor, termed cancer stem cells. While data has been provided to support this theory in human blood, brain, and breast cancers, the identity of pancreatic cancer stem cells has not been determined. Using a xenograft model in which primary human pancreatic adenocarcinomas were grown in immunocompromised mice, we identified a highly tumorigenic subpopulation of pancreatic cancer cells expressing the cell surface markers CD44, CD24, and ESA. Pancreatic cancer cells with the CD44+CD24+ESA+ phenotype (0.2-0.8% of pancreatic cancer cells) had a 100 fold increased tumorigenic potential compared to nontumorigenic cancer cells, with 50% of animals injected with as few as 100CD44+CD24+ESA+ cells forming tumors that were histologically indistinguishable from the human tumors from which they originated. The enhanced ability of CD44+CD24+ESA+ pancreatic cancer cells to form tumors was confirmed in anorthotopic pancreatic tail injection model. The CD44+CD24+ESA+ pancreatic cancer cells demonstrated the stem cell properties of self-renewal, the ability to produce differentiated progeny, and increased expression of the developmental signaling molecule sonic hedgehog. Identification of pancreatic cancer stem cells provides novel drug screening approaches and novel therapeutic approaches to treat pancreatic cancer, which is notoriously resistant to standard chemotherapy and radiation.

In one embodiment, the invention provides a method of selecting cells of a population to obtain a purified population of cancer stem cells (e.g. from a patient biopsy or from human tumor cells passaged via a xenograft in a mouse). The present invention also provides a method of selecting a purified population of tumor cells other than cancer stem cells, such as a population of non-tumorigenic (NTG) tumor cells. The present invention provides methods of raising antibodies to the selected cells. The invention provides diagnostic methods using the selected cells. The invention also provides therapeutic methods, where the therapeutic is directed to a cancer stem cell (e.g. directed to one of the cancer stem cell markers identified herein directly or indirectly).

The invention thus provides a method for selectively targeting diagnostic or therapeutic agents to pancreatic cancer stem cells. The invention also provides an agent, such as a biomolecule, that is selectively targeted to cancer stem cells (e.g. directed to one of the pancreatic cancer stem cell cancer markers disclosed herein). In some embodiments, the stem cell cancer marker targeted is part of a self-renewal or cell survival pathway. In certain embodiments, the present invention provides methods for screening for anti-cancer agents; for the testing of anti-cancer therapies; for the development of drugs targeting novel pathways; for the identification of new anti-cancer therapeutic targets; the identification and diagnosis of malignant cells in pathology specimens; for the testing and assaying of solid tumor stem cell drug sensitivity; for the measurement of specific factors that predict drug sensitivity; and for the screening of patients.

Other features, objects, and advantages of the invention will be apparent from the detailed description below. Additional guidance is provided in Published PCT patent application WO 02/12447 by the Regents of the University of Michigan and PCT patent application PCT/US02/39191 by the Regents of the University of Michigan, both of which are incorporated herein by reference.

To facilitate an understanding of the present invention, a number of terms and phrases are defined below:

An "antibody" is an immunoglobulin molecule that recognizes and specifically binds to a target, such as a protein, polypeptide, peptide, carbohydrate, polynucleotide, lipid, etc., through at least one antigen recognition site within the variable region of the immunoglobulin molecule. As used herein, the term is used in the broadest sense and encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies generated from at least two intact antibodies, fusion proteins comprising an antibody portion, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539 to Winter et al. (herein incorporated by reference).

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

That an antibody "specifically binds" to or shows "specific binding" towards an epitope means that the antibody reacts or associates more frequently, more rapidly, with greater duration, and/or with greater affinity with the epitope than with alternative substances. As used herein, "specifically binds" means that an antibody binds to a protein with a $K_D$ of at least about 0.1 mM, at least about 1 uM, at least about 0.1 uM or better, or 0.01 uM or better.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "receptor binding domain" refers to any native ligand for a receptor, including cell adhesion molecules, or any region or derivative of such native ligand retaining at least a qualitative receptor binding ability of a corresponding native ligand.

As used herein, the term "antibody-immunoadhesin chimera" comprises a molecule that combines at least one binding domain of an antibody with at least one immunoadhesin. Examples include, but are not limited to, the bispecific CD4-IgG chimeras described in Berg et al., PNAS (USA) 88:4723-4727 (1991) and Charnow et al., J. Immunol., 153:4268 (1994), both of which are hereby incorporated by reference.

"Enriched", as in an enriched population of cells, can be defined phenotypically based upon the increased number of cells having a particular marker (e.g. as shown in Table 1) in a fractionated set of cells as compared with the number of cells having the marker in the unfractionated set of cells. However, the term "enriched" can be defined functionally by tumorigenic function as the minimum number of cells that form tumors at limit dilution frequency in test mice. For example, if 500 tumor stem cells form tumors in 63% of test animals, but 5000 unfractionated tumor cells are required to form tumors in 63% of test animals, then the solid tumor stem cell population is 10-fold enriched for tumorigenic activity. The stem cell cancer markers of the present invention can be used to generate enriched populations of cancer stem cells. In some embodiments, the stem cell population is enriched at least 1.4 fold relative to unfractionated tumor cells. In other embodiments, the stem cell population is enriched 2 fold to 10 fold relative to unfractionated tumor cells. In further embodiments, the stem cell population is enriched 20 fold relative to unfractionated tumor cells.

"Isolated" in regard to cells, refers to a cell that is removed from its natural environment (such as in a solid tumor) and that is isolated or separated, and is at least about 30%, 50%, 75% free, or about 90% free, from other cells with which it is naturally present, but which lack the marker based on which the cells were isolated. The stem cell cancer markers of the present invention can be used to generate isolated populations of cancer stem cells.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, the cancer markers disclosed herein.

The terms "cancer stem cell", "tumor stem cell", or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells", "tumor stem cells" or "solid tumor stem cells" confer on those cancer stem cells the ability to form palpable tumors upon serial transplantation into an immunocompromised mouse compared to the majority of tumor cells that fail to generate tumors. Cancer stem cells undergo self-renewal versus differentiation in a chaotic manner to form tumors with abnormal cell types that can change over time as mutations occur. The solid tumor stem cells of the present invention differ from the "cancer stem line" provided by U.S. Pat. No. 6,004,528. In that patent, the "cancer stem line" is defined as a slow growing progenitor cell type that itself has few mutations but which undergoes symmetric rather than asymmetric cell divisions as a result of tumorigenic changes that occur in the cell's environment. This "cancer stem line" hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different than the "cancer stem line" model and as a result exhibits utilities not offered by the "cancer stem line" model. First, solid tumor stem cells are not "mutationally spared". The "mutationally spared cancer stem line" described by U.S. Pat. No. 6,004,528 can be considered a pre-cancerous lesion, while the solid tumor stem cells described by this invention are cancer cells that themselves contain the mutations that are responsible for tumorigenesis. That is, the solid tumor stem cells ("cancer stem cells") of the invention would be included among the highly mutated cells that are distinguished from the "cancer stem line" in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the "cancer stem line" model would predict that transplanted "cancer stem line" cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment), where they still form new tumors, distinguishes the present invention from the "cancer stem line" model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on the cancer stem cells of this invention the ability to form palpable tumors upon serial transplantation into an immunocompromised mouse compared to the majority of tumor cells that are unable to form tumors upon the serial transplantation. Tumor cells, i.e. non-tumorigenic tumor cells, may form a tumor upon transplantation into an immunocompromised mouse a limited number of times (for example one or two times) after obtaining the tumor cells from a solid tumor.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "unfractionated tumor cells", "presorted tumor cells", "bulk tumor cells", and their grammatical equivalents are used interchangeably to refer to a tumor cell population isolated from a patient sample (e.g. a tumor biopsy or pleural effusion) that has not been segregated, or fractionated, based on cell surface marker expression.

As used herein, the terms "non-tumorigenic tumor cells," "non-stem cells," "tumor cells" and their grammatical equivalents are used interchangeably to refer to a tumor population from which the cancer stem cells of this invention have been segregated, or removed, based on cell surface marker expression.

"Gene expression profile" refers to identified expression levels of at least one polynucleotide or protein expressed in a biological sample.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "high levels", "increased levels", "high expression", "increased expression", "elevated levels" or "upregulated expression" in regards to gene expression are used herein interchangeably to refer to expression of a gene in a cell or population of cells, particularly a cancer stem cell or population of cancer stem cells, at levels higher than the expression of that gene in a second cell or population of cells.

The term "undetectable levels" or "loss of expression" in regards to gene expression as used herein refers to expression of a gene in a cell or population of cells, particularly a cancer stem cell or population of cancer stem cells, at levels that cannot be distinguished from background using conventional techniques such that no expression is identified. "Undetectable levels" of gene expression can be determined by the inability to detect levels of a polynucleotide (mRNA, cDNA, etc.) in cancer stem cells above background by, for example, quantitative RT-PCR or microarray analysis. Alternatively "undetectable levels" of gene expression can be determined by the inability to detect levels of a protein in cancer stem cells above background by, for example, ELISA, Western blot, or immunofluorescence.

As used herein, the terms "low levels", "decreased levels", "low expression", "reduced expression" or "decreased expression" in regards to gene expression are used herein interchangeably to refer to expression of a gene in a cell or population of cells, particularly a cancer stem cell or population of cancer stem cells, at levels less than the expression of that gene in a second cell or population of cells, for example unfractionated pancreatic tumor cells.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous control" refers to measuring the level of expression of a gene (e.g., the level of mRNA or protein) relative to the level in a non-cancerous control sample. Gene expression can be measured using any suitable method, including but not limited to, those described herein.

As used herein, the term "detecting a change in gene expression in a cell sample in the presence of said test compound relative to the absence of said test compound" refers to measuring an altered level of expression (e.g., increased or decreased) in the presence of a test compound relative to the absence of the test compound. Gene expression can be measured using any suitable method.

As used herein, the term "instructions for using said kit for detecting cancer in said subject" includes instructions for using the reagents contained in the kit for the detection and characterization of cancer in a sample from a subject.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a tumor), information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

As used herein, the terms "providing a prognosis", "prognostic information", or "predictive information" refer to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "post surgical tumor tissue" refers to cancerous tissue (e.g., biopsy tissue) that has been removed from a subject (e.g., during surgery).

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer stem cells or for determining gene expression profile of that cancerous tissue. In some embodiment, biopsy tissue or fluid is obtained because a subject is suspected of having cancer. The biopsy tissue or fluid is then examined for the presence or absence of cancer, cancer stem cells, and/or cancer stem cell gene signature expression.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post-transcriptional cleavage and polyadenylation.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs can also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region can be present in a cDNA, genomic DNA or RNA form. When present in a DNA form, the oligonucleotide or polynucleotide can be single-stranded (i.e., the sense strand) or double-stranded. Suitable control elements such as enhancers/promoters, splice junctions, polyadenylation signals, etc. can be placed in close proximity to the coding region of the gene if needed to permit proper initiation of transcription and/or correct processing of the primary RNA transcript. Alternatively, the coding region utilized in the expression vectors of the present invention can contain endogenous enhancers/promoters, splice junctions, intervening sequences, polyadenylation signals, etc. or a combination of both endogenous and exogenous control elements.

As used herein the term "portion" when in reference to a nucleotide sequence (as in "a portion of a given nucleotide sequence") refers to fragments of that sequence. The fragments can range in size from four nucleotides to the entire nucleotide sequence minus one nucleotide (10 nucleotides, 20, 30, 40, 50, 100, 200, etc.).

The phrases "hybridizes", "selectively hybridizes", or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. to about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30-120 sec, an annealing phase lasting 30-120 sec, and an extension phase of about 72° C. for 1-2 min.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide can be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide can be single-stranded), but can contain both the sense and anti-sense strands (i.e., the oligonucleotide or polynucleotide can be double-stranded).

"Amino acid sequence" and terms such as "polypeptide", "protein", or "peptide" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein can be produced by recombinantly or can be isolated from a naturally occurring source.

As used herein the term "portion" when in reference to a protein (as in "a portion of a given protein") refers to fragments of that protein. The fragments can range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA can be cleaved with restriction enzymes prior to electrophoresis. Following electrophoresis, the DNA can be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies can be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and can include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

By "specific binding" or "unique binding" is intended when an agent binds only to a particular ligand, receptor, or antigen. By "selective binding" is intended when an agent preferably binds to a ligand, receptor, or antigen over others by a magnitude of about two-fold or great, about five-fold or greater, about eight-fold or greater, or about ten-fold or greater.

As used herein, "about" refers to plus or minus 10% of the indicated number. For example, "about 10%" indicates a range of 9% to 11%.

The present invention provides compositions and methods for treating, characterizing, and diagnosing cancer. In particular, the present invention provides gene expression profiles associated with solid tumor stem cells, as well as novel markers useful for the diagnosis, characterization, and treatment of solid tumor stem cells.

Detection of Solid Tumor Stem Cell Cancer Markers

In some embodiments, the present invention provides methods for detection of expression of stem cell cancer markers (e.g., pancreatic cancer stem cell cancer markers). In some embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In some embodiments, the presence of a stem cell cancer marker is used to provide a prognosis to a subject. The information provided is also used to direct the course of treatment. For example, if a subject is found to have a marker indicative of a solid tumor stem cell (e.g., CD44+, CD24+, and ESA+, and/or upregulation of SHH), additional therapies (e.g., radiation therapies) can be started at an earlier point when they are more likely to be effective (e.g., before metastasis). In addition, if a subject is found to have a tumor that is not responsive to certain therapy, the expense and inconvenience of such therapies can be avoided.

In some embodiments, the present invention provides a panel for the analysis of a plurality of markers. The panel allows for the simultaneous analysis of multiple markers correlating with carcinogenesis and/or metastasis. Depending on the subject, panels can be analyzed alone or in combination in order to provide the best possible diagnosis and prognosis. Markers for inclusion on a panel are selected by screening for their predictive value using any suitable method, including but not limited to, those described in the illustrative examples below.

1. Detection of RNA

In some embodiments, detection of solid tumor stem cell cancer markers are detected by measuring the expression of corresponding mRNA in a tissue sample (e.g., pancreatic cancer tissue). mRNA expression can be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe). A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

2. Detection of Protein

In other embodiments, gene expression of stem cell cancer markers is detected by measuring the expression of the corresponding protein or polypeptide. Protein expression can be detected by any suitable method. In some embodiments, proteins are detected by immunohistochemistry. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

3. cDNA Microarray Technology cDNA microarrays consist of multiple (usually thousands) of different cDNAs spotted (usually using a robotic spotting device) onto known locations on a solid support, such as a glass microscope slide. The cDNAs are typically obtained by PCR amplification of plasmid library inserts using primers complementary to the vector backbone portion of the plasmid or to the gene itself for genes where sequence is known. PCR products suitable for production of microarrays are typically between 0.5 and 2.5 kB in length. Full length cDNAs, expressed sequence tags (ESTs), or randomly chosen cDNAs from any library of interest can be chosen. ESTs are partially sequenced cDNAs as described, for example, in Hillier, et al., 1996, 6:807-828. Although some ESTs correspond to known genes, frequently very little or no information regarding any particular EST is available except for a small amount of 3' and/or 5' sequence and, possibly, the tissue of origin of the mRNA from which the EST was derived. As will be appreciated by one of ordinary skill in the art, in general the cDNAs contain sufficient sequence information to uniquely identify a gene within the human genome. Furthermore, in general the cDNAs are of sufficient length to hybridize, selectively, specifically or uniquely, to cDNA obtained from mRNA derived from a single gene under the hybridization conditions of the experiment.

In a typical microarray experiment, a microarray is hybridized with differentially labeled RNA, DNA, or cDNA populations derived from two different samples. Most commonly RNA (either total RNA or poly A+ RNA) is isolated from cells or tissues of interest and is reverse transcribed to yield cDNA. Labeling is usually performed during reverse transcription by incorporating a labeled nucleotide in the reaction mixture. Although various labels can be used, most commonly the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluorophore while cDNA derived from a second sample (representing, for example, a different cell type, tissue type, or growth condition) is labeled with the second fluorophore. Similar amounts of labeled material from the two samples are cohybridized to the microarray. In the case of a microarray experiment in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

Each microarray experiment can provide tens of thousands of data points, each representing the relative expression of a particular gene in the two samples. Appropriate organization and analysis of the data is of key importance, and various computer programs that incorporate standard statistical tools have been developed to facilitate data analysis. One basis for organizing gene expression data is to group genes with similar expression patterns together into clusters. A method for performing hierarchical cluster analysis and display of data derived from microarray experiments is described in Eisen et al., 1998, PNAS 95:14863-14868. As described therein, clustering can be combined with a graphical representation of the primary data in which each data point is represented with a color that quantitatively and qualitatively represents that data point. By converting the data from a large table of numbers into a visual format, this process facilitates an intuitive analysis of the data. Additional information and details regarding the mathematical tools and/or the clustering approach itself can be found, for example, in Sokal & Sneath, Principles of numerical taxonomy, xvi, 359, W. H. Freeman, San Francisco, 1963; Hartigan, Clustering algorithms, xiii, 351, Wiley, New York, 1975; Paull et al., 1989, J. Natl. Cancer Inst. 81:1088-92; Weinstein et al. 1992, Science 258:447-51; van Osdol et al., 1994, J. Natl. Cancer Inst. 86:1853-9; and Weinstein et al., 1997, Science, 275:343-9.

Further details of the experimental methods used in the present invention are found in the Examples. Additional information describing methods for fabricating and using microarrays is found in U.S. Pat. No. 5,807,522, which is herein incorporated by reference. Instructions for constructing microarray hardware (e.g., arrayers and scanners) using commercially available parts can be found at http://cmgm.stanford.edu/pbr-own/ and in Cheung et al., 1999, Nat. Genet. Supplement 21:15-19, which are herein incorporated by reference. Additional discussions of microarray technology and protocols for preparing samples and performing microrarray experiments are found in, for example, DNA arrays for analysis of gene expression, Methods Enzymol, 303:179-205, 1999; Fluorescence-based expression monitoring using microarrays, Methods Enzymol, 306: 3-18, 1999; and M. Schena (ed.), DNA Microarrays: A Practical Approach, Oxford University Press, Oxford, UK, 1999. Descriptions of how to use an arrayer and the associated software are found at http://cmgm.stanford.edu/pbrown/mguide/a-rrayerHTML/ArrayerDocs.html, which is herein incorporated by reference.

4. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data (e.g. examining a number of the markers), the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research use. For example, the data can be used to further optimize the inclusion or elimination of markers as useful indicators of a particular condition or stage of disease.

5. Kits

In yet other embodiments, the present invention provides kits for the detection and characterization of cancer (e.g. for detecting one or more of the markers, or for modulating the activity of a peptide expressed by one or more of markers). In some embodiments, the kits contain antibodies specific for a cancer marker, in addition to detection reagents and buffers. In other embodiments, the kits contain reagents specific for the detection of mRNA or cDNA (e.g., oligonucleotide probes or primers). In some embodiments, the kits contain all of the components necessary and/or sufficient to perform a detection assay, including all controls, directions for performing assays, and any necessary software for analysis and presentation of results.

Another embodiment of the present invention comprises a kit to test for the presence of the polynucleotides or proteins, e.g. in a tissue sample or in a body fluid, of a solid tumor stem cell gene signature, such as the alpha-catenin signature. The kit can comprise, for example, an antibody for detection of a polypeptide or a probe for detection of a polynucleotide. In addition, the kit can comprise a reference or control sample; instructions for processing samples, performing the test and interpreting the results; and buffers and other reagents necessary for performing the test. In certain embodiments the kit comprises a panel of antibodies for detecting expression of one or more of the proteins encoded by the genes of the alpha-catenin signature. In other embodiments the kit comprises pairs of primers for detecting expression of one or more of the genes of the solid tumor stem cell gene signature. In other embodiments the kit comprises a cDNA or oligonucleotide array for detecting expression of one or more of the genes of the solid tumor stem cell gene signature.

6. In Vivo Imaging

In some embodiments, in vivo imaging techniques are used to visualize the expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the solid tumor stem cell cancer markers of the present invention (e.g., in breast cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancer stem cells can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having pancreatic cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents can also be used, but the i-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement can be achieved by effecting radiolabeling in the presence of the specific stem cell cancer marker of the present invention, to insure that the antigen binding site on the antibody will be protected.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

Antibodies and Antibody Fragments

The present invention provides isolated antibodies against a cancer stem cell marker. The antibody, or antibody fragment, can be any monoclonal or polyclonal antibody that specifically recognizes the described pancreatic cancer stem cell marker. In some embodiments, the present invention provides monoclonal antibodies, or fragments thereof, that specifically bind to a pancreatic cancer stem cell marker polypeptide described herein. In some embodiments, the monoclonal antibodies, or fragments thereof, are chimeric or humanized antibodies that specifically bind to the extracellular domain of a pancreatic cancer stem cell marker polypeptide described herein. In other embodiments, the monoclonal antibodies, or fragments thereof, are human antibodies that specifically bind to the extracellular domain of a pancreatic cancer stem cell marker polypeptide described herein.

The antibodies against a cancer stem cell marker find use in the experimental, diagnostic and therapeutic methods described herein. In certain embodiments, the antibodies of the present invention are used to detect the expression of a pancreatic cancer stem cell marker protein in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a pancreatic cancer stem cell marker, for example, on tumor cells, in cell lysates, or in other protein samples. In other embodiments, the antibodies of the present invention are used to inhibit the growth of tumor cells by contacting the antibodies with tumor cells either in vitro cell based assays or in vivo animal models. In still other embodiments, the antibodies are used to treat cancer in a human patient by administering a therapeutically effective amount of an antibody against a pancreatic cancer stem cell marker.

Polyclonal antibodies can be prepared by any known method. Polyclonal antibodies can be raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against a pancreatic cancer stem cell marker is a humanized antibody. Humanized antibodies are antibodies that contain minimal sequences from non-human (e.g murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545, 806; 5,569,825; 5,625,126; 5,633,425; and 5,661,016.

This invention also encompasses bispecific antibodies that specifically recognize a pancreatic cancer stem cell marker.

Bispecific antibodies are antibodies that are capable of specifically recognizing and binding at least two different epitopes.

Bispecific antibodies can be intact antibodies or antibody fragments. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168).

In certain embodiments of the invention, it may be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from *E. coli* or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

It may further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies including $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

In some embodiments the antibody of the invention contains human Fc regions that are modified to enhance effector function, for example, antigen-dependent cell-mediated cyotoxicity (ADCC) and/or complement dependent cytotoxicity (CDC). This can be achieved by introducing one or more amino acid substitutions in an Fc region of the antibody. For example, cysteine residue(s) can be introduced in the Fc region to allow interchain disulfide bond formation in this region to improve complement-mediated cell killing and antibody-dependent cellular cytotoxicity (ADCC) (Caron et al., 1992, J. Exp Med. 176:1191-1195; Shopes, 1992, Immunol. 148:2918-2922). Homodimeric antibodies with enhanced anti-tumor activity can also be prepared using heterobifunctional cross-linkers as described in Wolff et al., 1993, Cancer Research 53:2560-2565. Alternatively, an antibody can be engineered which has dual Fc regions (Stevenson et al., 1989, Anti-Cancer Drug Design 3:219-230).

Drug Screening

In some embodiments, the present invention provides drug screening assays (e.g., to screen for anticancer drugs). The screening methods of the present invention utilize stem cell cancer markers identified using the methods of the present invention. For example, in some embodiments, the present invention provides methods of screening for compound that alter (e.g., increase or decrease) the expression of stem cell cancer marker genes. In some embodiments, candidate compounds are antisense agents or siRNA agents (e.g., oligonucleotides) directed against cancer markers. In other embodiments, candidate compounds are antibodies that specifically bind to a stem cell cancer marker of the present invention. In certain embodiments, libraries of compounds of small molecules are screened using the methods described herein.

In one screening method, candidate compounds are evaluated for their ability to alter stem cell cancer marker expression by contacting a compound with a cell expressing a stem cell cancer marker and then assaying for the effect of the candidate compounds on expression. In some embodiments, the effect of candidate compounds on expression of a cancer marker gene is assayed by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein. In some embodiments, other changes in cell biology (e.g., apoptosis) are detected.

Specifically, the present invention provides screening methods for identifying modulators, i.e., candidate or test compounds or agents (e.g., proteins, peptides, peptidomimetics, peptoids, small molecules or other drugs) which bind to, or alter the signaling or function associated with the cancer markers of the present invention, have an inhibitory (or stimulatory) effect on, for example, stem cell cancer marker expression or cancer markers activity, or have a stimulatory or inhibitory effect on, for example, the expression or activity of a cancer marker substrate. Compounds thus identified can be used to modulate the activity of target gene products (e.g., stem cell cancer marker genes) either directly or indirectly in a therapeutic protocol, to elaborate the biological function of the target gene product, or to identify compounds that disrupt normal target gene interactions. Compounds which inhibit the activity or expression of cancer markers are useful in the treatment of proliferative disorders, e.g., cancer, particularly metastatic cancer or eliminating or controlling tumor stem cells to prevent or reduce the risk of cancer.

In one embodiment, the invention provides assays for screening candidate or test compounds that are substrates of a cancer markers protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds can be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a stem cell cancer marker protein or biologically active portion thereof is contacted with a test compound, and the ability of the test compound to the modulate cancer marker's activity is determined. Determining the ability of the test compound to modulate stem cell cancer marker activity can be accomplished by monitoring, for example, changes in enzymatic activity. The cell, for example, can be of mammalian origin.

The ability of the test compound to modulate cancer marker binding to a compound, e.g., a stem cell cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the stem cell cancer marker is coupled with a radioisotope or enzymatic label to monitor the ability of a test compound to modulate cancer marker binding to a cancer markers substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a stem cell cancer marker substrate) to interact with a stem cell cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the stem cell cancer marker protein or biologically active portion thereof is evaluated. Biologically active portions of the cancer markers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the stem cell cancer markers protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. The target gene product can be anchored onto a solid surface, and the test compound, (which is not anchored), can be labeled, either directly or indirectly, with detectable labels discussed herein.

It may be desirable to immobilize stem cell cancer markers, an anti-cancer marker antibody or its target molecule to facilitate separation of complexed from non-complexed forms of one or both of the proteins, as well as to accommodate automation of the assay. Binding of a test compound to a stem cell cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with stem cell cancer marker protein or target molecules but which do not interfere with binding of the stem cell cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hage and Tweed J. Chromatogr. Biomed. Sci. Appl 699:499-525 [1997]). Further, fluorescence energy transfer can also be conveniently utilized, as described herein, to detect binding without further purification of the complex from solution.

The assay can include contacting the stem cell cancer markers protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer markers or biologically active portion thereof, or to modulate the activity of a target molecule, as compared to the known compound.

To the extent that stem cell cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent W0 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of stem cell cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease or cells from a cancer resulting from metastasis of a pancreatic cancer (e.g., to a lymph node, bone, or liver), or cells from a pancreatic cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein (e.g. to treat a human patient who has cancer).

Cancer Therapies

In some embodiments, the present invention provides therapies for cancer (e.g., pancreatic cancer). In some embodiments, therapies target cancer markers (e.g., including but not limited to, CD44, CD24, ESA and SHH upregulation). In some embodiments, any known or later developed cancer stem cell therapy may be used. For example, cancer stem cell therapeutic agents are described in U.S. Pat. Nos. 6,984,522 and 7,115,360 and applications WO03/050502, WO05/074633, and WO05/005601, herein incorporated by reference in their entireties. In some embodiments, the therapeutic agent is Cylopamine, a Cyclopamine analog, or siRNA molecules, or other antagonists (e.g., antibodies, peptides, small molecules, etc.) configured to disrupt the expression of Bmi-1, PTCH1, Thh, Gli1, Gli1, Bmi-1, or VEGF. In other embodiments, the therapeutic agent is siRNA molecules configured to disrupt the expression of Bmi-1 (for BMI-1 siRNA methods and materials, see Zencak et al., The Journal of Neuroscience, Jun. 15, 2005, 25(24):5774-5783, and Bracken et al., The EMBO Journal, Vol. 22, No. 20 pp. 5323-5335, 2003, both of which are herein incorporated by reference).

Antibody Therapy

In some embodiments, the present invention provides antibodies that target tumors that express a stem cell cancer marker of the present invention. Any suitable antibody (e.g., monoclonal, polyclonal, or synthetic) can be utilized in the therapeutic methods disclosed herein. In some embodiments, the antibodies used for cancer therapy are humanized antibodies. Methods for humanizing antibodies are well known in the art (See e.g., U.S. Pat. Nos. 6,180,370, 5,585,089, 6,054, 297, and 5,565,332; each of which is herein incorporated by reference).

In some embodiments, the therapeutic antibodies comprise an antibody generated against a stem cell cancer marker of the present invention, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention can include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments can include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some embodiments, deglycosylated ricin A chain is utilized.

In any event, it is proposed that agents such as these can, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a stem cell cancer marker of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In some embodiments, antibody based therapeutics are formulated as pharmaceutical compositions as described below. In some embodiments, administration of an antibody composition of the present invention results in a measurable decrease in cancer (e.g., decrease or elimination of tumor).

Pharmaceutical Compositions

The present invention further provides pharmaceutical compositions (e.g., comprising a small molecule, antisense, antibody, or siRNA that targets the stem cell cancer markers of the present invention). The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous or mixed media. Aqueous suspensions can further contain substances that increase the viscosity of the suspension including, for example, sodium carboxymethylcellulose, sorbitol and/or dextran. The suspension can also contain stabilizers.

In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level can also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention can additionally contain other adjunct components conventionally found in pharmaceutical compositions. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more compounds that modulate the activity of a stem cell caner marker (e.g. antibody, small molecule, siRNA, anti-sense, etc.) and (b) one or more other chemotherapeutic agents. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. Other chemotherapeutic agents are also within the scope of this invention. Two or more combined compounds can be used together or sequentially.

Dosing is dependent on severity and responsiveness of the disease state to be treated, with the course of treatment lasting from several days to several months, or until a cure is effected or a diminution of the disease state is achieved (e.g. reduction in tumor size). Optimal dosing schedules can be calculated from measurements of drug accumulation in the body of the patient. The administering physician can easily determine optimum dosages, dosing methodologies and repetition rates. Optimum dosages can vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and can be given once or more daily, weekly, monthly or yearly. The treating physician can estimate repetition rates for dosing based on measured residence times and concentrations of the drug in bodily fluids or tissues. Following successful treatment, it can be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

Transgenic Animals Expressing Cancer Marker Genes

The present invention contemplates the generation of transgenic animals comprising an exogenous cancer marker gene of the present invention or mutants and variants thereof (e.g., truncations or single nucleotide polymorphisms) or knock-outs thereof. In some embodiments, the transgenic animal displays an altered phenotype (e.g., increased or decreased presence of markers) as compared to wild-type animals. Methods for analyzing the presence or absence of such phenotypes include but are not limited to, those disclosed herein. In some embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., 1985, PNAS 82:4438-4442). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873, 191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, 1976, PNAS 73:1260). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., 1985, PNAS 82:6927). Transfection is easily and efficiently obtained by culturing the blastomeres on a monolayer of virus-producing cells (Stewart, et al., 1987, EMBO J., 6:383).

Alternatively, infection can be performed at a later stage. Virus or virus-producing cells can be injected into the blastocoele (Jahner et al., 1982, Nature 298:623). Most of the founders will be mosaic for the transgene since incorporation occurs only in a subset of cells that form the transgenic animal. Further, the founder can contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, 1995, Mol. Reprod. Dev., 40:386).

In other embodiments, the transgene is introduced into embryonic stem cells and the transfected stem cells are utilized to form an embryo. ES cells are obtained by culturing pre-implantation embryos in vitro under appropriate conditions (Evans et al., 1981, Nature 292:154; Bradley et al., 1984, Nature 309:255; Gossler et al., 1986, PNAS 83:9065; and Robertson et al., 1986, Nature 322:445). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science, 1988, 240:1468). Prior to the introduction of transfected ES cells into the blastocoel, the transfected ES cells can be subjected to various selection protocols to enrich for ES cells which have integrated the transgene assuming that the transgene provides a means for such selection. Alternatively, the polymerase chain reaction can be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles);

μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); i.p. (intraperitoneal); HBSS (Hepes buffered saline solution); FCS (fetal calf serum); FBS (fetal bovine serum).

Example 1

Identification and Isolation of Pancreatic Solid Tumor Stem Cells

Methods

Primary Tumor Specimen Implantation. Samples of human pancreatic adenocarcinomas were obtained within 30 minutes following surgical resection according to IRB-approved guidelines. Tumors were suspended in sterile RPMI medium 1640 and mechanically dissociated using scissors, then minced with a sterile scalpel blade over ice to yield 2×2 mm pieces. The tumor pieces were washed with serum-free PBS before implantation. Eight-week-old male NOD/SCID mice were anesthetized using an i.p. injection of 100 mg/kg ketamine and 5 mg/kg xylazine. A 5-mm incision was then made in the skin overlying the mid-abdomen, and three pieces of tumor were implanted subcutaneously. The skin incision was closed with absorbable suture. The mice were monitored weekly for tumor growth for 16 weeks.

Preparation of Single Cell Suspensions of Tumor Cells. Before Digestion with collagenase, xenograft tumors or primary human tumors were cut up into small pieces with scissors, and then minced completely using sterile scalpel blades. To obtain single cell suspensions, the resultant minced tumor pieces were mixed with ultra-pure collagenase IV (Worthington Biochemicals) in medium 199 (200 units of collagenase per ml) and allowed to incubate at 37° C. for 2.5-3 h for enzymatic dissociation. The specimens were further mechanically dissociated every 15 to 20 minutes by pipetting with a 10-ml pipette. At the end of the incubation, cells were filtered through a 40-μm nylon mesh and washed with HBSS/ 20% FBS, then washed twice with HBSS.

Flow Cytometry. Dissociated cells were counted and transferred to a 5-ml tube, washed twice with HBSS containing 2% heat-inactivated FBS, and resuspended in HBSS with 2% FBS at concentration of $10^6$ cells per 100 μl. Sandoglobin solution (1 mg/ml) was then added to the sample at a dilution of 1:20 and the sample was incubated on ice for 20 min. The sample was then washed twice with HBSS/2% FBS and resuspended in HBSS/2% FBS. Antibodies were added and incubated for 20 min on ice, and the sample was washed twice with HBSS/2% FBS. When needed, a secondary antibody was added by resuspending the cells in HBSS/2% FBS, followed by a 20-min incubation. After another washing, cells were resuspended in HBSS/2% FBS containing DAPI (1 μg/ml final concentration). The antibodies used were anti-CD44 allophycocyanin (APC), anti-CD24 (PE), and anti-H2K (PharMingen, Franklin Lakes, N.J.), and anti-epithelial-specific antigen (ESA)-FITC (Biomeda, Foster City, Calif.), each at a dilution of 1:40. In all experiments using human xenograft tissue, infiltrating mouse cells were eliminated by discarding H2K (mouse histocompatibility class I) cells during flow cytometry. Dead cells were eliminated by using the viability dye DAPI. Flow cytometry was performed using a FACS Aria (BD Immunocytometry Systems, Franklin Lakes, N.J.). Side scatter and forward scatter profiles were used to eliminate cell doublets. Cells were routinely sorted twice, and the cells were reanalyzed for purity, which typically was greater than 97%.

Sorted Cell Implantation into NOD/SCID Mice. Sorted cells were washed with serum free HBSS after flow cytometry and suspended in serum free-RPMI/Matrigel mixture (1:1 volume), followed by injection subcutaneously into the right and left mid-abdominal area using a 23-gauge needle. In separate experiments, mice were anesthetized with an i.p. injection of 100 mg/kg ketamine and 5 mg/kg xylazine, a median laparotomy was done and either 1,000 or 5,000 sorted cells (CD44+CD24+ESA+ vs CD44−CD24−ESA−) were resuspended in PBS in a volume of 100 μl were injected into the tail of the pancreas using 30-gauge needle (n=3 animals per group). Animals underwent autopsy at 28 days after cell implantation and tumor growth was accessed. Tissues were fixed in formaldehyde and examined histologically.

Immunohistochemistry. Tissue samples were fixed in 10% phosphate-buffered formalin, and embedded in paraffin. Formalin-fixed, paraffin-embedded sections were cut 4 μm-thick, mounted on poly-L-lysine-coated slides (Sigma), and dried overnight at 37° C. Sections were then dewaxed in xylene, rehydrated according to standard histopathologic procedures, and stained with H&E. Immunodetection was done using the ChemMate Detection Kit (peroxidase/3,3'-diaminobenzidine, rabbit/mouse (DakoCytomation, Carpinteria, Calif.)). Detection of expression levels of S100P and stratifin in sections of a primary tumor and the subsequent tumor derived from CD44+CD24+ESA+ sorted cells was performed as we described previously (14,15).

Cell Cycle Analysis. For cell cycle analysis by flow cytometry, cells were fixed with 70% ethanol overnight at 4° C. Cell pellets were then suspended in 300 μl PBS containing 10 μg/ml propidium iodide (Calbiochem, San Diego, Calif.) and 100 μg/ml RNase to stain nuclear DNA for 30 min at room temperature. DNA content was analyzed using a Becton Dickinson FACScan flow cytometer (Becton Dickinson, San Jose, Calif.). The distribution of cells in the different phases of the cell cycle was analyzed from DNA histograms using BD CELLQuest software (Becton Dickinson). Cell cycle analysis was performed on CD44−CD24−ESA− and CD44+CD24+ESA+ cells from three separate pancreatic cancer xenografts.

Real time RT-PCR. To assess expression levels of sonic hedgehog, 3 samples of normal pancreas and 3 separate samples of pancreatic cancer xenografts were used. Samples of normal human pancreas used as controls were obtained from organ donors provided by the Michigan Transplantation Society and processed similar to samples of pancreatic adenocarcinoma. Single cell suspensions of the samples were prepared, and ESA+ normal pancreatic cells, bulk pancreatic cancer cells, and sorted CD44−CD24−ESA− and CD44+CD24+ESA+ pancreatic cancer cells were used. For real-time RT-PCR analysis, cDNA was first synthesized using equivalent amounts of total RNA (0.5-1 μg) with random primers in a 20 μl reverse-transcriptase reaction mixture (Promega). Real time quantitative RT-PCR (Taqman) primers were designed and purchased from Applied Biosystems as Assay-on-Demand™ Gene Expression Products. Real-time RT-PCRs were performed following the supplier's directions. 20 μl of PCR mixture contained 10 μl of 2× Taqman™ universal PCR master mix, 1 μl of 20× working stock of expression assay mix, and 50 ng of RNA converted DNA. Real time PCRs were performed in a ABI PRISM 7900HT sequencing detection system (Applied Biosystems). The reaction for each sample was performed in triplicate. Fluorescence of the PCR products was detected by same apparatus. The number of cycles that it takes the for amplification plot to reach the threshold limit, the Ct-value, was used for quantification. Ribosomal protein S6 (RPS6) was used for normalization.

Statistical analysis. Data are expressed as the mean±sem. Statistically significant differences were determined by Student's t test and chi square analysis where appropriate and were defined as p<0.05.

Results Establishment of Xenografts from Human Pancreatic Tumors. A total number of 10 human pancreatic adenocarcinoma xenografts were established, 8 from primary tumors, and 2 from metastatic lesions (Table 1).

TABLE 1

Engraftment of human pancreatic cancers into NOD/SCID mice

| Tumor | Origin | Mice Tumor Formation | Passage in Mice | Diagnosis |
|---|---|---|---|---|
| No. 1 | Primary tumor | yes | yes | adenocarcinoma |
| No. 2 | Primary tumor | yes | yes | adenocarcinoma |
| No. 3 | Metastasis | yes | yes | adenocarcinoma |
| No. 4 | Primary tumor | yes | yes | adenocarcinoma |
| No. 5 | Primary tumor | yes | yes | adenocarcinoma |
| No. 6 | Metastasis | yes | yes | adenocarcinoma |
| No. 7 | Primary tumor | yes | yes | adenocarcinoma |
| No. 8 | Primary tumor | yes | yes | adenocarcinoma |
| No. 9 | Primary tumor | yes | yes | adenocarcinoma |
| No. 10 | Primary tumor | yes | yes | adenocarcinoma |

Mice were injected with unsorted primary pancreatic adenocarcinomas minced into 2 mm pieces. Cells from all 10 xenografts and one primary tumor were isolated by flow cytometry as described in FIG. 1. All of the tumors were primary pancreatic tumors, except No. 3 and No. 6, which were metastases. All of the tumors were passaged serially in mice.

Xenografts are important for these types of studies because of the difficulty in routinely obtaining primary tumors from the pancreas. The validity of using xenografts is supported by previous work demonstrating that pancreatic cancer xenografts retain many of the features of the primary tumor upon multiple passaging (16). The initial engraftment rate with implantation of 3, 2×2 mm minced pieces of a pancreatic cancer into a single site in a NOD/SCID mouse was 25-30%. Changing this approach to implantation of 3 minced pieces bilaterally into the midabdomen of 4 separate NOD-SCID mice resulted in an improvement of the engraftment rate of individual tumors to 100%. We did not observe an improvement in the rate of engraftment with pretreatment of mice with VP16 (etoposide) given via i.p injection (30 mg dose per 1 kg mouse) for 5 days prior to implantation, as has been observed in studies of human breast cancer xenografts (5). After establishment of xenografts, studies were performed on passage 1-2 of tumors. Results were compared to those obtained from a freshly sorted primary tumor.

Tumor-Initiating Capability of Sorted Pancreatic Cancer Cells. To test the hypothesis that there is a small subpopulation of distinct, highly tumorigenic pancreatic cancer cells within a human pancreatic cancer that is responsible for tumor formation, xenografts were digested with ultra-pure collagenase IV, followed by sorting for the markers CD44, CD24, and ESA, both individually or in combination. Flow cytometric quantification of CD44, CD24, and ESA expression was performed on one acutely dissociated tumor and 10 tumor xenografts. Sorted cells were then suspended in a Matrigel mixture (1:1) and subcutaneously injected into NOD/SCID mice. Tumor growth was monitored weekly for 16 weeks, at which time animals were sacrificed and tumor absence or presence confirmed by histological examination. The markers CD44, CD24, and ESA were chosen as a starting point based on prior work on breast cancer stem cells, in which ESA+CD24−/low CD44+ cells generated tumors histologically similar to primary breast tumors when as few as 100 cells were transplanted, while tens of thousands of bulk unsorted cancer cells were needed to form tumors in NOD-SCID mice (5). ESA, CD44, and CD24 have been identified as stem cell surface markers which act as adhesion molecules with multiple signaling functions (17-19).

Depending on the individual tumor, 2-9% of sorted human pancreatic cancer cells expressed the cell surface marker CD44, 3-28% expressed CD24, and 11-70% expressed 11 ESA. When examining expression of multiple surface markers, 1-16.9% of sorted cells were CD44+ESA+, 1.8-23% were CD24+ESA+, and 0.5-2% were CD44+CD24+, while only 0.2-0.8% of cells were CD44+CD24+ESA+. Several examples of CD44+/CD24+/ESA+ sorted tumor cells from individual patients are shown in FIG. 1. The percentage of cancer cells expressing these cell surface markers in individual tumors was maintained upon passaging. The percentage of cells expressing CD44, CD24, and ESA in the freshly dissociated tumor and xenografts derived from that tumor were similar.

In a dose response of unsorted pancreatic cancer cells (100-$10^4$) injected per mouse, no tumor growth was evident at 16 weeks unless at least $10^4$ cells were injected, where four out of 6 mice developed tumors (see top of Table 2). For cancer cells sorted for the markers CD44, CD24, and ESA, expression of individual markers identified cell populations with enhanced tumorigenic potential (Table 2).

TABLE 2

Tumor formation ability of sorted pancreatic cancer cells using single cell surface markers

| | Cell Number | | | |
|---|---|---|---|---|
| | $10^4$ | $10^3$ | 500 | 100 |
| unsorted | 4/6 | 0/6 | 0/3 | 0/3 |
| CD44+ | 8/16* | 7/16* | 5/16 | 4/16* |
| CD44− | 2/16 | 1/16 | 1/16 | 0/16 |
| | (*p = .022) | (*p = .014) | (p = .07) | (*p = .03) |
| ESA+ | 12/18* | 13/18* | 8/18* | 0/18 |
| ESA− | 3/18 | 1/18 | 1/18 | 0/18 |
| | (*p = .002) | (*p = .0001) | (*p = .007) | (N/A) |
| CD24+ | 11/16* | 10/16* | 7/16* | 1/16 |
| CD24− | 2/16 | 1/16 | 0/16 | 0/16 |
| | (*p = .001) | (*p = .001) | (*p = .003) | (p = .31) |

Cells were isolated by flow cytometry as described in FIG. 1 based on expression of the indicated marker and assayed for the ability to form tumors after injection into the subcutaneum of the flank of NOD/SCID mice at 100, 500, $10^3$, and $10^4$ cells per injection. Mice were examined weekly for 16 weeks for tumor formation by palpation. At the completion of 16 weeks, all mice underwent autopsy to look for tumor formation at the injection sites that was too small to palpate. The number of tumors formed/number of injections that were performed are indicated for each population. P values are listed comparing tumor formation for each marker at different cell dilutions. P values <0.05 compared to results with marker negative cells are highlighted with an asterisk*.

For example, injection of 100 CD24+ cells would occasionally form a tumor (1/16 animals), while no tumors were observed with CD24− cells until at least $10^3$ cells were injected (1/16 animals), while 10/16 animals developed tumors when injected with $10^3$ CD24+ cells, representing at least a ten-fold increase in tumorigenic potential compared to marker negative cells (p=0.001). Similar results were obtained with CD44+ and ESA+ cells, with cells expressing CD44+ demonstrating the highest tumorigenic potential, with 4/16 animals developing tumors when injected with as few as 100 cells. Injection of cancer cells expressing dual marker combinations (CD44+ESA+, CD24+ESA+, CD44+CD24+) resulted in an enhanced tumorigenic potential compared to single marker sorted cells, with more tumors forming with injection of as few as 100 cells, and no tumors forming in 12 marker negative cells until at least $10^3$ cells were injected (Table 3). The sorted cell population with the highest tumorigenic potential were those cells expressing CD44, CD24, and ESA, where 6/12 animals injected with 100 CD44+CD24+ESA+ cells formed tumors, and cells negative for expression of these cell surface markers did not develop any tumors until $10^4$ CD44−CD24−ESA− cells were injected, when only 1/12 animals developed a tumor (Table 3).

TABLE 3

Tumorigenic pancreatic cancer cells were highly enriched in the CD44+CD24+ESA+ population

| | Cell number | | | |
|---|---|---|---|---|
| | $10^4$ | $10^3$ | 500 | 100 |
| CD44+ESA+ | 9/16* | 10/16* | 7/16* | 4/16* |
| CD44−ESA− | 3/16 | 2/16 | 0/16 | 0/16 |
| | (*p = .03) | (*p = .004) | (*p = .003) | (*p = .033) |
| CD24+ESA+ | 6/8* | 5/8* | 5/8* | 2/8 |
| CD24−ESA− | 2/8 | 1/8 | 0/8 | 0/8 |
| | (*p = .05) | (*p = .04) | (*p = .007) | (p = .13) |
| CD44+CD24+ | 6/8* | 5/8* | 4/8* | 2/8 |
| CD44−CD24− | 1/8 | 1/8 | 0/8 | 0/8 |
| | (*p = .01) | (*p = .04) | (*p = .02) | (p = .13) |
| CD44+CD24+ESA+ | 10/12* | 10/12* | 7/12* | 6/12* |
| CD44−CD24−ESA− | 1/12 | 0/12 | 0/12 | 0/12 |
| | (*p = .0002) | (*p = .0001) | (*p = .001) | (*p = .004) |

Cells were isolated by flow cytometry as described in FIG. 1 based on expression of the combinations of the indicated markers and assayed for the ability to form tumors after injection into the subcutaneum of the flank of NOD/SCID mice at 100, 500, $10^3$, and $10^4$ cells per injection. Mice were examined for tumor formation by palpation and subsequent autopsy. The analysis was completed 16 weeks following injection. Data is expressed as number of tumors formed/number of injections. P values are listed comparing tumor formation for each marker at different cell dilutions. P values <0.05 compared to results with marker negative cells are highlighted with an asterisk*.

Thus pancreatic cancer cells expressing the cell surface markers CD44, CD24, and ESA had at least a 100 fold increased tumorigenic potential compared to nontumorigenic cells. Findings were similar for all tumors tested, including cells derived from the freshly sorted tumor and the xenografts. We did observe that the tumors that developed from the nontumorigenic cells tended to be smaller and to develop more slowly than tumors that developed from tumorigenic cells. This may be accounted for by the reduced proliferative capacity of the nontumorigenic cells, or due to the 1-3% of tumorigenic cells that invariably contaminate the nontumorigenic cells.

Histologically, the tumors derived from the highly tumorigenic pancreatic cancer cells appeared remarkably similar to histological sections of the patient's primary tumor. An example of this is shown in FIG. 2 from a representative mouse injected with 500 CD44−CD24−ESA− cells on the left side of the abdomen and 500 CD44+CD24+ESA+ cells on the right side of the abdomen. Hematoxylin and eosin staining of the tumor generated from the CD44+CD24+ESA+ cells demonstrates epithelial cancer cells and is phenotypically indistinguishable from the patient's primary tumor. Tumors derived from highly tumorigenic pancreatic cancer cells also expressed differentiation markers typically seen in pancreatic adenocarcinoma, as shown in FIG. 3, where both the primary tumor and the tumor derived from that patient's CD44+CD24+ESA+ sorted cells had morphological characteristics similar to the patient's primary tumor and expressed the differentiation markers S100P and stratifin. These differentiation markers are known to be expressed in the majority of human pancreatic adenocarcinomas (14,15).

To determine whether differences in tumorigenicity observed between CD44+CD24+ESA+ and CD44−CD24−ESA− cells were due to differences in cell cycle distribution, we analyzed cell cycle distribution by flow cytometry from cells isolated from 3 different xenografts (FIG. 4). We did not observe any differences in cell cycle distribution between the highly tumorigenic and nontumorigenic populations, demonstrating that neither cell population was enriched for cells at a particular stage of the cell cycle.

The biologic function of stem cells has been shown to be highly dependent on the local tissue environment, or the niche (20). To further validate our findings of the tumorigenic potential of the pancreatic cancer cells based on cell surface marker expression, we tested the tumorigenic potential of CD44+CD24+ESA+ cells and CD44−CD24−ESA cells when injected directly into the pancreas. Either 1000 or 5000 CD44+CD24+ESA+ or CD44−CD24−ESA− pancreatic cancer cells were injected into the mouse pancreatic tail and tumor formation was monitored weekly for 4 weeks (n=3 animals per group). At 4 weeks, the animals were sacrificed and tumor formation was assessed. In animals injected with 5000 CD44+CD24+ESA+ cells, macroscopic tumors were evident in 2 out of 3 mice, while none were observed in animals injected with CD44−CD24−ESA− cells (FIG. 5). Tumor formation was confirmed with histologic analysis (data not shown). These results further support the enhanced tumorigenic potential of CD44+CD24+ESA+ pancreatic cancer cells in the pancreatic niche.

The Tumorigenic Cancer Cell Population Generates the Phenotypic Diversity of the Initial Tumor. Normal stem cells are defined by their ability to both self renew and generate phenotypically diverse progeny. To test if our highly tumorigenic cancer cells also exhibited these properties, CD44+CD24+ESA+ cells (FIG. 6, panel B, E) were injected into mice and the resultant tumors analyzed. The pattern of CD44, CD24 and ESA expression evident in the secondary tumors (FIG. 6, panel C, F) was similar to that which was observed in the tumor from which they were derived (FIG. 6, panel A, D). The highly tumorigenic CD44+CD24+ESA+ cells gave rise to additional CD44+CD24+ESA+ cells as well as phenotypically diverse nontumorigenic cells, demonstrating the same phenotypic complexity as the primary tumor from which the tumorigenic cells were derived. The tumors have now been passaged through 4 rounds of tumor formation in mice, and similar results have been observed, with no evidence of decrease in the tumorigenicity of the CD44+CD24+ESA+ cells (data not shown). These data indicates that CD44+CD24+ESA+ pancreatic cancer cells act as cancer stem cells, capable of undergoing both the processes of self-renewal and creation of differentiated progeny.

Self-Renewal Pathways Are Upregulated in Pancreatic Cancer Stem Cells. A number of developmental signaling molecules have been implicated in the self-renewal process of normal stem cells, including Bmi-1, Notch, hedgehog, PTEN, and Wnt (21-24). Deregulation of these signaling molecules has been associated with tumorigenesis, both in human and rodent models (21, 25-27). In the pancreas, aberrant expression of Sonic hedgehog (SHH) using a Pdx-1 promoter has been found to produce precursor lesions to pancreatic cancer, termed PanIN lesions, and to develop similar genetic changes to pancreatic adenocarcinoma (28). Furthermore, human pancreatic adenocarcinomas display increased hedgehog pathway activity (29). We next determined if there was increased expression of the developmental signaling molecule SHH in our highly tumorigenic pancreatic cancer cell population. Real-time quantitative RT-PCR was performed using 3 samples of normal pancreas and 3 separate pancreatic cancer xenografts. For normal pancreas, a single cell suspension of ESA+ cells was used so that the epithelial cell population within the pancreas served as a control. Experimental samples included single cell suspensions of bulk pancreatic cancer cells, CD44−CD24−ESA− cells, and CD44+CD24+ESA+ cells. We found that SHH expression was upregulated 4.1 fold in bulk pancreatic cancer cells, 4.0 fold in CD44−CD24−ESA− cells, and 46.3 fold in CD44+CD24+ESA+ cells compared to normal pancreatic epithelial cells (FIG. 7), suggesting that SHH is markedly upregulated in pancreatic cancer stem cells.

Discussion

In this Example, we have identified a subpopulation of highly tumorigenic cancer cells within human pancreatic adenocarcinomas using a xenograft model in which primary human pancreatic adenocarcinoma cells were implanted in immunocompromised mice. These highly tumorigenic cancer cells were identified by expression of the cell surface markers CD44, CD24, and ESA. These cells displayed several features typically seen in stem cells, including the ability to both self-renew and generate differentiated progeny, the ability to differentiate to recapitulate the phenotype of the tumor from which they were derived, and activation of developmental signaling pathways.

We found that cells that expressed CD44, CD24, and ESA represented the most highly tumorigenic population of pancreatic cancer cells, with injection of as few as 100 triple positive CD44+CD24+ESA+ cells resulting in tumor formation in 6/12 of animals, a 100 fold enhanced tumorigenic potential compared to nontumorigenic cells. These markers we found to characterize a highly tumorigenic population that was distinct from those observed in human breast cancer, where in 8/9 patients, the phenotype of the breast cancer stem cell was ESA+CD44+CD24−/low. Interestingly, in one breast cancer patient studied, the tumorigenic cancer cell population was CD44+CD24+ESA+. This patient had a particularly virulent subtype of breast cancer, a comedo-type adenocarcinoma of the breast, and in this cancer more than 66% of the cells were contained in the tumorigenic fraction (5). While the correlation between ESA and CD24 expression and cancer stem cell function has not been examined in other tumor types, CD44+ cells have been shown to define a highly tumorigenic cancer cell population in prostate cancer cells with stem cell like characteristics (9). Other cell surface markers define a highly tumorigenic, stem-cell like population in other human solid tumor types. In human brain tumors and prostate cancer, expression of CD133+ defined a subpopulation of cancer cells with high tumorigenic potential (6, 30, 31), while in melanoma, the cancer stem cell population was enriched in the CD20+ fraction of cells (32). In human ovarian cancer cells, a side scatter population of cells that bind the Hoechst dye defines a subpopulation of cells with stem cell-like characteristics and enhanced tumorigenicity (10). These studies suggest that several stem cell markers are shared by cancer stem cells in different tumor types, such as CD44 and CD133, however, each tumor may have its own unique phenotype for markers, as highly tumorigenic breast cancer cells are CD24− while their pancreatic counterparts are CD24+.

It has been previously shown that cancer stem cells associated with other types of cancers have aberrant activation of developmental signaling pathways, such as hedgehog, the polycomb family, Wnt, and Notch. To determine if our pancreatic cancer stem cell population had enhanced expression of developmental genes, we chose to examine expression of sonic hedgehog. Misregulation of hedgehog signaling has also been shown to play a role in other types of cancer, including basal cell carcinoma, breast cancer, and small cell lung cancer (25, 27). Hedgehog pathway activation occurs in a significant number of primary human pancreatic carcinomas (28, 29) and PanIn lesions, precursor lesions of invasive pancreatic cancer. Additionally, transgenic overexpression of SHH within the pancreas results in PanIn lesions and the accumulation of genetic mutations commonly seen in pancreatic cancer, including k-ras mutations and upregulation of Her2/Neu, suggesting that Hedgehog signaling is an early mediator of pancreatic cancer tumorigenesis. Inhibition of hedgehog signaling by cyclopamine inhibited pancreatic cancer growth in vitro and in vivo, suggesting that this signaling pathway has an early and critical role in the genesis of pancreatic cancer (28). We found that SHH was markedly upregulated in CD44+CD24+ESA+ cells compared to CD44−CD24−ESA− and bulk pancreatic cancer cells, indicating that SHH is highly upregulated in pancreatic cancer stem cells, with persistent, albeit lower, expression in their differentiated progeny.

REFERENCES

1. Hoyert D L, Heron M P, Murphy S L, Kung, H C. Deaths: final data for 2003. Natl Vital Stat Rep 2006; 19: 1-120.
2. Reya T, Morrison S J, Clarke M F, and Weissman I L. Stem cells, cancer, and cancer stem cells. Nature 2001; 414: 105-111.
3. Bonnet D, Dick J E. Human acute myeloid leukemia is organized as a hierarchy that originates from a primitive hematopoietic cell. Nature Med 1997; 3:730-737.
4. Lapidot T, et. al. A cell initiating human acute myeloid leukemia after transplantation into SCID mice. Nature 1994; 17: 645-648.
5. Al-Hajj M, Wicha M S, Benito-Hernandez A, Morrison S J, Clarke M F. Prospective identification of tumorigenic breast cancer cells. Proc Natl Acad Sci USA. 2003; 100: 3983-8.
6. Singh S K, Hawkins C, Clarke I D, Squire J A, Bayani J, Hide T, Henkelman R M, Cusimano M D, Dirks P B Identification of human brain tumour initiating cells. Nature. 2004; 432: 396-401.
7 Galli R, Binda E, Orfanelli U, Cipelletti B, et al. Isolation and characterization of tumorigenic, stem-like neural precursors from human glioblastoma. Cancer Res 2004; 64: 7011-7021.
8. Hemmati H D, Nakano I, Lazareff J A, Masterman-Smith M, et al. Cancerous stem cells arise from pediatric brain tumors. Proc Natl Acad Sci USA 2003; 100: 15178-15183. 21
9. Patrawala L, Calhoun T, Schneider-Broussard R, Li H, et al. Highly purified CD44+ prostate cancer cells from xenograft human tumors are enriched in tumorigenic and metastatic progenitor cells. Oncogene 2006; 25: 1696-1708.
10. Szotek P P, Pieretti-Vanmarcke R, Masiakos P T, et al. Ovarian cancer side population defines cells with stem cell-like characteristics and Mullerian inhibiting substance responsiveness. Proc Natl Acad Sci 2006; 103: 11154-11159.
11. Costello R T, Mallet F, Gaugler B, Sainty D, et al. Human acute myeloid leukemia CD34+/CD38− progenitor cells have decreased sensitivity to chemotherapy and Fas induced apoptosis, reduced immunogenicity, and impaired dendritic cell transformation capacities. Cancer Res 2000; 60: 4403-4411.
12. Dean M, Fojo T, Bates S. Tumour stem cells and drug resistance. Nat Rev Cancer 2005; 5: 274-284.
13. Guzman M L, Swiderski C F, Howard D S, Grimes B A, et al. Preferential induction of apoptosis for primary human leukemic stem cells. Proc Natl Acad Sci USA 2002; 99: 16220-16225.

14. Arumugam T, Simeone D M, Van Golen K, Logsdon C D. S100P promotes pancreatic cancer growth, survival, and invasion. Clin Cancer Res 2005; 11: 5356-5364.
15. Logsdon C D, Simeone D M, Binkley C, et. Al. Molecular profiling of pancreatic adenocarcinoma and chronic pancreatitis identifies multiple genes differentially regulated in pancreatic cancer. Cancer Res 2003; 63: 2649-2657.
16. Hahn S A, Seymour A B, Hoque A T, et. al. Allelotype of pancreatic adenocarcinoma using xenograft enrichment. Cancer Res 1995; 55: 4670-4675.
17. Litvinov S V, Velders M P, Bakker H A, Fleuren G J, et al. Ep-CAM: a human 22 epithelial antigen is a homophilic cell-cell adhesion molecule. J. Cell Biol. 1994; 125: 437-446.
18. Ponta H, Sherman L, Herrlich P A. CD44: from adhesion molecules to signalling regulators. Nat Rev Mol Cell 2003; 4: 33-45.
19. Weichert W, Denkert C, Burkhardt M, Gansukh T, et al. Cytoplasmic CD24 expression in colorectal cancer independently correlates with shortened patient survival. Clin Cancer Res. 2005; 11:6574-81.
20. Li L, Neaves W B. Normal stem cells and cancer stem cells: the niche matters. Cancer Res 2006; 66: 4553-4557.
21. Liu S, Dontu G, Mantle I D, Patel S, Ahn N S, Jackson K W, Suri P, Wicha M S. Hedgehog signaling and Bmi-1 regulate self-renewal of normal and malignant human mammary stem cells. Cancer Res. 2006, 66 (12):6063-71.
22. Park I-K, Morrison S J, Clarke M F. Bmi1, stem cells, and senescence regulation. J Clin Invest 2004; 113: 175-179.
23. Androutsellis-Theotokis A, Leker R R, Soldner F, et al. Notch signaling regulates stem cell numbers in vitro and in vivo. Nature 2006; 442: 823-826.
24. Lie D C, Colamarino S A, Song H J, et al. Wnt signaling regulates adult hippocampal neurogenesis. Nature 2005; 437: 1370-1375.
25. Yilmaz O H, Valdez R, Theisen B K, Guo, W, et al. Pten dependence distinguishes hematopoietic stem cells from leukemia-initiating cells. Nature 2006; April 5; [Epub ahead of print].
26. Ayyanan A, Civenni G, Ciarloni L, Morel C, et al. Increased Wnt signaling triggers oncogenic conversion of human breast epithelial cells by a Notch dependent mechanism. 23 Proc Natl Acad Sci USA 2006; 103: 3799-3804.
27. Pasca di Magliano M, Hebrok M. Hedgehog signaling in cancer formation and maintenance. Nat Rev Cancer 2003; 3: 903-911.
28. Thayer S P, Pasca di Magliano M, Heiser P W, Nielson C M, et al. Hedgehog is an early and late mediator of pancreatic cancer tumorigenesis. Nature 2003; 425: 851-856.
29. Berman D M, Karhadkar S S, Maitra A, de Oca R M, et al. Widespread requirement for hedgehog ligand stimulation in growth of digestive tract tumours. Nature 2003; 425: 846-851.
30. Singh S K, Clarke I D, Terasaki M, Bonn V E, Hawkins C, Squire J, Dirks P B. Identification of a cancer stem cell in human brain tumors. Cancer Res. 2003; 63: 5821-8.
31. Richardson G D, Robson C N, Lang S H, Neal D E, et al. CD133, a novel marker for human prostate epithelial stem cells. J Cell Sci 2004; 117: 1539-1545.
32. Fang D, Nguyen T K, Leishear K, Finko R, Kulp A N, Hotz S, Van Belle P A, Xu X, Elder D E, Herlyn M. A tumorigenic subpopulation with stem cell properties in melanomas. Cancer Res. 2005; 65: 9328-37.
33. Matsui W, Huff C A, Wang Q, et al. Characterization of clonagenic multiple myeloma cells. Blood 2004; 103: 2332-2336.

All publications and patents cited herein are incorporated by reference herein in entirety. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An isolated population of at least $10^3$ human pancreatic cancer cells comprising at least 75% pancreatic cancer stem cells, wherein the pancreatic cancer stem cells are:
   (a) $CD44^+CD24^+ESA^+$ and
   (b) tumorigenic.

2. The isolated population of human pancreatic cancer cells of claim 1, which is obtained from a tumor of pancreatic epithelial origin, and wherein said at least $10^3$ human pancreatic cancer cells comprises at least $10^4$ human pancreatic cancer cells.

3. The isolated population of human pancreatic cancer cells of claim 1, wherein the pancreatic cancer stem cells are in a culture medium.

4. The isolated population of human pancreatic cancer cells of claim 1, wherein the pancreatic cancer stem cells are affixed to a substrate.

5. An enriched population of at least $10^2$ human pancreatic cancer cells comprising human tumorigenic $CD44^+CD24^+ESA^+$ pancreatic cancer stem cells, wherein the pancreatic cancer stem cells are
   enriched in said enriched population at least four-fold compared to an equally sized unfractionated population of human pancreatic cancer cells.

6. The enriched population of claim 5, wherein the $CD44^+CD24^+ESA^+$ pancreatic cancer stem cells in said enriched population are enriched at least 10-fold compared to an equally sized unfractionated population of human pancreatic cancer cells.

7. The enriched population of claim 5, wherein the $CD44^+CD24^+ESA^+$ pancreatic cancer stem cells in said enriched population are enriched at least 20-fold compared to an equally sized unfractionated population of human pancreatic cancer cells.

8. The enriched population of claim 5, which is obtained from a solid tumor of pancreatic epithelial origin.

9. The enriched population of claim 5, wherein the $CD44^+CD24^+ESA^+$ pancreatic cancer stem cells have at least a 100-fold increased tumorigenic potential compared to non-tumorigenic pancreatic cancer cells.

10. The enriched population of claim 5, wherein said at least $10^2$ human pancreatic cancer cells comprises at least $10^3$ human pancreatic cancer cells.

11. The enriched population of claim 6, wherein said at least $10^2$ human pancreatic cancer cells comprises at least $10^4$ human pancreatic cancer cells.

* * * * *